(12) United States Patent
Currie

(10) Patent No.: US 8,333,874 B2
(45) Date of Patent: Dec. 18, 2012

(54) FLEXIBLE APPARATUS AND METHOD FOR MONITORING AND DELIVERY

(75) Inventor: John Frederick Currie, Bethesda, MD (US)

(73) Assignee: Flexible Medical Systems, LLC, Rockville, MD (US)

( * ) Notice: Subject to any disclaimer, the term of this patent is extended or adjusted under 35 U.S.C. 154(b) by 669 days.

(21) Appl. No.: 12/096,769

(22) PCT Filed: Jun. 14, 2006

(86) PCT No.: PCT/US2006/023194
§ 371 (c)(1),
(2), (4) Date: Mar. 17, 2009

(87) PCT Pub. No.: WO2007/070093
PCT Pub. Date: Jun. 21, 2007

(65) Prior Publication Data
US 2009/0308742 A1 Dec. 17, 2009

(30) Foreign Application Priority Data

Dec. 9, 2005 (WO) ................ PCT/US2005/044287

(51) Int. Cl.
*G01N 27/26* (2006.01)
(52) U.S. Cl. ........................ 204/403.01; 435/7.1; 435/14
(58) Field of Classification Search ............... 204/403.01–403.15; 435/4–40.52
See application file for complete search history.

(56) References Cited

U.S. PATENT DOCUMENTS

| | | |
|---|---|---|
| 4,526,176 A | 7/1985 | Bremer et al. |
| 4,775,361 A | 10/1988 | Jacques et al. |
| 4,821,733 A | 4/1989 | Peck |
| 4,909,256 A | 3/1990 | Peck |
| 5,019,034 A | 5/1991 | Weaver et al. |
| 5,123,902 A | 6/1992 | Muller et al. |

(Continued)

FOREIGN PATENT DOCUMENTS

EP 1003033 5/2000
(Continued)

OTHER PUBLICATIONS

Nijdam, A.J. et al., "Fluidic encapsulation in SU-8 [micro]-reservoirs with [micro]-fluidic through-chip channels", Sensors and Actuators A, vol. 120, Apr. 29, 2005, p. 172-183.*

(Continued)

*Primary Examiner* — J. Christopher Ball
(74) *Attorney, Agent, or Firm* — The Marbury Law Group, PLLC

(57) ABSTRACT

The present invention generally relates to a system and method that co-locates in a small flexible, configurable system and multi-level substrate sampling, rapid analysis, bio-sample storage and delivery functions to be performed on living tissues or matter obtained from living organisms. The types of the sampling may include chemical, biochemical, biological, thermal, mechanical, electrical, magnetic and optical sampling. In general, the analysis performed at the point of sampling measures the sample taken and records its value. The bio-sample storage function encapsulates a small sample of analyte and preserves it for subsequent examination or analysis, either on the organism by the system or at a remote location by an independent analysis system. Once stored, the sample can provide a record of a biological state at the precise time of sampling. The delivery at the point of sampling can include chemical, biochemical, biological, thermal, mechanical, electrical, magnetic and optical stimuli.

34 Claims, 30 Drawing Sheets

U.S. PATENT DOCUMENTS

| | | | |
|---|---|---|---|
| 5,149,629 | A | 9/1992 | Rishpon et al. |
| 5,176,881 | A | 1/1993 | Sepaniak et al. |
| 5,203,327 | A | 4/1993 | Schoendorfer et al. |
| 5,284,748 | A | 2/1994 | Mroczkowski et al. |
| 5,330,527 | A | 7/1994 | Montecalvo et al. |
| 5,366,454 | A * | 11/1994 | Currie et al. ............... 604/890.1 |
| 5,380,272 | A | 1/1995 | Gross |
| 5,458,140 | A | 10/1995 | Eppstein et al. |
| 5,711,861 | A | 1/1998 | Ward et al. |
| 5,722,397 | A | 3/1998 | Eppstein |
| 5,730,714 | A | 3/1998 | Guy et al. |
| 5,885,211 | A | 3/1999 | Eppstein et al. |
| 5,983,131 | A | 11/1999 | Weaver et al. |
| 6,022,316 | A | 2/2000 | Eppstein et al. |
| 6,056,738 | A | 5/2000 | Marchitto et al. |
| 6,124,597 | A | 9/2000 | Shehada et al. |
| 6,144,869 | A | 11/2000 | Berner et al. |
| 6,233,471 | B1 | 5/2001 | Berner et al. |
| 6,270,651 | B1 | 8/2001 | Essalik et al. |
| 6,342,037 | B1 | 1/2002 | Roe et al. |
| 6,393,318 | B1 | 5/2002 | Conn et al. |
| 6,464,687 | B1 | 10/2002 | Ishikawa et al. |
| 6,572,542 | B1 | 6/2003 | Houben et al. |
| 6,597,946 | B2 | 7/2003 | Avrahami et al. |
| 6,887,202 | B2 | 5/2005 | Currie et al. |
| 6,922,578 | B2 | 7/2005 | Eppstein et al. |
| 6,922,586 | B2 | 7/2005 | Davies |
| 7,001,495 | B2 | 2/2006 | Essalik et al. |
| 7,826,981 | B2 | 11/2010 | Goode, Jr. et al. |
| 2001/0052459 | A1 | 12/2001 | Essalik et al. |
| 2003/0130616 | A1 | 7/2003 | Steil et al. |
| 2003/0208152 | A1 | 11/2003 | Avrahami et al. |
| 2003/0225362 | A1 | 12/2003 | Currie et al. |
| 2004/0157319 | A1 | 8/2004 | Keen |
| 2004/0193219 | A1 | 9/2004 | Asano et al. |
| 2004/0253304 | A1 | 12/2004 | Gross et al. |
| 2005/0069454 | A1 | 3/2005 | Bell |
| 2005/0182307 | A1 | 8/2005 | Currie et al. |
| 2005/0226921 | A1 | 10/2005 | Kortzebom |
| 2006/0241514 | A1 | 10/2006 | Davies |
| 2009/0281404 | A1 | 11/2009 | Currie et al. |

FOREIGN PATENT DOCUMENTS

| | | |
|---|---|---|
| WO | 97/42882 A1 | 11/2007 |

OTHER PUBLICATIONS

Currie et al., "Novel Non-Intrusive Trans-Dermal Remote Wireless Micro-Fluidic Monitoring System Applied to Continuous Glucose and Lactate Assays for Casualty Care and Combat Readiness," NATO: RTO-MP-HFM-109, pp. 24-1-24-17 (2004).

Gadre et al., "Fabrication of a fluid encapsulated dermal patch using multilayered SU-8," Sensors and Actuators A: Physical, 114(2-3):478-485 (2004).

Paranjape et al., "A PDMS dermal patch for non-intrusive transdermal glucose sensing," Sensors and Actuators A: Physical, 104(3):195-204 (2003).

Information Disclosure Statement filed on Oct. 20, 2008 in related U.S. Appl. No. 11/721,287.

International Search Report and Written Opinion, PCT/US05/44287, 5 pages, Aug. 28, 2006.

Preliminary Examination Report, PCT/USO 1/17081, 5 pages, Sep. 17, 2004.

Balabanova et al., "Detection of Drugs in Sweat (Nachweis von Drogen im schweib)" Beitr. Gerichtl. Med., vol. 48, pp. 45-49, 1990.

Henderson et al., "Excretion of Methadone and Metabolites in Human Sweat," Research Communications in Chemical Pathology and pharmacology, vol. 5, No. 1, pp. 1-8, Jan. 1973.

Peck et al., "Outward Transcutaneous Chemical Migration: Impliations for Diagnostics and Dosimetry", Skin Pharmacol., vol. 1, No. I, pp. 14-23, 1988.

Phillips et al., "A Sweat-Patch Test for Alcohol Consumption: Evaluation in Continuous and Episodic Drinkers", Alcohol: clinical and Experimental research, vol. 4, No. 4, pp. 391-395, 1980.

"SpectRx an Innovactive Medical Technology Company" [online], Copyright 2004 [retrieved on Aug. 31, 2004], 1 p., Retrieved from the Internet: hhtp://www.spectrx.com.

Schneider et al., "B-Fit System: Bio-Flips Integrable Transdermal MicroSystem", ARO Workshop on Biomolecular Signaling, Energy Transfer, and Transduction Processes, Cashiers, NC, 16 pages, May 14-17, 2000.

Smith et al., "Cocaine in Hair, Saliva, Skin Swabs, and Urine of Cocaine Users' Children", Forensic Science International, vol. 83, pp. 179-189, 1996.

Non-Final Office Action with List of References cited by the Examiner mailed on Dec. 3, 2010 issued in U.S. Appl. No. 11/721,287.

Non-Final Office Action with List of References cited by the Examiner mailed on Jan. 27, 2012 issued in U.S. Appl. No. 11/721,287.

Information Disclosure Statement filed Jun. 18, 2012 in related U.S. Appl. No. 13/294,368.

Information Disclosure Statement filed Sep. 11, 2012 in related U.S. Appl. No. 13/609,838.

Notice of Allowance and Fee(s) Due with Examiners Amendment, issued Aug. 16, 2012 in related U.S. Appl. No. 11/721,287.

International Search Report with Written Opinion, PCT/US2011/06558, 15 pages, issued Jul. 25, 2012, mailed Jul. 27, 2012.

* cited by examiner

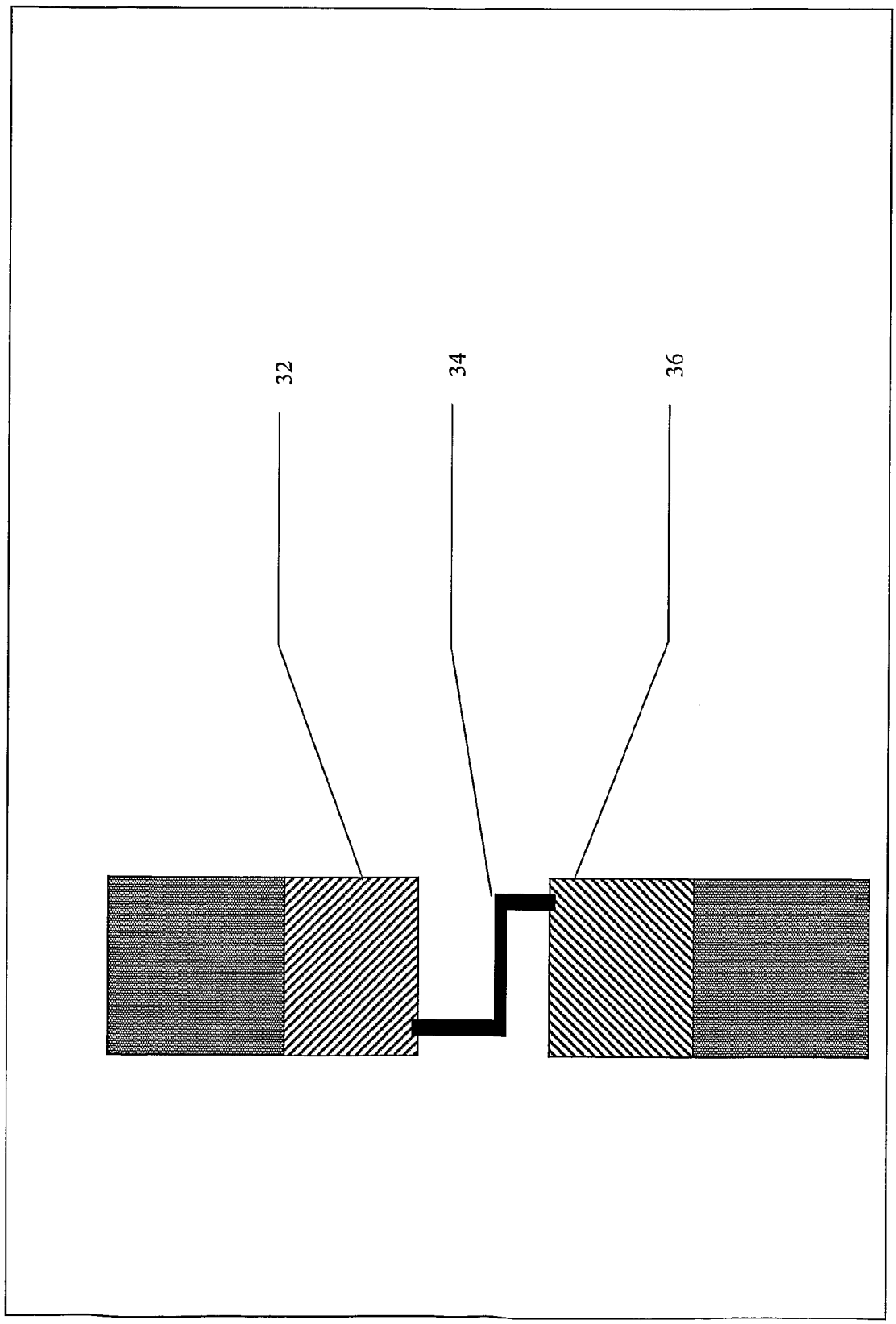

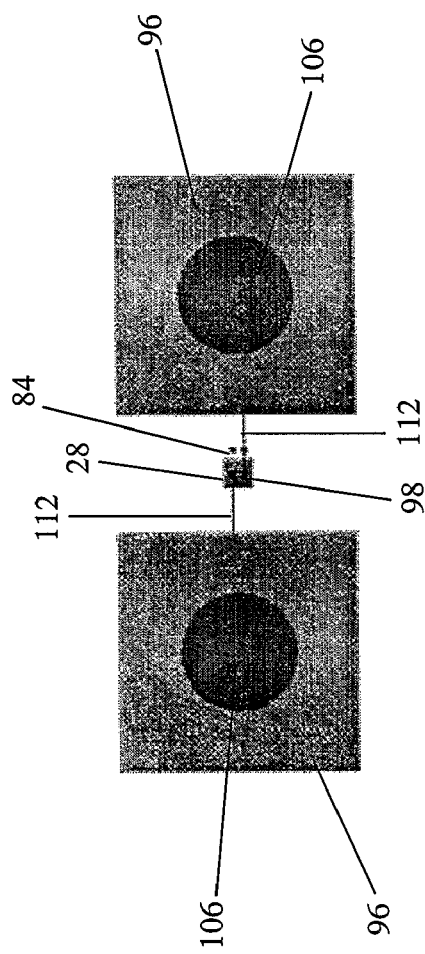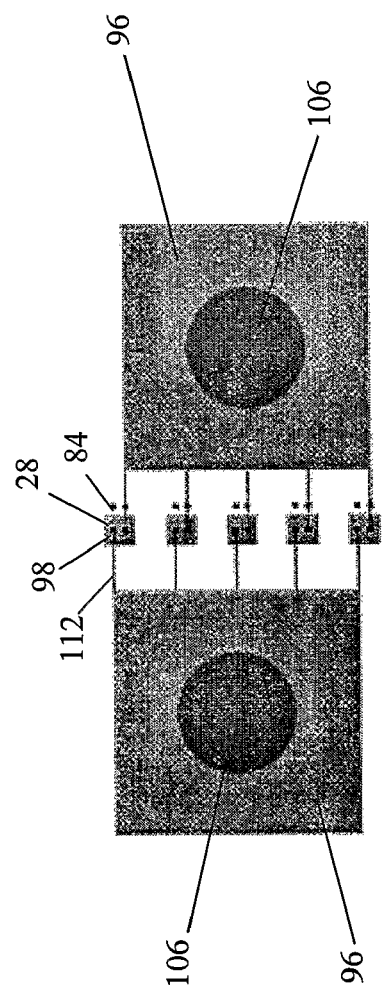
FIG. 22
FIG. 23

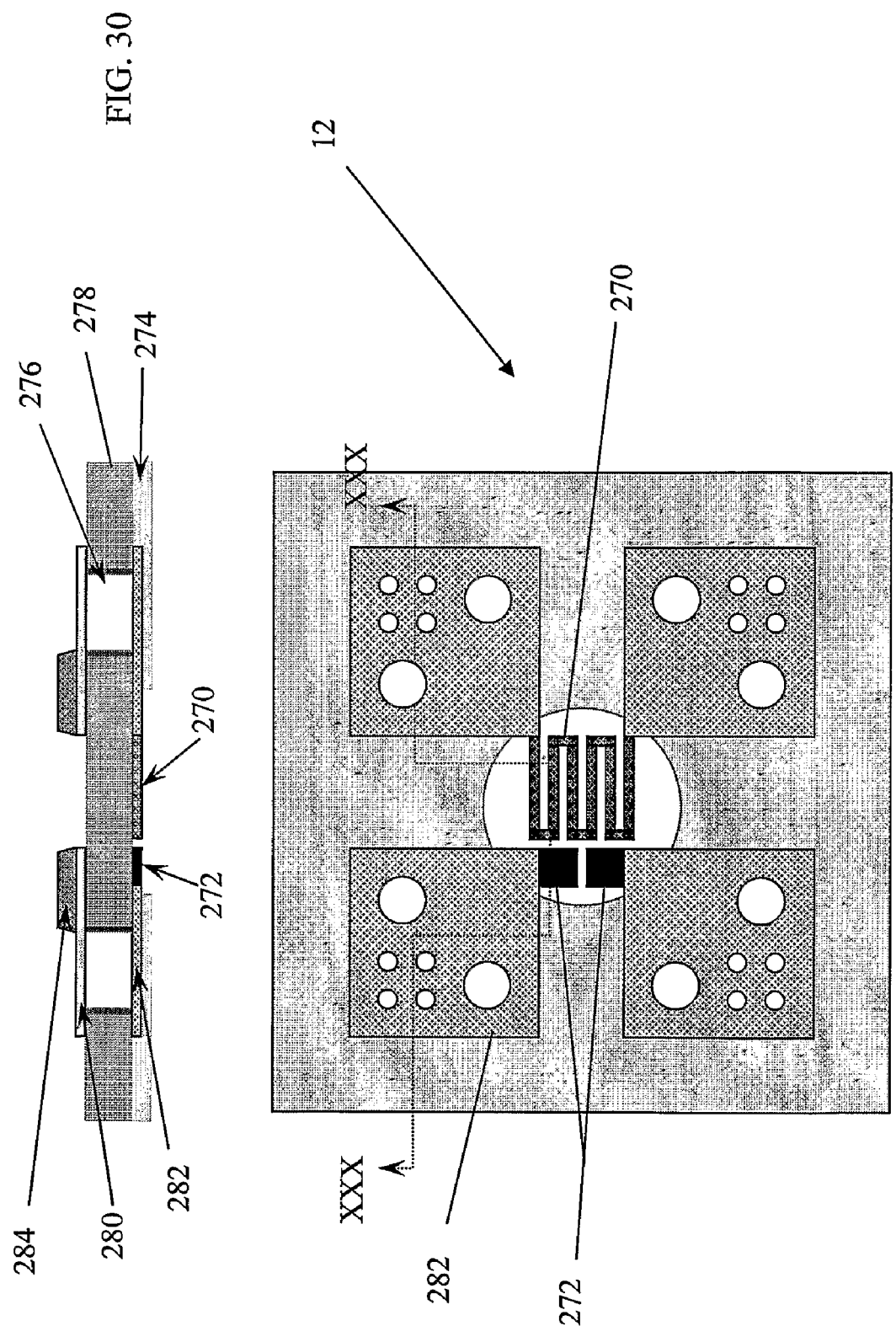

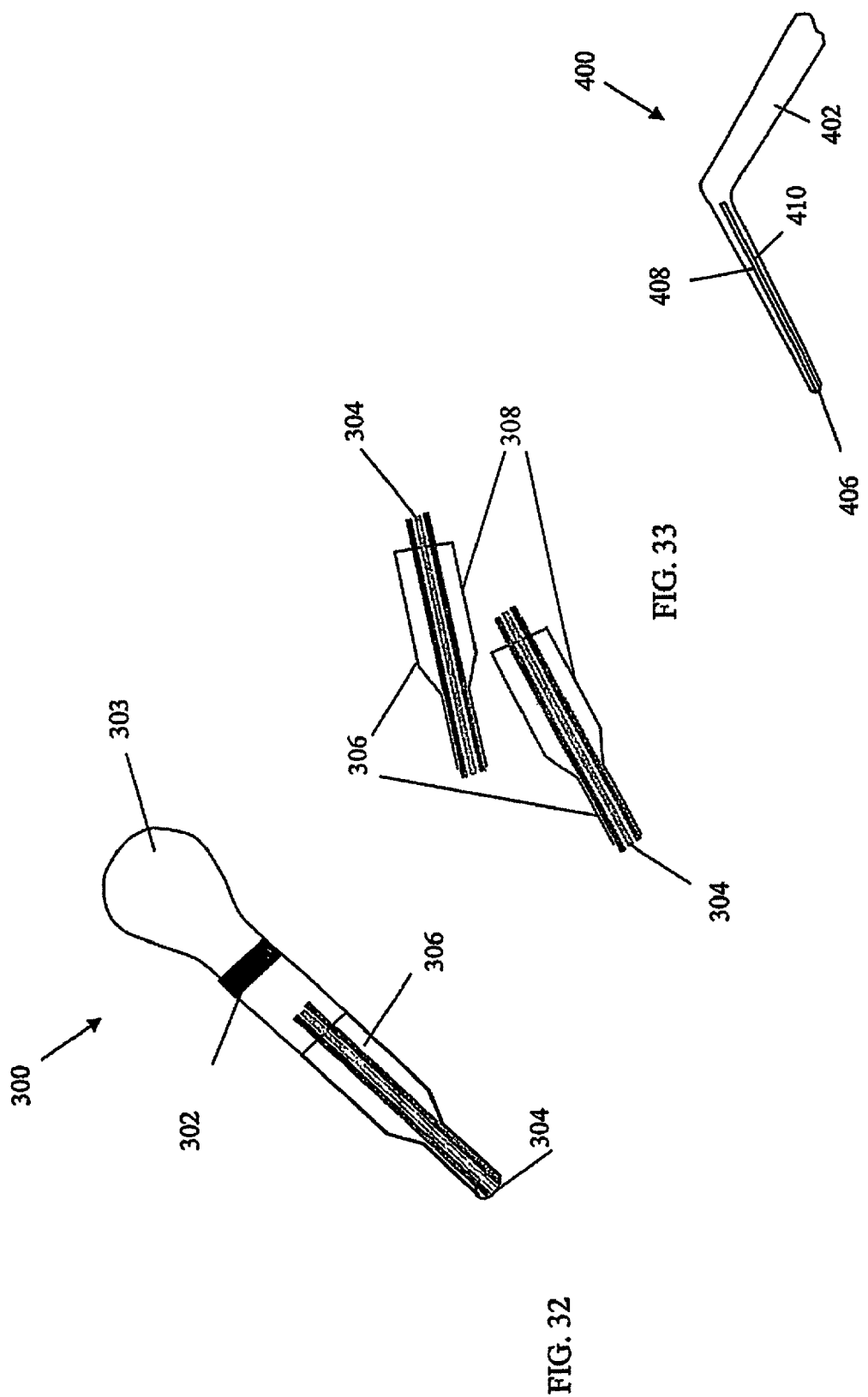

FLEXIBLE APPARATUS AND METHOD FOR MONITORING AND DELIVERY

CROSS-REFERENCE TO RELATED APPLICATIONS

This application is the National Phase of International Patent Application No. PCT/US2006/023194, which is a continuation in part of International Patent Application No. PCT/US2005/044287, filed on Dec. 9, 2005 and titled "Apparatus and Method for Continuous Real-Time Trace Biomolecular Sampling, Analysis and Delivery", which claims the benefit of U.S. Provisional Patent Application No. 60/634,783, filed on Dec. 9, 2004 and titled "Systems and Methods for Monitoring Health and Delivering Drugs Transdermally", the entire contents of which are both hereby incorporated by reference.

FIELD OF INVENTION

The present invention relates to the field of portable biomedical and bio-molecular monitoring, remote diagnostics and connected healthcare. More specifically, the present invention relates to a method, apparatus, and system for a configurable flexible personal health monitoring and material delivery system.

BACKGROUND OF INVENTION

Non-invasive, transdermal sampling of body fluids has long been a goal of medical research. Prior art attempts to achieve this goal are described in, for instance U.S. Pat. No. 6,887,202 issued on May 3, 2005 to Currie et al. entitled "Systems and Methods for Monitoring Health and Delivering Drugs Transdermally" the contents of which are hereby incorporated by reference.

The prior attempts at transdermal sampling have typically been characterized by making relatively large holes in the outermost layer of the epidermis, namely the stratum corneum which is effectively the surface of the skin and is composed mainly of dead cells that lack nuclei. The holes are typically made by heat or laser ablation or puncturing with fine needles and reach through to underlying, viable epidermis. Interstitial fluid from the viable epidermis or fluid from the extremity of the vascular system is then typically either sucked up, or squeezed out, from beneath the skin into the transdermal device where it is analyzed spectroscopically using systems of micro-fabricated channels and light guides.

Such systems have many drawbacks, including the fact that the size of the holes is typically of the order of tens of microns which is sufficient to cause local irritation. This often results in inflammation, which typically prevents the channels typically from being maintained open for longer than a few hours to a few days.

Furthermore, micro-fabrication of complex systems typically requires the use of silicon substrates, which are relatively inflexible, thereby making close surface contact difficult and resulting in lateral motion between the transdermal detector and the holes through the stratum corneum. Because of the size of the transdermal holes, typically tens of microns in diameter, even a small amount of lateral motion can render such a device inoperative.

It is desirable to provide a configurable flexible personal health monitoring and delivery system that may be configured to be used in a much wider range of applications. It is also desirable to provide a sampling device that may be used in invasive, minimally invasive, and non-invasive procedures involving transdermal and non-transdermal sampling.

SUMMARY OF INVENTION

The present invention generally relates to a system and method that co-locates in a small flexible, configurable system and multi-level substrate sampling, rapid analysis, biosample storage and delivery functions to be performed on living tissues or matter obtained from living organisms. In the multiple application areas described below, the types of the sampling may include chemical, biochemical, biological, thermal, mechanical, electrical, magnetic and optical sampling. In general, the analysis performed at the point of sampling measures the sample taken and records its value. The bio-sample storage function encapsulates a small sample of analyte and preserves it for subsequent examination or analysis, either on the organism by the system or at a remote location by an independent analysis system. Once stored, the sample can provide a record of a biological state at the precise time of sampling. The delivery at the point of sampling can include chemical, biochemical, biological, thermal, mechanical, electrical, magnetic and optical stimuli.

The results of the measurements may provide a quantitative snapshot at the instant of sampling and measurement of the health of the tissues measured or the organism being monitored. When values are measured that fall outside of normal biomedical ranges, a possible disease state can be reported, and intervention may be taken to restore the organism to its healthy state.

Monitoring is broadly defined as the activity of periodic measurement of a biological process (e.g. physiological, biochemical or metabolic), which seeks to establish the extent to which input biological functioning is within normal, functioning, healthy bounds, so that timely action can be taken to correct the deficiencies detected. Closely linked to monitoring is evaluation. Evaluation is a process by which measured results are analyzed and judged explicitly against individual and population norms. Similarly, the biological environment (including air, food, water, medications, temperature etc.) of a person, animal tissue or organism can be monitored for its input to the biological process. Examples of the types of monitoring for which this system is designed include: monitoring of the biological and chemical environment for safety; monitoring to discover and maintain individual healthy baseline behavior; monitoring for early disease detection; monitoring for disease progression, including secondary effects (disease burden); medical intervention including drug administration; monitoring for treatment efficacy; monitoring for therapeutic compliance; and/or monitoring for possible relapse.

Monitoring in these situations can be either acute or chronic. There may be only a single-measurement at one desired, prepared or controlled instant. The time scale of repeated measurements may be variable, from minutes to weeks, or from over an hour to over decades. The bio-chemical concentration scales may vary from trace 1 pg/dl to concentrated 1 g/dl, or over twelve orders of magnitude.

The disposable sampling part of the system may be mechanically flexible, made of multiple thin layers of structural and functional films, so as to deform to take the shape of the tissue to be monitored and adhere to it. As described below, the contact obtained is minimally intrusive, i.e., it does not disrupt the viable functioning of the tissue or perturb the measurement targets by their presence. Similarly, the flexible sampling part can fit into a suitable package for the analysis of bio-fluids and biological or chemical samples. Sensors may be attached to different sampling sites such as cheek, gum, nasal, throat, sinus, ear and eye tissues. Each location can give unique sampling characteristics. For example, the eye and inner ear give access to the central nervous system inside the blood-brain barrier.

The system and all of its constituent parts is configurable as to the positioning of the sampling on the organism, the number and variety of measurement targets as well as the frequency, redundancy, recording and reporting of the individual measurements. The types of configuration can be classified as follows: the identification of measurement targets; the size of the measurement target; position of the sample; the type of sample mechanism, such as non-invasive, minimally invasive, or invasive; the type of sample taken; the storage of the sample; the modification of the sample; and the number of determinations of a single measurement target. Further, the details of the configurations should be modified over time to suit the purpose of the health monitoring.

The system described in further detail below may be used in a wide variety of applications area, including but not limited to: diabetes monitoring and treatment; resuscitative medicine, including hemorrhagic shock, trauma, burns, etc.; detection and treatment of pediatric jaundice; monitoring of stamina, physical performance, fatigue, and alertness; testing tissue viability; performing a tissue biopsy; early detection of diseases, such as cancer and infectious diseases, and responses to treatment of such diseases; detection and treatment of dental gum disease, such as bacteria, viruses, microbial film, inflammation and caries, as well as normal hormones, proteins and metabolites to assess overall wellness; monitoring obesity, diet, exercise, weight, and overall body composition management; monitoring cardio- and vascular functions, as well as stroke; drug discovery and development screening; drug pharmacokinetic, individual dosing, efficacy, safety, toxicity, secondary effects, interference and pharmacological studies and clinical trials; detecting and treating infectious diseases, including but not limited to influenza, malaria, and Dengue fever; neural interfacing for short-term or for long-term interfacing, such as for prosthetic control and therapeutic response; monitoring of neurological disorders such as depression, anxiety, multiple sclerosis; monitoring animals, crops, water, food supplies, etc.; monitoring for substance and drug use and abuse, such as smoking, alcohol, narcotics, etc.; drug dosing clinics, such as anti-coagulants. In addition, the system may be used in conjunction with biomedical instrumentation, to provide direct feedback of treatment efficacy of radiation, chemo, exercise, dialysis, ventilator, tissue and organ support systems. The system may also be used for implant tissue monitoring for viability and functionality of tissues to be removed and of tissues to be implanted, both before and following surgery.

It is an aspect of the present invention to provide a method for monitoring a biological condition in a subject. In an embodiment, the method includes exposing a sensor of a sampling, analysis and delivery device to a substance comprising a targeted bio-molecule, providing an electrical signal to the sensor; measuring an electrical property at the sensor in response to the electrical signal; correlating the measured electrical property to the biological condition; determining whether the measured biological condition is normal or abnormal; and generating a signal when the measured biological condition is abnormal.

In an embodiment, the targeted bio-molecule is selected from the group consisting of glucose, lactate, bilirubin, ethanol, pyruvate, and cytochrome P-450 2A6 enzyme.

In an embodiment, the targeted bio-molecule is selected from the group consisting of glucosylated hemoglobin and proteins, insulin, cholesterol, C-reactive proteins, homocysteine, orexins, Histidine-rich protein 2 of P. falciparum, parasite lactatedehydrogenase, prostate specific antigen, prostate membrane specific antigen, estrogen, epidermal growth factor, insulin growth factor, Hemagglutinin, Neuradminidase, 17 kDa subunit of cleaved caspase-3, proteins like p54, immunoglobulin, narcotics, leptin, ghrelin, vitamins, folic acid, creatine kinase (CK and CK-MB), troponin, C-reactive protein, tumor necrosis factor receptors 1 and 2, creatine phosphokinase (CK and CK-MB), creatinine, troponin, interleukins 1, 2 and 6, interleukin-2 receptor, tumor necrosis factor-alpha, n-nitrosamines, nicotine, cotinine, opiates, cocaine, and spore metabolites.

In an embodiment, the targeted bio-molecule is selected from the group consisting of influenza viruses, multiple sclerosis viruses, Dengue fever, malaria, HIV, and tuberculosis.

It is another aspect of the present invention to provide a method for biomolecular monitoring. In an embodiment, the method includes sampling a substance that includes a biochemical, and analyzing the substance with a pair of electrodes. The pair of electrodes is disposed on a support substrate. The method also includes controlling the sampling and the analyzing with a controller, and communicating information between the controller and a remote device.

It is an aspect of the present invention to provide a system for sampling, analyzing, and/or delivering at least one biochemical. In an embodiment, the system includes a support substrate, and a plurality of cells supported by the support substrate and arranged in a plurality of columns and a plurality of rows. Each of the plurality of cells is configured to sample, analyze, and/or deliver the biochemical. The system also includes a controller configured to control an interaction of each of the plurality of cells with a substance associated with the biochemical. The controller is connected to the plurality of cells via a plurality of column address conductive paths, a plurality of row address conductive paths, and a plurality of zero-insertion force connectors. The system further includes a communications device configured to communicate with the controller and an external device.

It is another aspect of the present invention to provide a system for analyzing a property of a substance. In an embodiment, the system includes a support substrate, and a plurality of sensors that are supported by the support substrate. Each sensor includes a pair of electrodes supported by the substrate. The pair of electrodes includes a working electrode and a reference electrode. The working electrode is electrochemically activated and configured to react with the substance. When a voltage is applied across the electrodes and at least the working electrode is exposed to the substance, an electrical property corresponding to the property of the substance is generated. The system also includes a controller for controlling a sequence of electrical signals to the electrodes, and receiving the electrical property that is generated.

It is a further aspect invention to provide a sensor for sensing a property of a substance that includes a biomolecule. In an embodiment, the sensor includes a pair of electrodes supported by a substrate. The pair of electrodes includes a working electrode and a reference electrode. The working electrode is electrochemically activated and configured to react with the substance. When a voltage is applied across the electrodes and at least the working electrode is exposed to the substance, an electrical property corresponding to the property of the substance is generated.

It is yet another aspect of the present invention to provide a sampling device for sampling a substance that includes a biochemical. In an embodiment, the sampling device includes a support substrate, and a pair of electrodes supported by the substrate. The pair of electrodes is configured to disrupt a protective membrane located between the support substrate and the substance.

It is an aspect of the present invention to provide a method for analyzing a biochemical in a substance. In an embodiment, the method includes exposing at least a working electrode of a sensor to the substance, applying a voltage across the working electrode and a reference electrode, measuring an electrical property generated as a result of said applying said voltage across the electrodes, and correlating the measured electrical property with a property of the substance.

It is a further aspect of the present invention to provide a method for filling a cavity in a support layer of a delivery device. In an embodiment, the method includes positioning a seal layer having a hole therein on the support layer such that the hole is positioned above the cavity, filling the cavity with a material, positioning the seal layer relative to the support layer such that the hole is moved away from the cavity and the cavity is covered by the seal layer, and bonding the seal layer to the support layer.

It is an aspect of the present invention to provide a method for manufacturing a device for analyzing a property of a substance. In an embodiment, the method includes wiring connections between a plurality of connectors and a plurality of electrodes located on a support substrate, exposing the plurality of electrodes a polymer matrix, providing an electrochemical potential to select electrodes from the plurality of electrodes with respect to ground, and coating the select electrodes with the polymer matrix.

These and other aspects of the system will now be described by reference to the accompanying drawings.

BRIEF DESCRIPTION OF THE DRAWINGS

To understand the inventive concepts of the present invention, it is useful to consider the accompanying drawings in which, as far as possible, like numbers represent like elements, and wherein:

FIG. 4A is a schematic top view a geometry of a sampling and analysis cell according to an embodiment of the invention;

FIG. 22 is a schematic top view of an embodiment of an interface for filling a single cavity of the device;

FIG. 23 is a schematic top view of an embodiment of an interface for simultaneously filling five cavities of the device;

FIG. 29 is a schematic drawing of a top view of an embodiment of the device;

FIG. 30 is a cross-sectional view taken along line XXX-XXX in FIG. 29;

FIG. 32 is schematic drawing of an embodiment of hand-held sampler that may be used in dental applications;

FIG. 33 is a schematic drawing of an embodiment of a pair of plugs that may be used with the hand-held sampler of FIG. 32; and FIG. 34 is a schematic drawing of an embodiment of a micro-capillary based dental probe device.

DETAILED DESCRIPTION

Overview of System and Method

The present invention generally relates to a method, apparatus, and system for a configurable flexible personal health monitoring and delivery system. More specifically, present invention relates to a system and method for selective sampling of substances, including but not limited to interstitial and biological fluids, for selective measurement of properties of interest, including but not limited to bio-molecules present in the sample. In addition, the system and method may provide for the release-on-command of stored materials, including but not limited to chemicals, biochemicals, and drugs.

Figure 1:
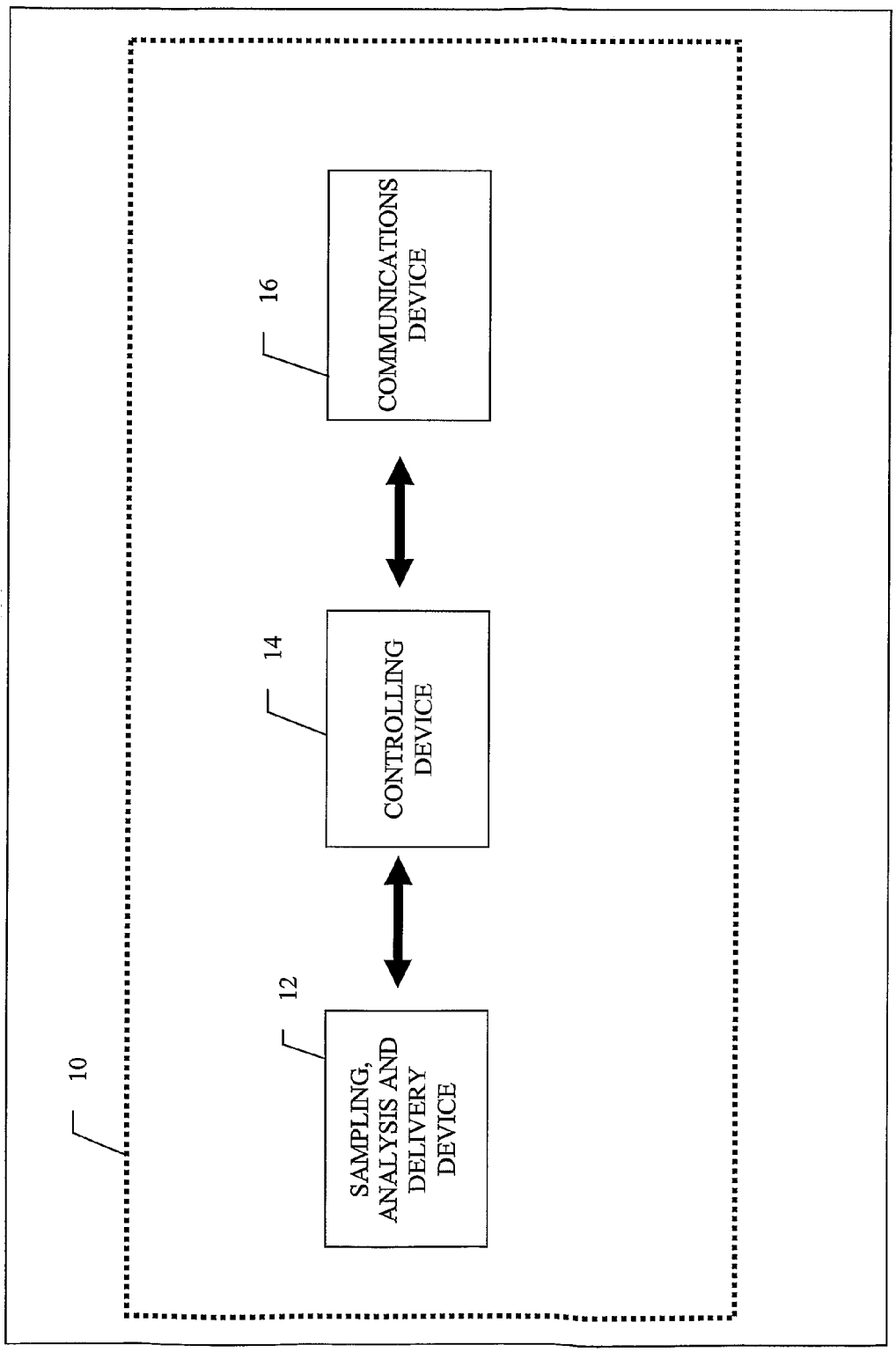
FIG. 1 is a schematic drawing showing an embodiment of a biomolecular sampling and delivery system.

FIG. 1 is a schematic drawing showing an embodiment of a configurable flexible personal health monitoring and delivery system 10 of the present invention. In the illustrated embodiment, the system 10 includes three cooperating devices, including a sampling, analysis and delivery device 12, a controlling device or controller 14 in communication with the sampling, analysis and delivery device 12, and a communications device 16 that allows transmission of data to and from remote loggers, controllers or any other device that is configured to transmit and/or receive data.

As will be discussed in further detail below, the sampling, analysis and delivery device 12 may be configured to sample a substance and/or analyze the substance and/or deliver a material, such as a chemical, biochemical or drug, to the substance that has been sampled and/or analyzed. As such, the phrase "sampling, analysis and delivery device" should not be construed as requiring the device to provide all three functions in all embodiments. To the contrary, in some embodiments, the device 12 may be configured to sample the substance and analyze the substance, or only sample the substance or only analyze the substance. Any combination of these three functions is considered to be within the scope of the present invention. As will be discussed in further detail below, in an embodiment, the device 12 may be a flexible, compliant, sterile, disposable micro fluidic electrochemical chip that includes a plurality of electrochemical sensor cells.

In an embodiment, the controller 14 may include a flexible cable and connector that connects to the device 12 such that the controller 14 communicates with the plurality of electrochemical sensor cells. The controller 14 may also include a wireless control and messaging unit that is configured to communicate with the communications device 16, and the communications device 16 may be configured to communicate with a remote, preferably wireless, computer or any other device that is configured to receive data. For example, the remote device may be a cellular phone, camera, music player, or any other device that contains memory. The controller 14 and the communications device 16 will also be discussed in further detail below.

It will be appreciated by one of skill in the art that embodiments of the system 10 may be used in a wide range of applications where monitoring a substance for a predetermined condition is desired. In general, the system 10 may be used to monitor for specific abnormal biochemical conditions, such as diseases, and treat such conditions upon detection.

Figure 25:
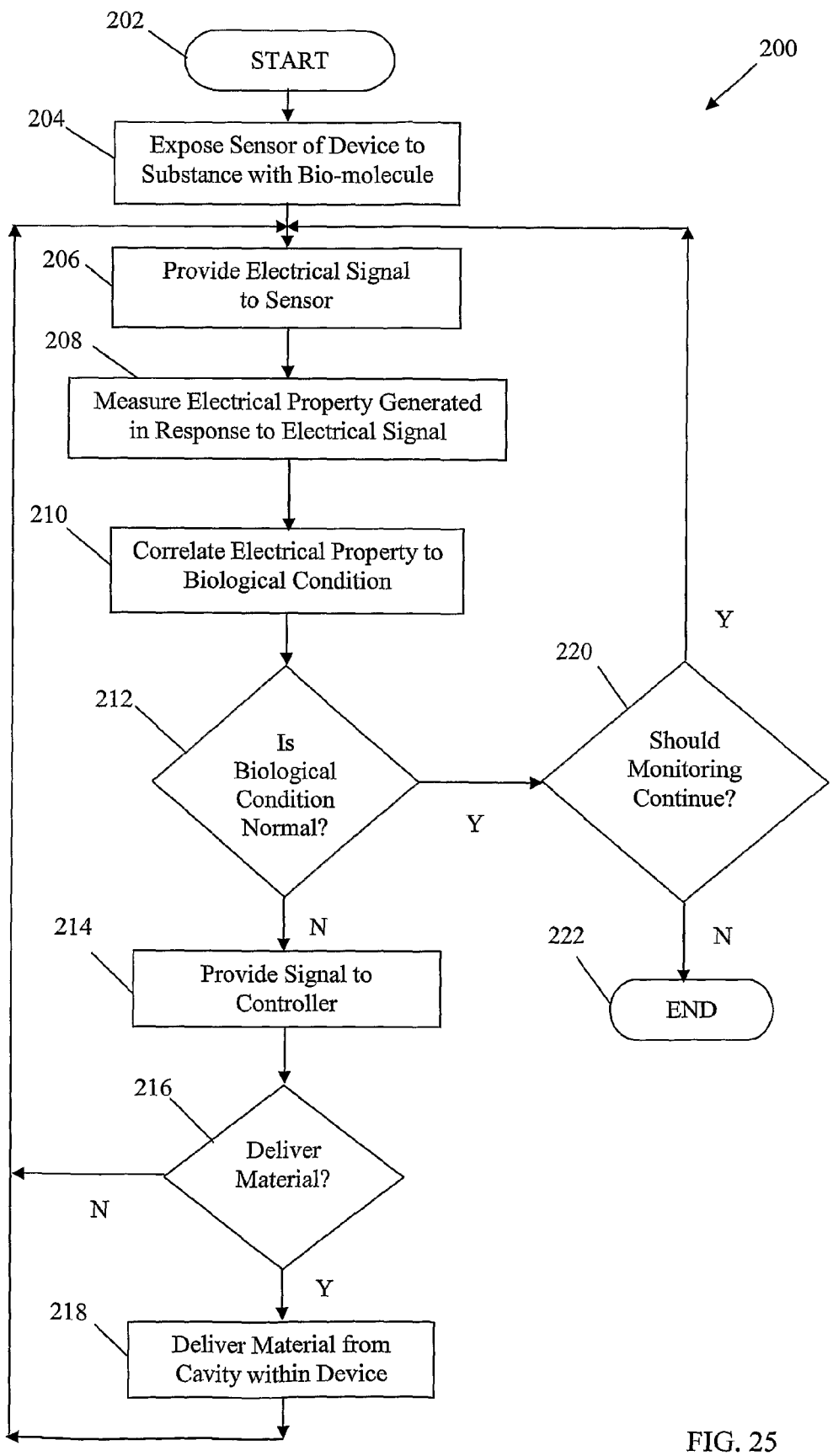
FIG. 25 is a flow diagram illustrating an embodiment of a method for monitoring and treating an abnormal biochemical condition in a subject.

As shown in FIG. 25, in an embodiment, a method 200 for monitoring a biochemical condition, such as a disease, in a subject with the system 10 described herein is provided. The subject may be a person, an animal, a living tissue, an organ, or a non-living substance such as food or water. The method 200 of this embodiment begins at 202. At 204, a sensor of the sampling, analysis and delivery device 12 may be exposed to a substance comprising a targeted bio-molecule by placing the device 12 on the subject at a suitable location. The device 12 may be communicated to a monitoring system via the controller 14 and communications device 16. Once the device 12 is in place and the system 10 is functioning, the subject may be monitored for a predetermined amount of time to establish the subject's normal healthy baseline behavior. For example, bio-molecules within the subject's bloodstream that may be detected through a sampling of the subject's interstitial fluid may be analyzed for "normal" concentrations within that particular subject. The sample may be analyzed by providing an electrical signal to the sensor at 206 and measuring an electrical property at the sensor that has been generated in response to the electrical signal at 208. The measured electrical property may then be correlated to the biological condition at 210. In some embodiments, the subject's normal healthy baseline behavior may already be known and programmed into the system 10. After the baseline has been established, the subject may continue to be monitored with the system 10 by using the same steps of 206, 208 and 210 until an abnormality, such as an increase or decrease in the concentration of the targeted bio-molecule, is detected by the system at 212.

Once the abnormality has been detected, a signal may be generated at 214 and may be communicated to the controller 14, at which point, at 216, the controller 14 may decide to either continue monitoring, at which point, the method returns to 206, or may decide signal the device 12 to deliver a material from a cavity within the device 12 to the substance at 218, after which the method may return to 206. The subject may be continued to be monitored so that the material's efficacy and compliance may be monitored. In addition, the controller 14 may signal the device 12 to expose another sensor to the substance to detect any secondary effects that are created by the abnormality. If it is determined that the abnormality has disappeared, the system 10 may be configured to stop delivering the material. The subject may then be monitored with the system for possible relapse of the abnormality. Upon the detection that there has been a relapse, the material may be delivered to the subject once again, or another material may be supplied, and the subject may continue to be monitored. At any time, if it is determined that the monitoring should cease, the method may end at 222. In particular, if at 212 it is determined that there is no abnormality, the controller 14 may continue to signal to provide an electrical signal to the same or another sensor on the device 12 at 220, or the controller 14 may stop providing signals to the sensor and the method may end at 222.

The time interval of the monitoring described above may be variable, or may be set at predetermined intervals, ranging for minutes to weeks. The sensors within the cells 18 of the device 12 may be configured to detect concentrations of the targeted biomolecule in a wide range of about 1 pg/dl (trace amount) to about 1 g/dl (concentrated amount).

The devices 12 may be configured to be placed on many tissue locations on the subject's body, including exterior and interior locations. For example, exterior locations may include the skin on the subject's arms, legs, neck, hands, feet, and face. Examples of interior locations include the subject's mouth (including cheeks, gums, and tongue), nasal and sinus passageways, throat, ear and eye tissues, etc. By mounting a device to a portion of the eye or the inner ear, information about the central nervous system may be accessed.

The system 10 may also be configured to monitor entire chemical panels for individuals, patients, or populations at risk for disease. In an embodiment, the system may be configured for use with patients needing immediate critical care, patients that are in shock, patients that have suffered some kind of trauma, and even resuscitation of unconscious patients. By applying the device 12 to the patient, a real-time analysis of targeted biomolecules may be conducted to provide additional information about the patient to the caregiver, even if the patient is unable to speak. In embodiments, the system 10 may be configured for monitoring and treatment of chronic critical diseases, providing early detection of disease, and/or monitoring for a response to therapeutic treatment.

Sampling, Analysis and Delivery Device

Figure 2:
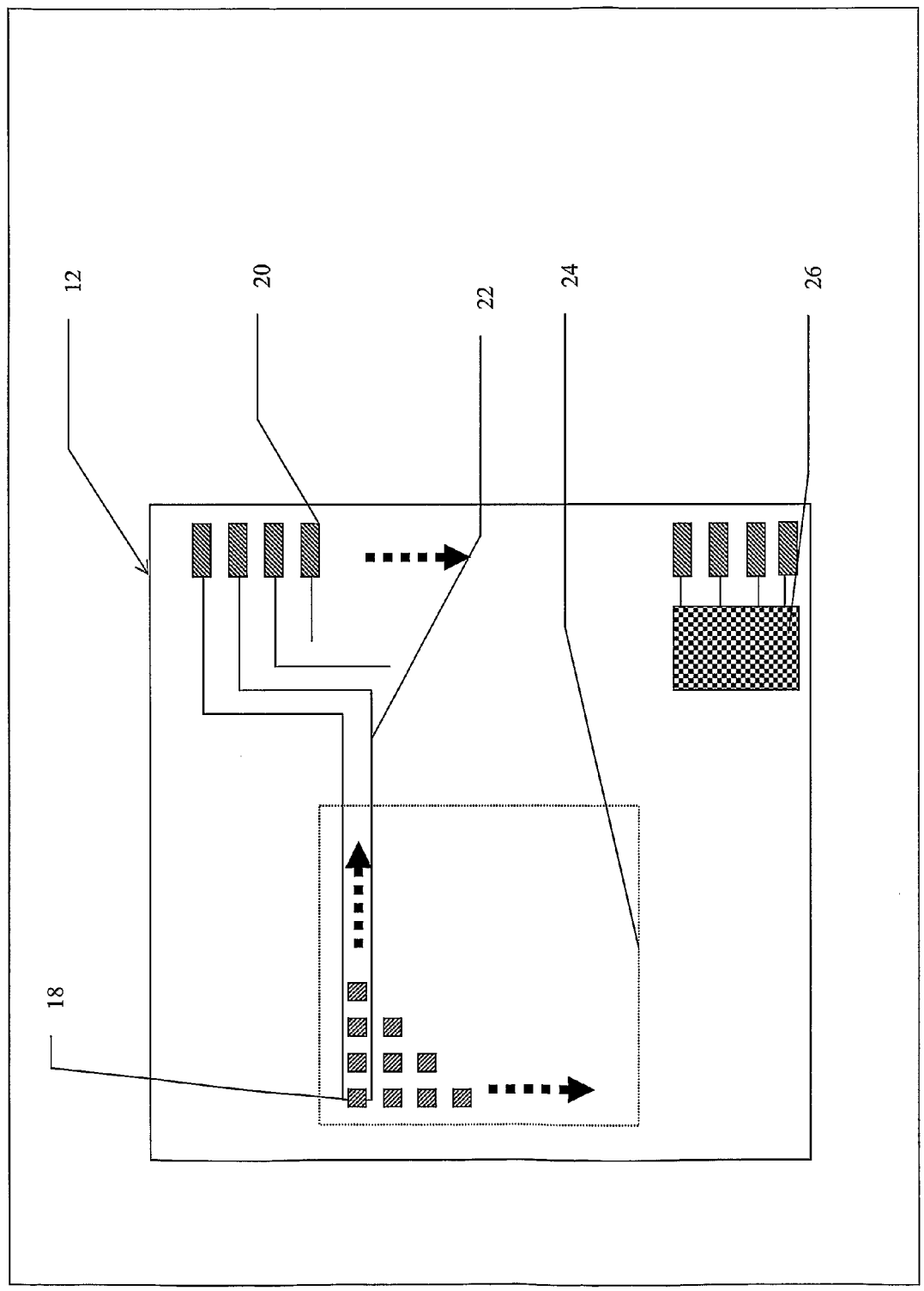
FIG. 2 is a schematic drawing showing an embodiment of functional components of a sampling, analysis and delivery device of the system of FIG. 1.

FIG. 2 is a schematic drawing that illustrates the functional components of the device 12. As illustrated, the device 12 comprises a plurality of sampling, analysis and delivery cells 18. The phrase "sampling, analysis and delivery cell" should not be construed as requiring the cell to provide all three functions in all embodiments. To the contrary, in some embodiments, one cell 18 may be configured to sample the substance and analyze the substance, and one cell 18 may be configured to only sample the substance or only analyze the substance or only provide delivery of a material to the substance. Any combination of these three functions in a single cell is contemplated as being within the scope of the present invention.

In the illustrated embodiment, the cells 18 are arranged in a plurality of columns and rows. Other arrangements are contemplated and the illustrated embodiment is not intended to be limiting in any way. The device 12 also includes a plurality of electrical contact pads 20 that are configured to communicate with the controller 14, and a plurality of electrically conductive paths 22 that connect the cells 18 to the contact pads 20. The cells 18 are located in an area 24 that placed in contact with the sample to be analyzed, such as tissue. The device 12 may optionally include an electrical device identification area 26 that allows the particular device 12 to be identified by the controller 14 when the device 12 is connected thereto.

In an embodiment where biomolecules present in interstitial fluid are to be sampled transdermally, the device 12 is placed in close contact with a subject's skin and held in position by pressure or an adhesive. A precisely predetermined and controlled series of electrical pulses may be applied to one or several pairs of a multiplicity of selectable electrodes, located in the cells 18, so as to produce heat and local electrical fields that disrupt the dead skin cells of the stratum corneum without damaging living cells immediately below them in the viable epidermis. This allows interstitial fluid to flow towards and wet the surface of that point on the device 12 and maintain a concentration in equilibrium with that of underlying tissue for many hours, i.e., until the stratum corneum reforms.

At that precise position where the stratum corneum has been disrupted, one or more pairs of electrochemical electrodes may be positioned and prepared in one of several ways so as to selectively measure one or more properties of the interstitial fluid. These properties include but are not limited to a concentration of biomolecules, such as biochemical analytes, and/or physi-chemical properties such as pH or concentration of a dissolved gas. Such measurements may be continuous in nature and may track any time variation of these concentrations reliably, until the stratum corneum repairs. As discussed in further detail below, the preparation of the electrodes at each cell may include encapsulation to protect reactive surfaces prior to beginning the desired measurement. The encapsulation may be provided by impermeable and reactive, e.g. adhesion, binding, charging, conducting, etc., or selectively permeable membranes that are selected for a variety of applications, depending on the targeted biomolecule.

In an embodiment, the substances containing biological fluids to be analyzed may have already been collected from a variety of samples, including but not limited to food, water, air, whole blood, urine, saliva, chemical reactions, and cultures. In such an embodiment, small volumes of the substance containing the biological fluids may be applied to the surface of the device 12 either statically or by means of a continuous flow across the surface. The controller 14 may be configured to open one or several selective sensing cells 18 and begin monitoring specific concentrations of the biological fluids. For example, blood draws can be analyzed immediately at the point of care, or air and water samples can be monitored continuously for chemical and biological contaminant-free purity. In addition, the cells 18 can be replaced as they are used-up or as new contaminant threats are identified, by opening new cells 18 in place thereof. The system 10 is configurable to provide an application specific analysis and monitoring system.

Sampling

Figure 3:
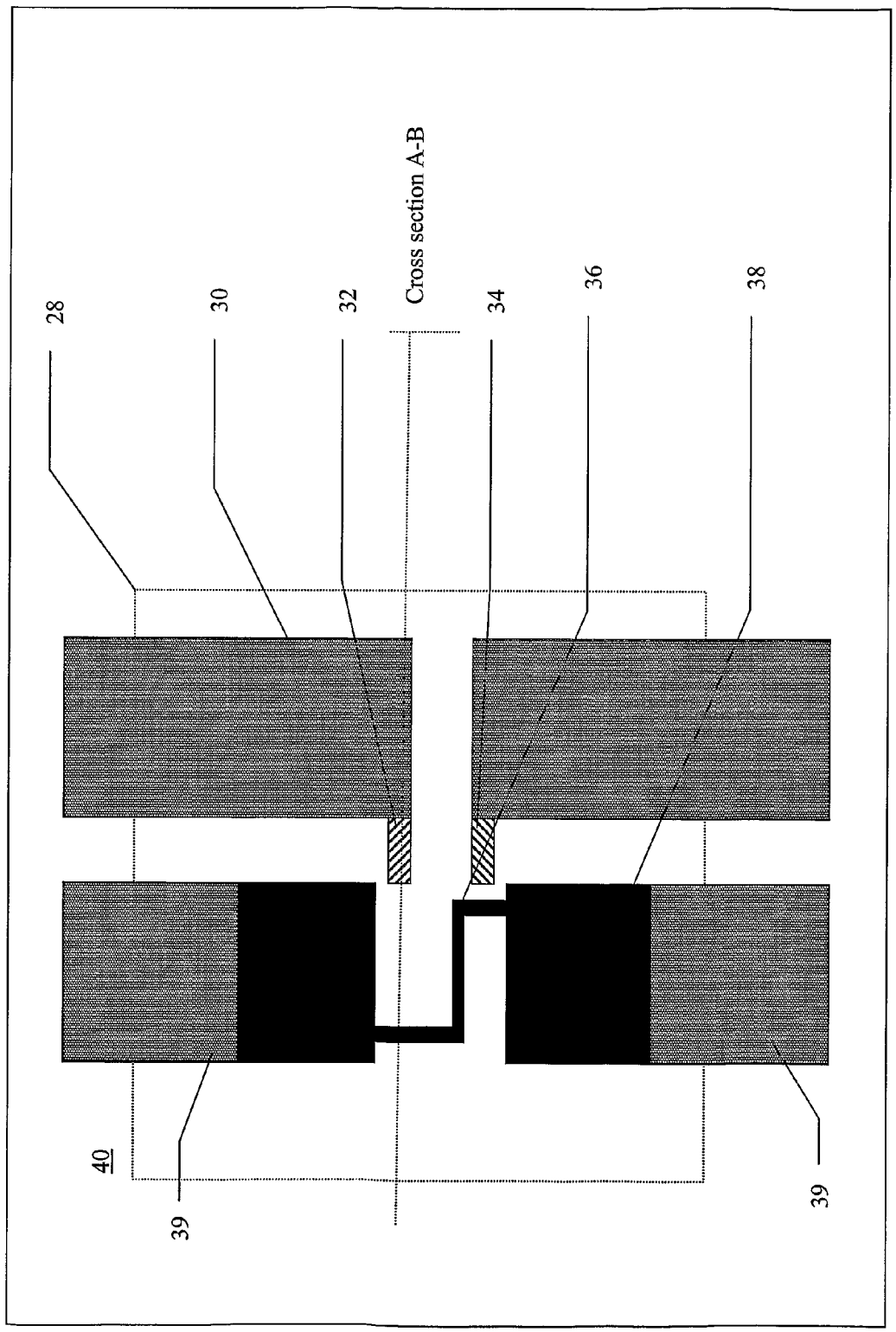
FIG. 3 is a schematic top view of part of a geometry of a sampling, analysis and delivery cell according to an embodiment of the invention.

FIG. 3 is a schematic top view of part of an embodiment of a single cell 18 that may be one of many on the device 12. In this embodiment, the cell 18 is configured for sampling, analysis and delivery, and components for both sampling and analysis are exposed on the surface of a compliant substrate 40. For applications in which the device 12 is attached to a non-flat surface, the substrate may be flexible so that the device 12 may conform to the surface of the non-flat surface. A buried encapsulation, or cavity 28 that may contain a material for delivery is shown in outline. Electrically conductive paths 30 that are ultimately connected to the electrically conductive paths shown in FIG. 2 are covered by a thin insulating layer and form part of a selective working electrode 32 and a reference electrode 34. As shown in FIG. 3, an exposed electrically resistive element portion 36 joins exposed sections 38 of other electrically conductive paths 39.

FIG. 4A is a schematic top view of an embodiment of the sampling and analysis cell 18. In this layout, the selective working electrode 32 and the reference electrode 34 are joined by the exposed section of electrically conductive paths 38 of a second conductive path so that the disruption of the stratum corneum and chronoamperometric or other electrical property analytical measurements can be made by the same electrodes 32, 34.

Figure 5:
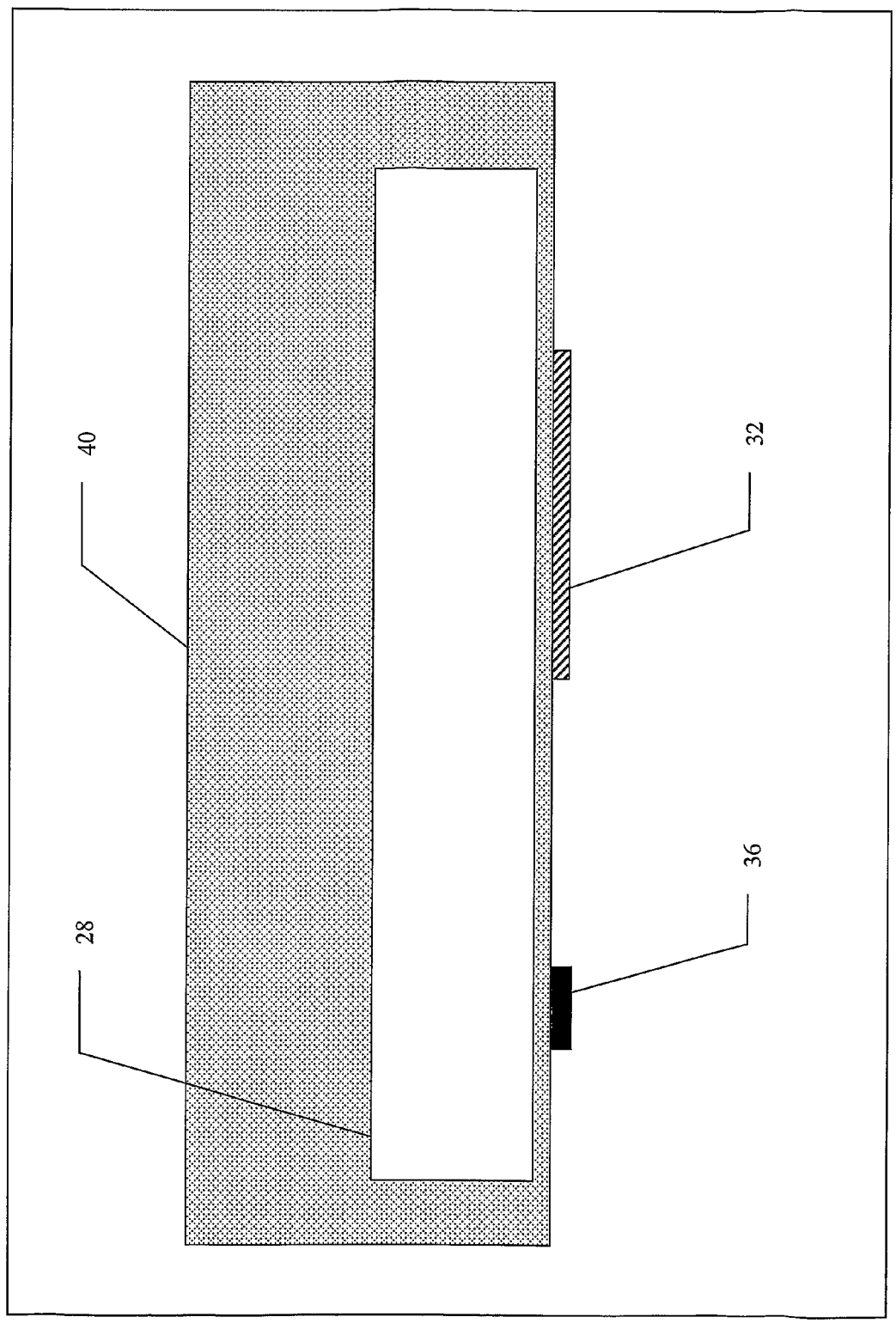
FIG. 5 shows a cross section along A-B of the embodiment of FIG. 3.

FIG. 5 shows a cross section along A-B of the embodiment of FIG. 3. The cross-section shows the resistive element 36 in proximity to an analysis electrode that may be the selective working electrode 32 on a portion of the flexible substrate 40.

Figure 6:
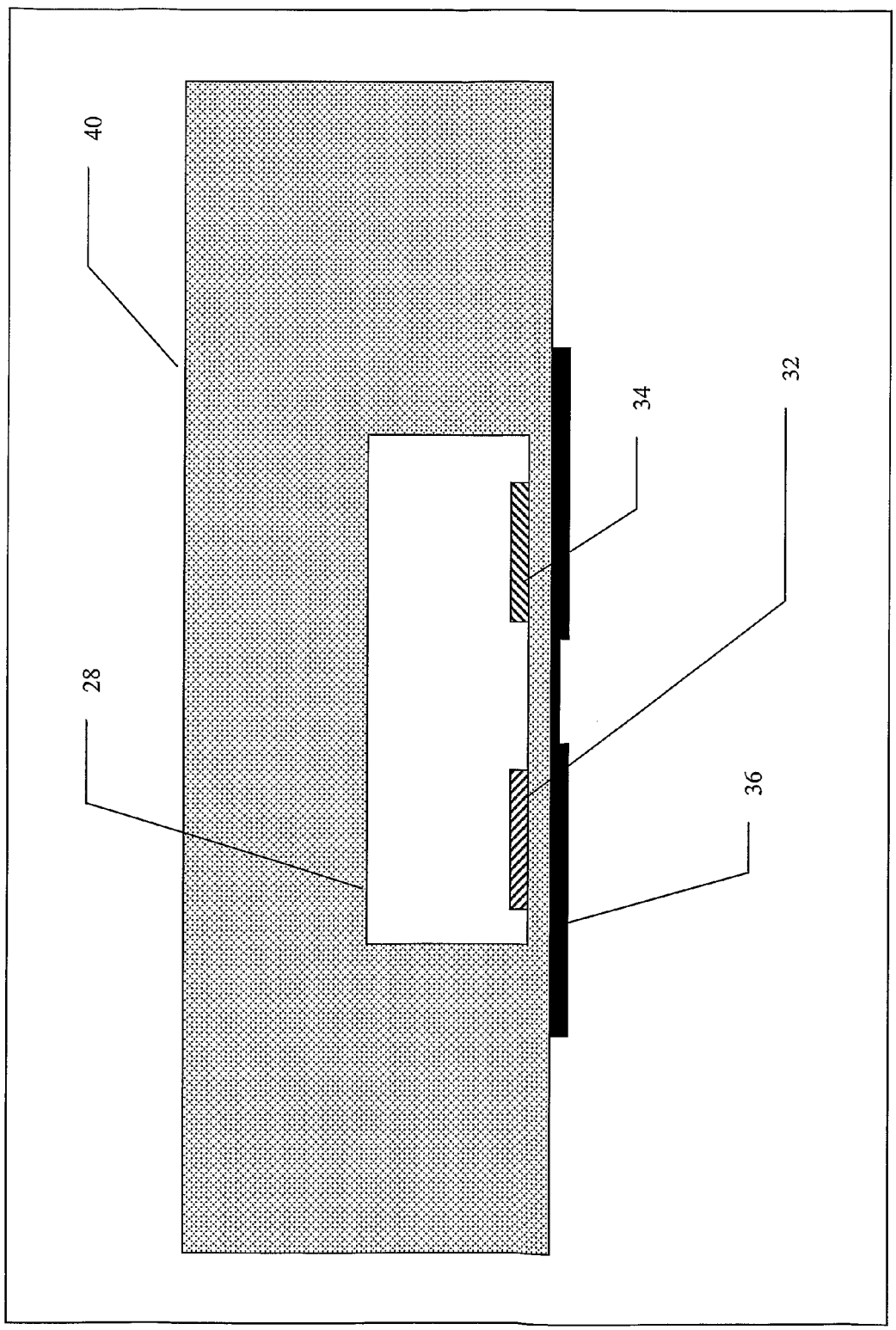
FIG. 6 is a schematic cross section of a variation of the design depicted in FIG. 3.

FIG. 6 is a schematic cross section of a variation of the design depicted in FIG. 3 in which the analysis electrodes 32 and 34 are encapsulated within a cavity in the substrate 40 and are on a thin membrane of substrate material at the point of sampling. The cavity 28 may be filled with material to be delivered to the sampling site, or the cavity 28 may be empty.

Figure 7:
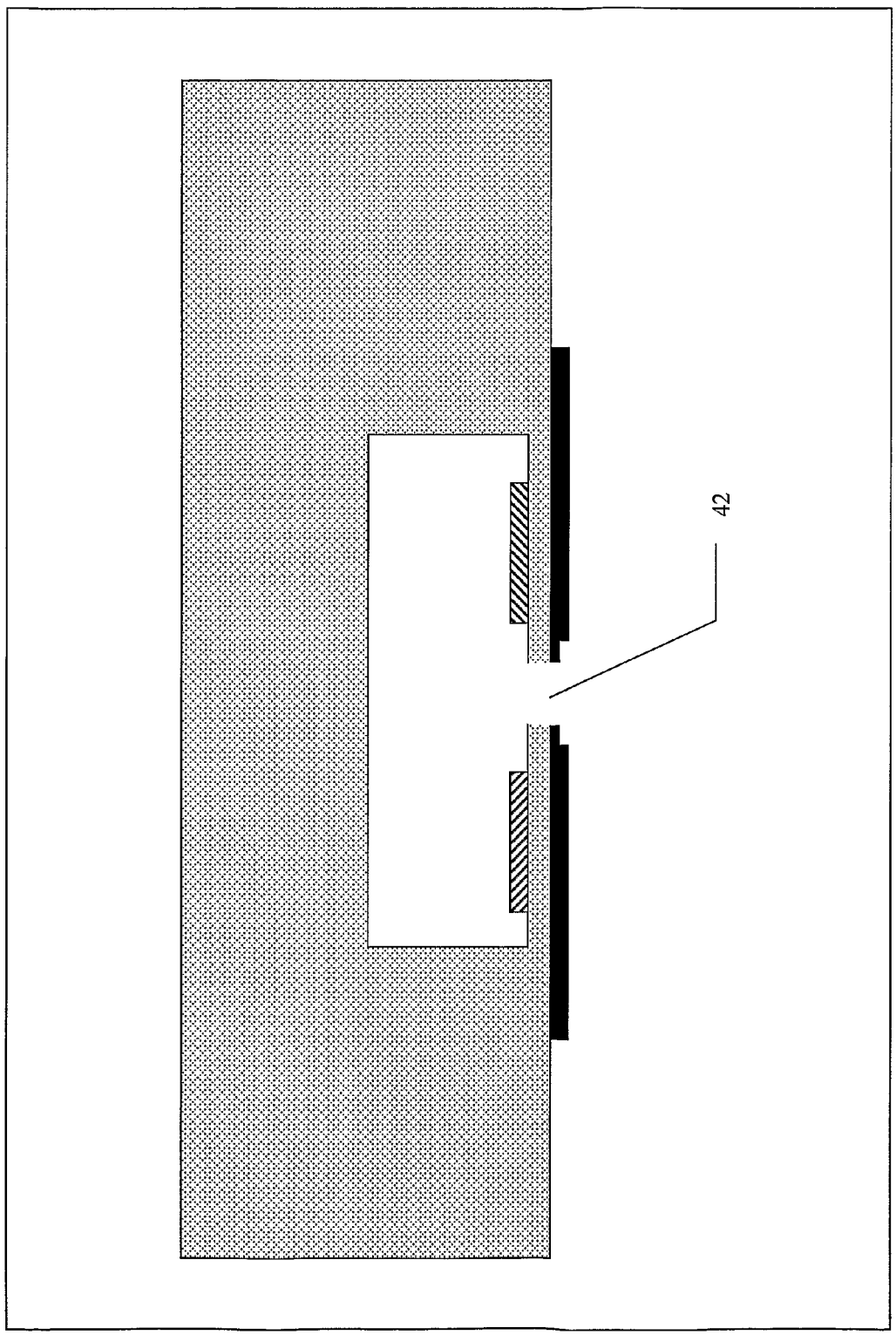
FIG. 7 shows the same cross section as FIG. 6 with a breach in a thin membrane of substrate.

FIG. 7 shows the same cross section as FIG. 6 in which a breach 42 in the thin membrane of substrate has been caused by the actuation of the resistive element. This breach 42 results in the exposure of the analysis electrodes 32, 34 to the substance to be analyzed, and also allows for delivery of any encapsulated delivery material from the cavity 28 to the sampling site.

Disruption

Figure 11:
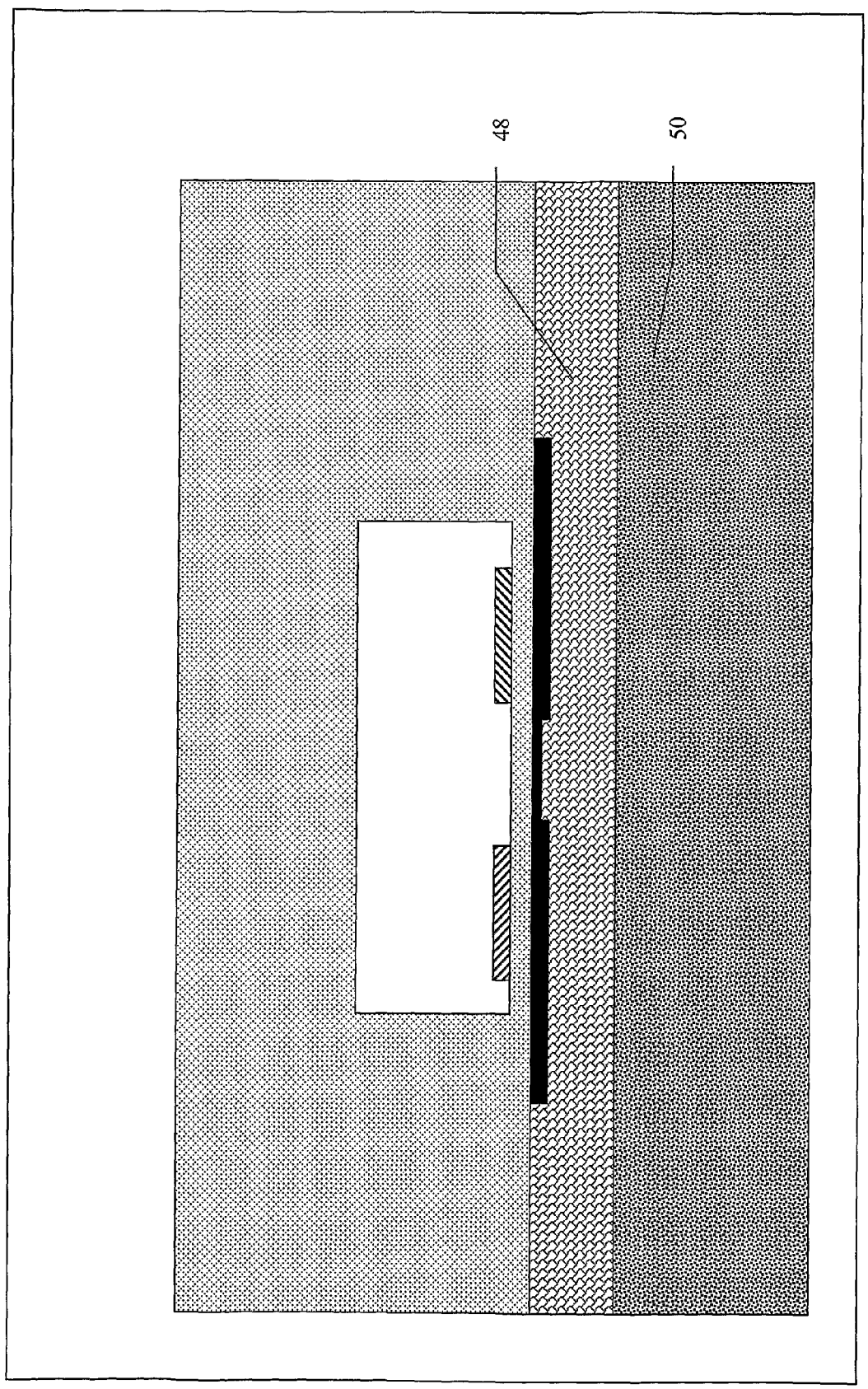
FIG. 11 shows the cell of FIG. 6 in contact with tissue such as skin which is simplified to show schematically the scaly stratum corneum and the viable epidermal tissue.

In one of several analytic uses, the device 12 is adhesively held in contact with skin, or some other tissue or membrane on the target subject. FIG. 11 shows the cell of FIG. 6 in contact with tissue such as skin, which is simplified to show schematically the scaly stratum corneum 48 and the viable epidermal tissue 50 below in which is located interstitial fluid.

In an embodiment, the subject's stratum corneum may then be disrupted by applying a series of voltage pulses of approximately 2V lasting less than a second. The exact sequence and voltage required must be adjusted for the particular subject and the location and nature of the tissue to be disrupted. The heat and voltage drop between the sample electrodes does not remove the dead cells of the stratum corneum but severs connections between them, thereby creating capillary openings that serve to wick the interstitial fluid from the viable epidermis up to sample electrodes and allow sufficient fluid transfer to equilibrate and dynamically maintain equilibrium with interstitial fluid in the viable tissues beneath the stratum corneum.

Disruption of barrier tissues is different from prior art in which processes such as ablation and poration through mechanical means (e.g. a needle) are typically used. Ablation refers to the removal of certain targeted cells. Barrier cells are often not living cells, and are sometime scaly and flattened from their living shapes, are closely and conformally packed, and adhere to one another by chemical bonds between the biomolecules constituting cell walls. The process of disruption refers to the process by which the bonds between the packed barrier cells are gradually broken, allowing narrow capillary openings to form between cells. The cells themselves mostly remain intact. At one point as the capillary size increases, there are conductive paths through which interstitial fluid can be drawn to the surface. Our observation is that the rate and nature of flow is independent of, for example, basal metabolic blood pressure and there is no internal pressure head forcing interstitial fluid outwards. Interstitial fluid flow can be enhanced with special hydrophilic surface treatments of the sampling points on the sampling device as well as in capillary structures or tiny enclosures patterned into the surface if the sampling device.

This unique technique for reliable disruption of barrier tissues includes a particular sequence and combination of pulses of electrical energy on the individually addressed sampling electrodes. In particular, for human forearm skin, one or multiple conducting thin film resistors between the sampling electrodes have been used. For multiple resistors, the values of the resistances are chosen to cascade from a high (e.g. 200 Ohm) to medium to low resistance (50 Ohm). The size of each resistor is comparable to that of the barrier cell to be dislodged from its neighbors. For 50 micron stratum corneum cells, this means that the gap between electrodes should be less than 100 microns. Electrical voltage steps from 0 to 2 V may be applied to the electrodes in short bursts of less than one second, typically with 0.2V increases in each pulse. The device may be fabricated such that the conductive traces leading from the connector to the electrodes to are buried except at the resistors.

In an embodiment, a moderate electric field of up to 4 MV/m may be applied. Then, by 2.2V, the temperature of the least resistive element may reach 140° C. very briefly, and the resistor may then open. The opening is determined by the precise fabrication materials, dimensions and sequences of the resistor and the underlying sampling device material (often a low melting temperature polymer film such as poly ethylenes or methacrylates). With material deformation, the conductive trace breaks. Heat profile measurements show that the temperature may fall to less than 80° C. across a 50 micron thick stratum corneum. If there is only one resistor, the electrode goes into open circuit, yet an electric field can still be applied in pulses between the electrodes. For multiple resistors, the voltage steps may continue until all resistors break to open circuit. The electrodes may now be left alone to allow for electrochemical measurements between sensing and reference electrodes.

In an embodiment in which it is desirable to ablate the cells rather than disrupt the cells, a heater may be provided on the surface of the device. The heater may be configured so that, for example, a 50 mJ pulse of thermal energy may be applied to the stratum corneum cells so as to ablate the cells. Such an arrangement is described in, for example, U.S. Pat. No. 6,887, 202, which is incorporated herein by reference.

Figure 12:
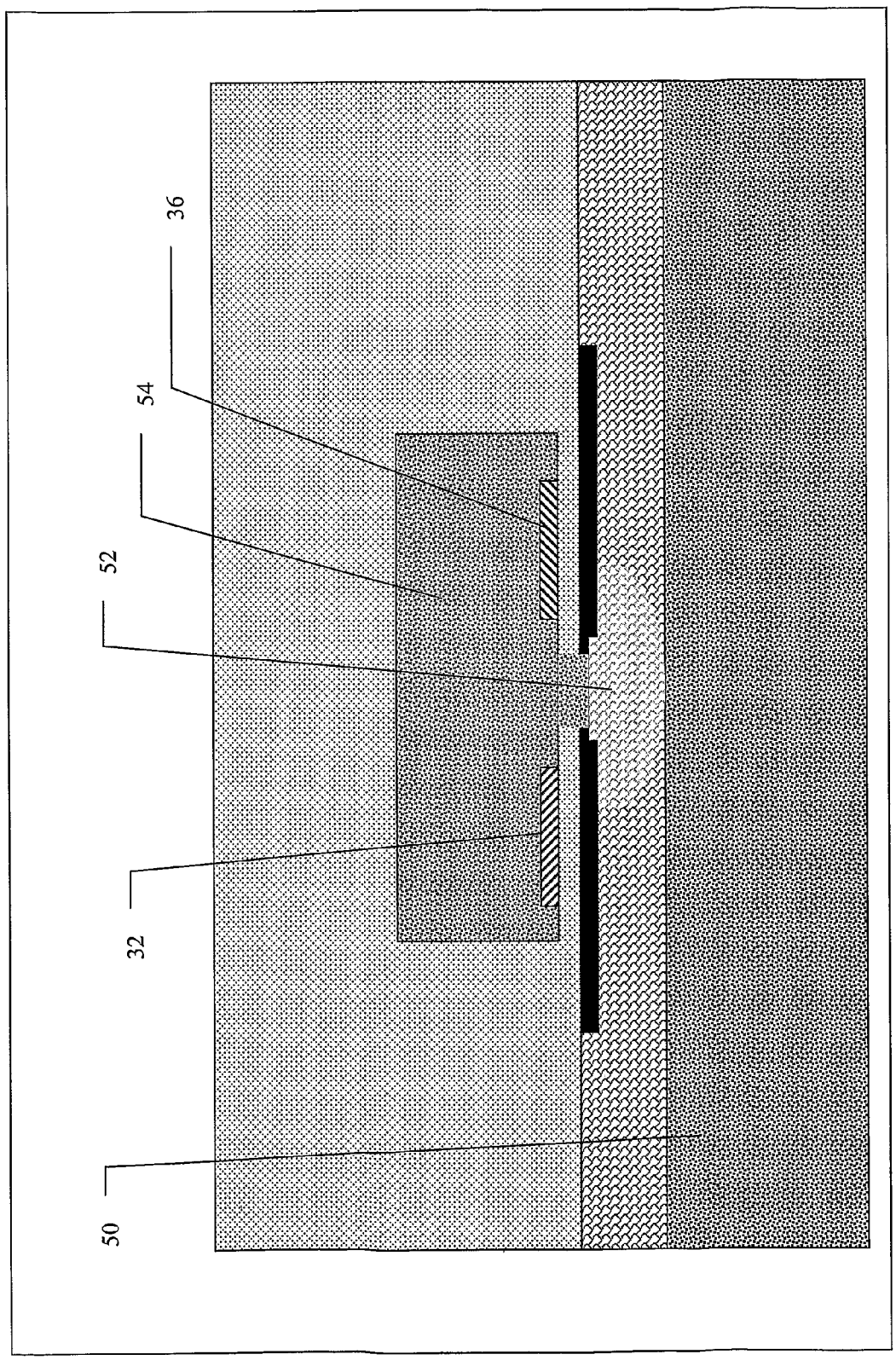
FIG. 12 is a schematic drawing showing the cell of FIG. 11 after disruption of the barrier tissue.

FIG. 12 is a schematic drawing showing the cell of FIG. 11 after disruption of the barrier tissue in region 52. A percolating fluid path is established allowing the interstitial fluid 54 from the viable epidermal tissue 50 to flow by capillary force to and wet the sampling site. The interstitial fluid 54 that is wetting the electrodes may be analyzed by the selective electrodes 32 and 34, as discussed below.

In an embodiment, the disrupting electrodes themselves may be used for the electrochemical measurements, which may provide compact economical fabrication, higher packing densities, and simplification of connection and control circuitry.

In some applications, particularly applications in which the substance to be sampled is already located at a top surface of the targeted subject, the device may not even include a mechanism for disrupting cells.

Analysis

In an embodiment of the invention, two sample electrodes are supported by the substrate 40 and are joined by a resistive element. An electro-conducting enzyme anchor layer covers part of at least one of the sample electrodes, and a protective layer may cover the entire device, except for the vicinity of the sample electrodes.

In embodiments directed to analyzing interstitial fluid, any target biomolecule in the interstitial fluid drawn into the vicinity of the electro-conducting enzyme anchor layer interacts with the anchored enzyme. This interaction may be detected by, for example, chronoamperometric measurements made using voltages applied across the sample electrodes. Of course, the electrodes may be configured so that other types of electrical properties, such as resistance, capacitance, etc. may be measured.

Figure 9:
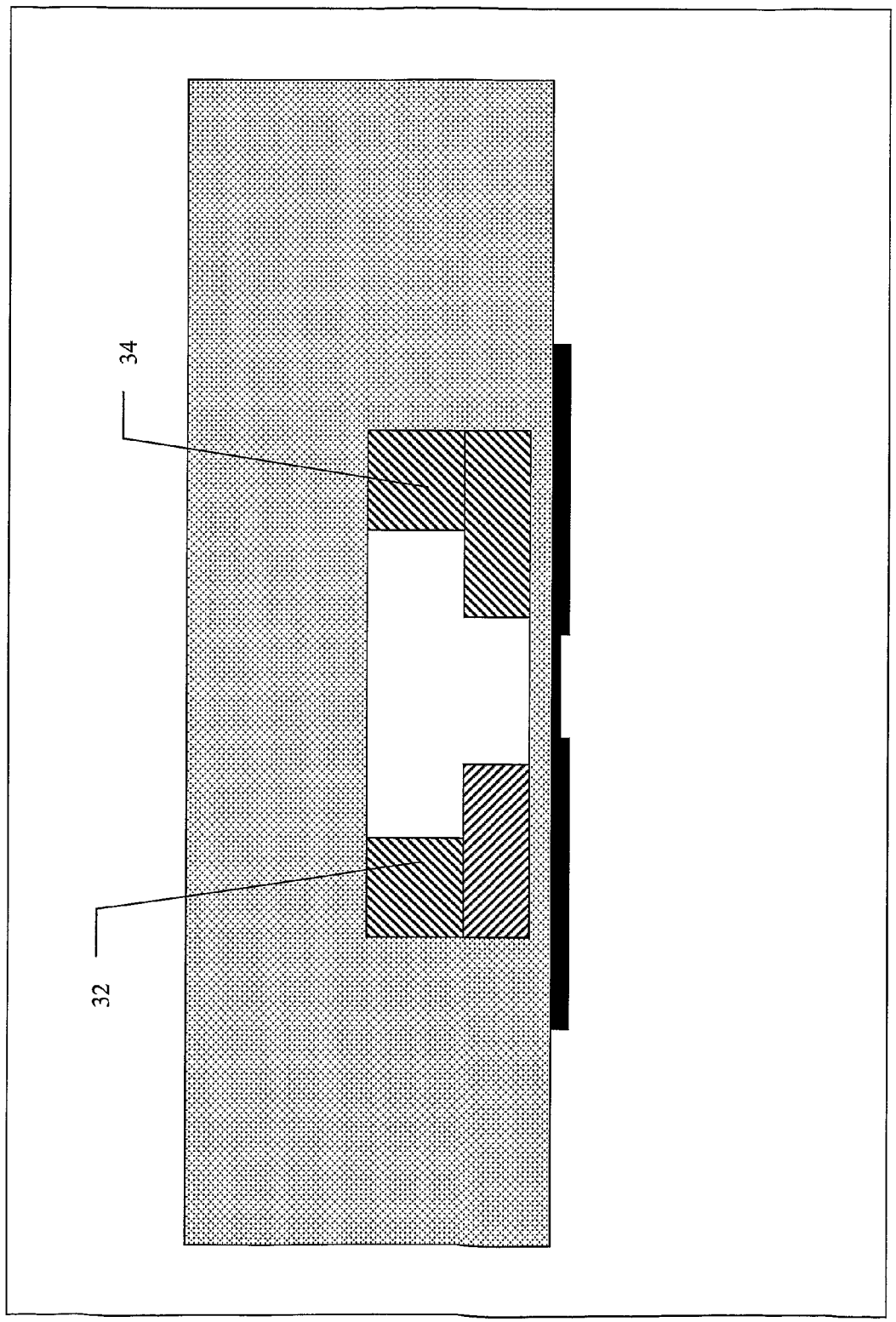
FIG. 9 shows the cross section of FIG. 6 in which the effective surface areas of analysis electrodes is increased.

FIG. 9 shows the cross section of FIG. 6 in which the effective surface areas of the analysis electrodes 32 and 36 is increased to achieve a corresponding increase in electrical signal and a lessening of the signal to noise ratio. An increase in the area can be achieved both by covering additional area on the walls of the cavity as well as by using a protected spongy porous electrode material.

Figure 10:
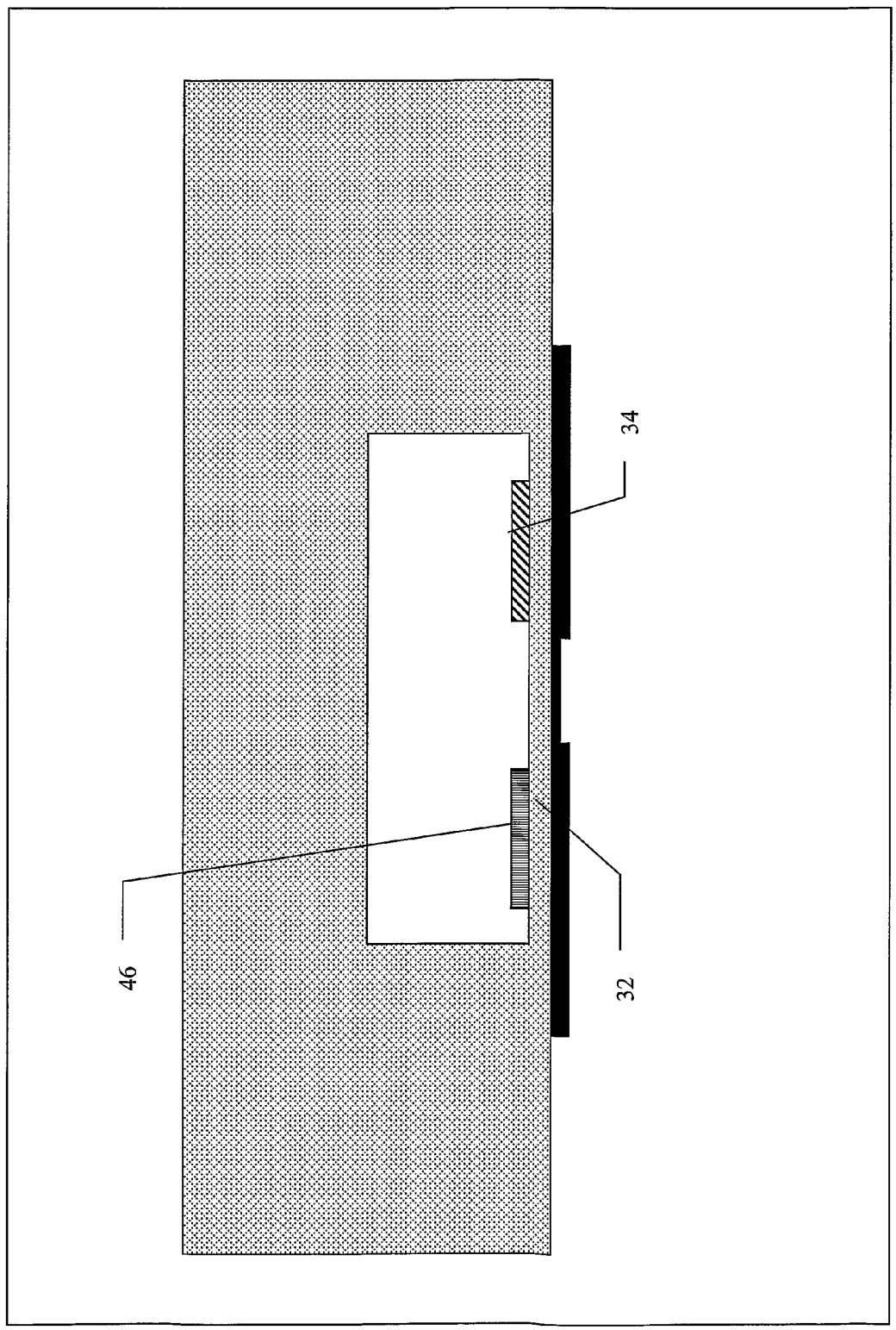
FIG. 10 shows the cross section of FIG. 6 in which the effective surface areas of the analysis electrodes is increased.

FIG. 10 shows the cross section of FIG. 6 in which the effective surface areas of the analysis electrodes 32 and 34 is increased achieving a corresponding increase in electrical signal and a lessening of the signal to noise ratio. Increase in the area can be achieved by covering the working electrode 32 surface with a protected dense nanomaterial 46 prepared with the desired selective chemistries. The preparation of such nanomaterials is discussed in greater detail below.

Figure 15:
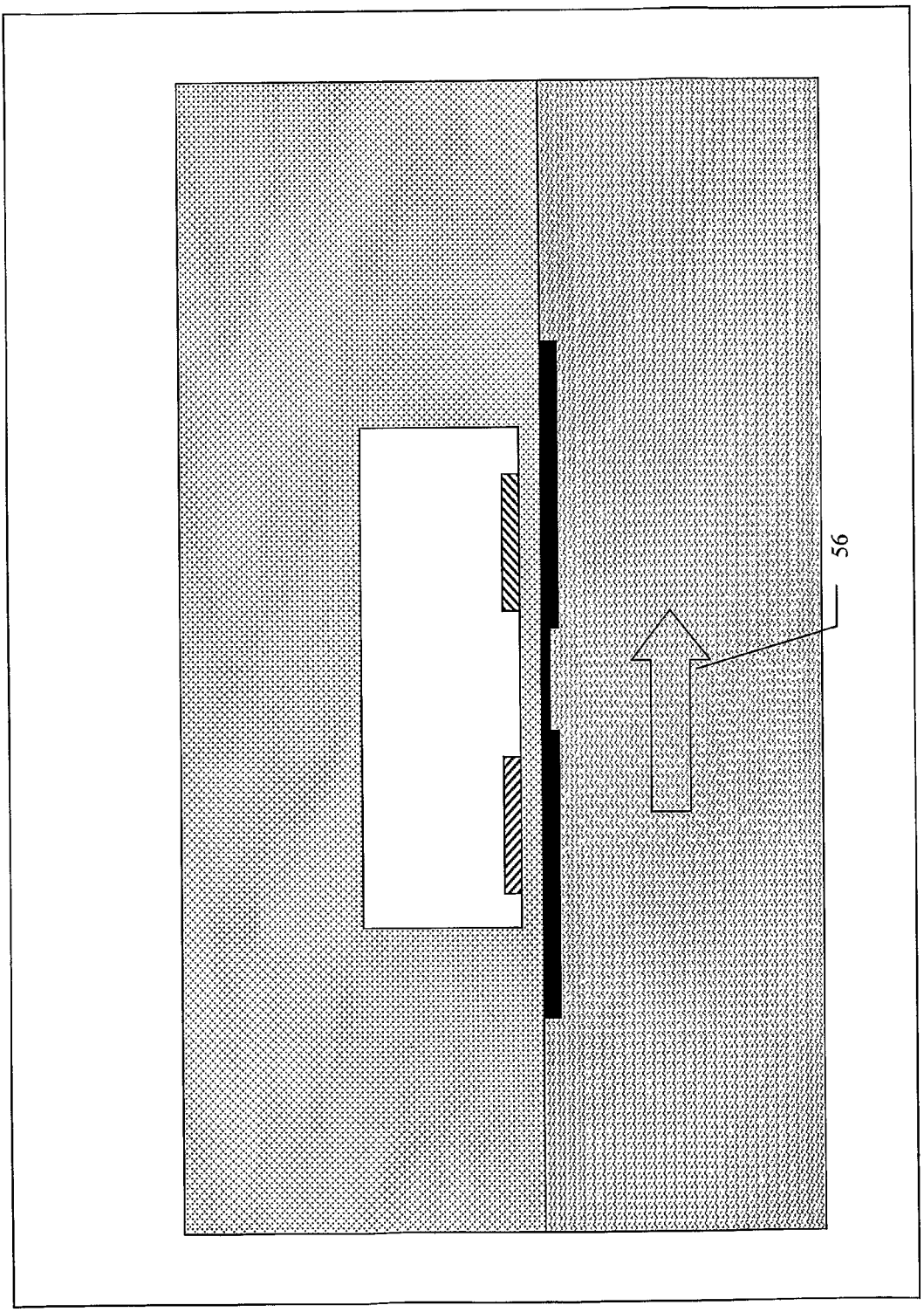
FIG. 15 shows the cell used for sampling fluids.
Figure 16:
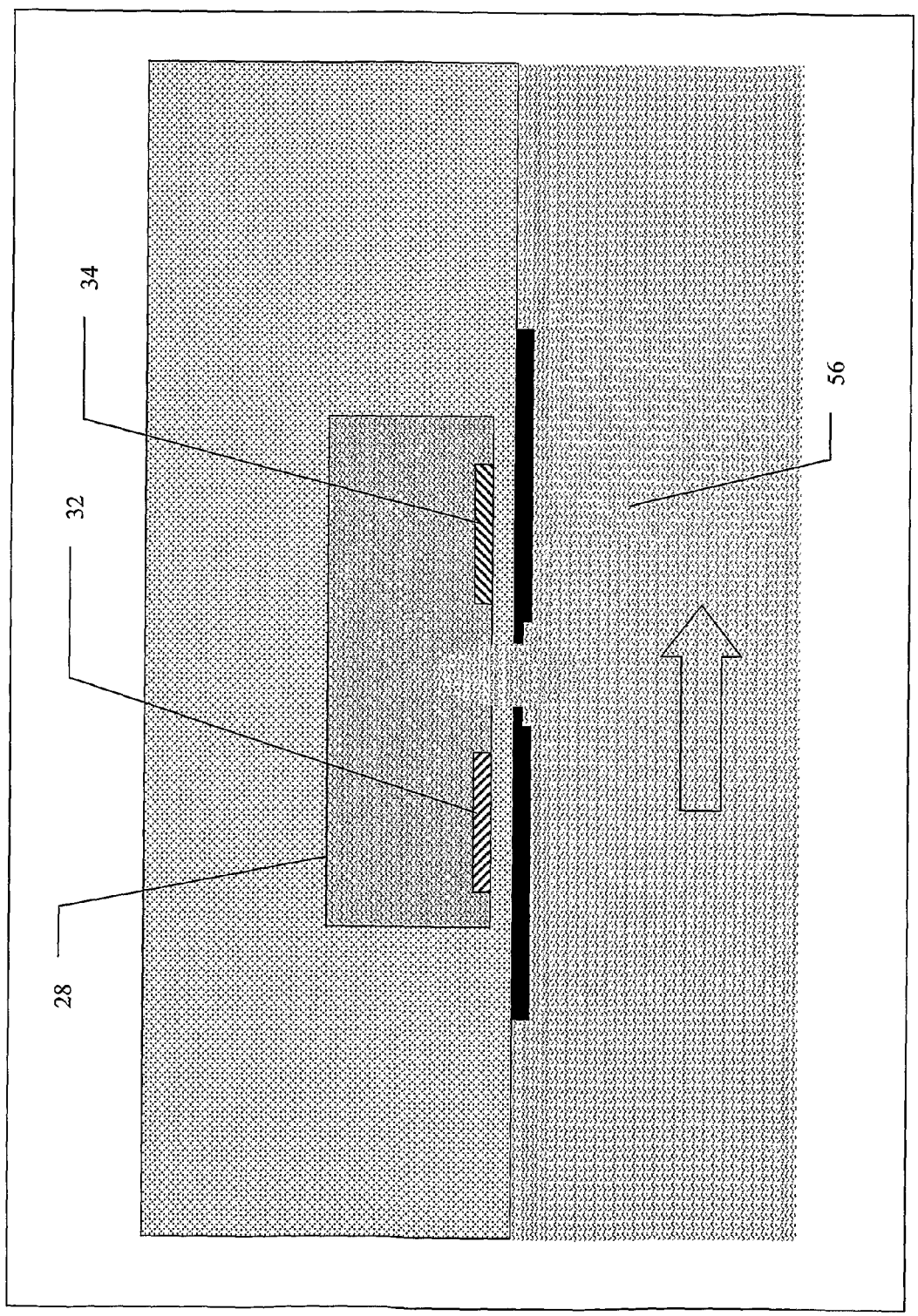
FIG. 16 showing the cell of FIG. 15 which has opened to allow fluid to enter the cavity where the analysis electrodes are located.

FIG. 15 shows the cell used for sampling fluids that are not located on an opposite side of a protective membrane. The cell of FIG. 6 is in direct contact with stagnant or flowing fluid 56 to be analyzed. FIG. 16 shows the cell of FIG. 15 which has opened to allow fluid to enter the cavity 28 where the analysis electrodes 32 and 34 are located. Once the electrodes 32 and 34 are exposed to the fluid and voltage is applied to the electrodes, a resulting electrical property may be measured.

Figure 17:
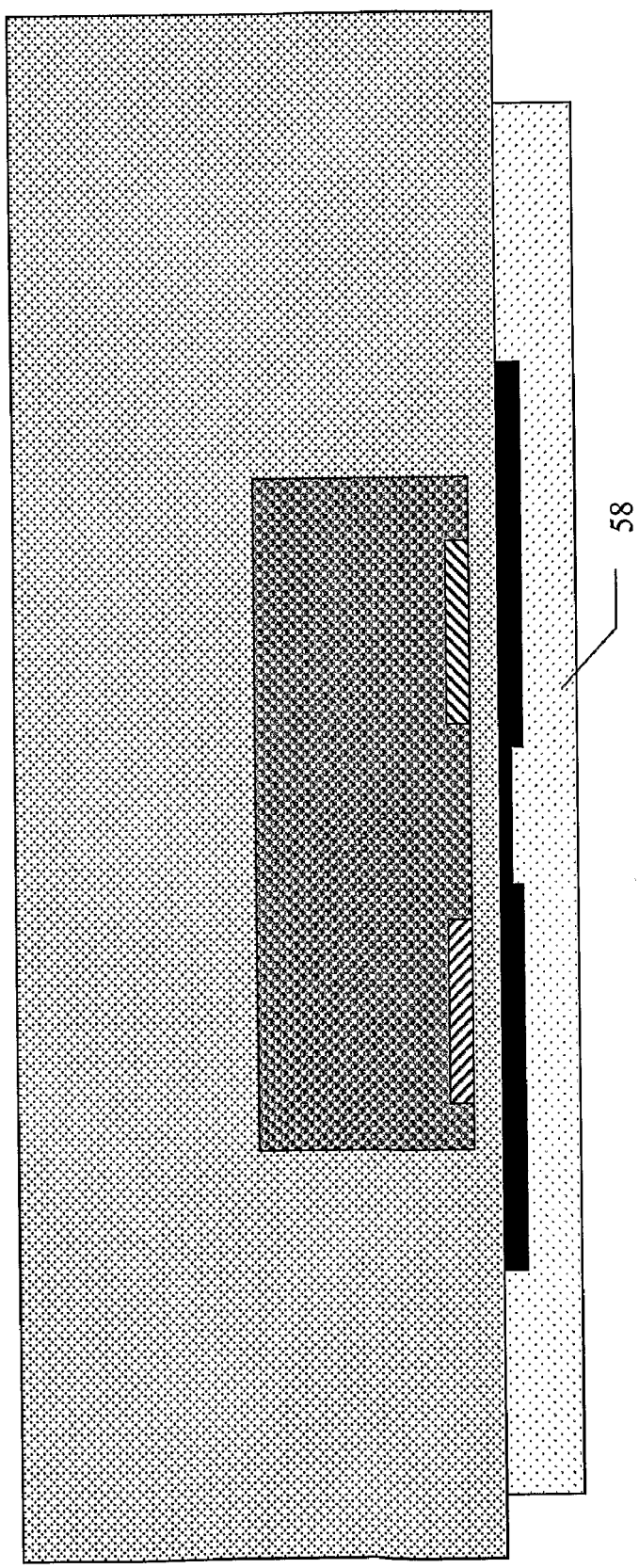
FIG. 17 shows the cells used for sampling solids or powders.
Figure 18:
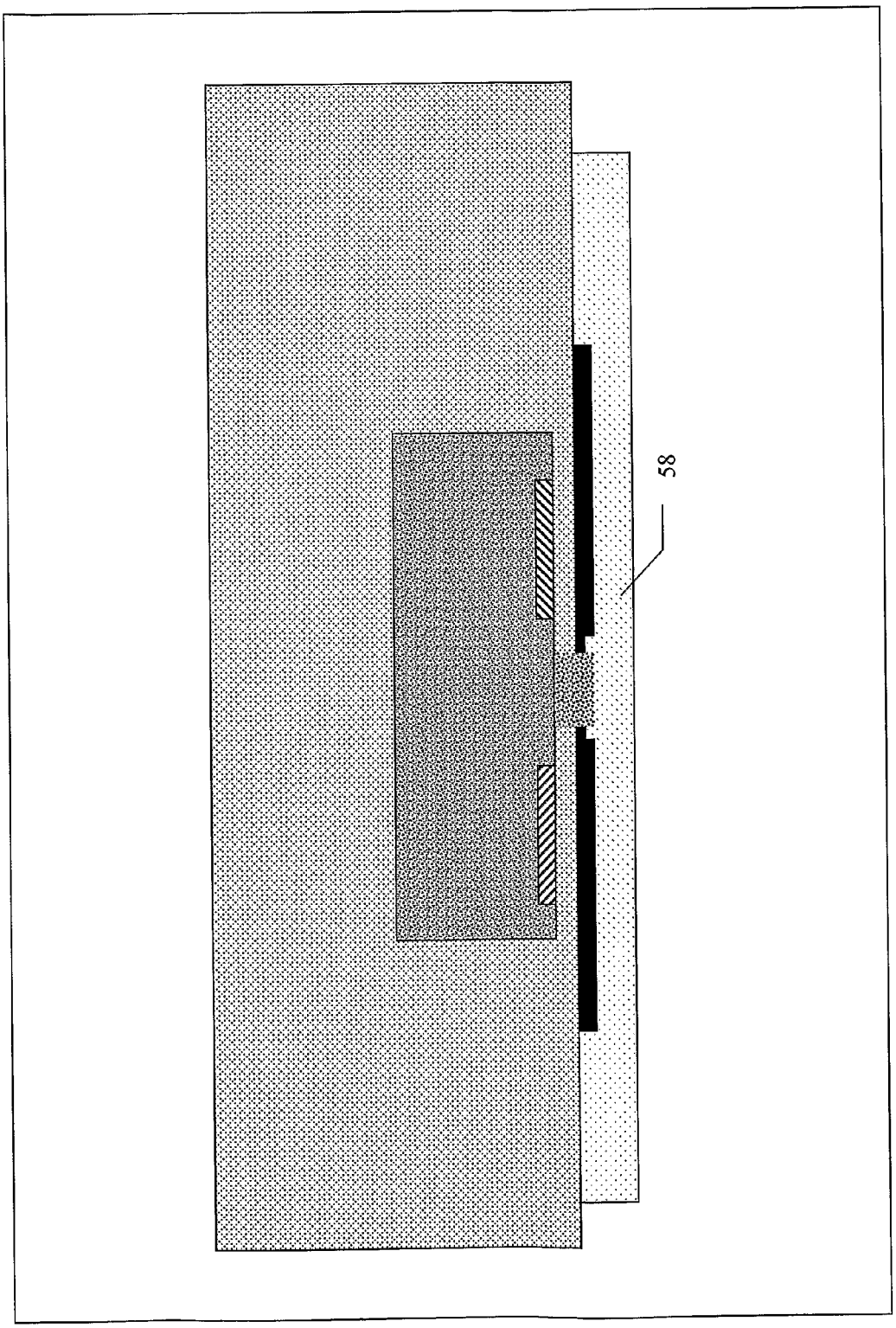
FIG. 18 shows the cell of FIG. 17 which has opened to allow contained fluid to wet and dissolve the dry sample enabling a concentration to be present at the analysis electrodes.

FIG. 17 shows the cells used for sampling solids or powders. The cell of FIG. 8 onto which the dry sample 58 to be analyzed has been applied or collected. FIG. 18 shows the cell of FIG. 17 which has opened to allow contained fluid to wet and dissolve the dry sample 58, thereby enabling a concentration to be present at the analysis electrodes.

The illustrated embodiments of the above-described cells and electrodes are not intended to be limiting in any way but are instead intended to provide examples of possible configurations.

For example, in embodiments where it is desired to measure a concentration of gas, including but not limited to oxygen, carbon dioxide, carbon monoxide (deleterious), and nitrous oxide, dissolved in a biofluid, such as interstitial fluid, the device 12 may be configured as follows. In an embodiment, the device 12 may be placed onto a body to obtain access to interstitial fluid. In another embodiment, the device 12 may be placed in the subject's lung ventilation pathway, such as in or near a nasal passage, in such a way to expose the device 12 to inhaled and exhaled air, thereby allowing for gas component measurements to be performed.

There are numerous ways in which the sensing electrodes of the device 12 may be made sensitive to the selective, accurate measurement of these gases, such as those described in U.S. Pat. Nos. 6,270,651 and 7,001,495, and United States Application Publication No. 20010052459, the entire contents of which are all hereby incorporated by reference. The sensing electrodes of the device 12 may be prepared with thin films of specific metals and electrolytes that when exposed to gas selectively produce electrochemical voltages in proportion to the logarithm of the partial gas pressure. Some of the electrolyte materials that may be used are slightly soluble in water and may be protected by thin films of polymer coating that are hydrophobic, but allow gas molecules to permeate and pass through the layer and reach the sensing electrodes, as indicated by layer 58 in FIG. 18.

In another method to detect gases such as oxygen blood gas, the sensing electrodes of the device 12 may be joined by a thin semiconducting polycrystalline layer of a material, such as tin oxide or indium tin oxide. Oxygen from the interstitial fluid or exhaled air may be absorbed into the polycrystalline semiconductor material and modify its electrical conductivity between the electrodes, depending on the gas partial pressure. In addition, thin films of semiconductors or insulators (including polymers) may be used that selectively adsorb the gas molecule of interest, and the amount of adsorption may be measured electrically as a change in electrical capacitance between the electrodes 32, 34 in the cell 18 of the device 12.

In an embodiment of the invention, piezoelectric detection devices may be created in the cavities 28 of the device 12 to allow for detection of Antibody-Antigen, or Ab-Ag. Ab-Ag detection may be facilitated by monitoring shifts in resonant frequency that accompanies a binding event. In an embodiment, the piezoelectric devices include cantilever beams and membrane structures that incorporate piezoelectric materials to detect an analyte binding with its specific receptor. For the cantilever beams, two modes of sensing may used. First, when a binding event occurs, the surface stress that results may be measured by measuring the voltage generated by the stressed piezoelectric film. Second, a shift in the cantilever beam's resonant frequency as a result of the change in mass due to the binding event may be detected. For membrane structures incorporating a piezoelectric material, Ab-Ag complexation may be determined by measuring the resonant frequency shift.

In an embodiment, the device may implement piezoelectric films within the device structure to generate an electrical current that can be stored on a capacitive element. The device may be worn on the body (forearm, wrist, hip etc) where natural body movement causes a bending motion in the patch. By employing piezoelectric elements, any bending stress can be transduced into electrical energy. The ability for a solid to convert mechanical stress into an electrical signal, and back, is based on a non-uniform charge distribution within the solid. Although the whole material remains neutral, there are many internal dipole moments that can create a detectable internal potential. This electrical signal is maximized when the piezoelectric material first undergoes a polarization process known as poling. Before the poling process, dipoles are distributed randomly throughout the solid, however, when poled by an external electric field and temperature, the dipoles re-orients the internal dipoles to be in an ordered and near-aligned state. A mechanical compression decreases the magnitude of the dipole moment, thus reducing the voltage while stretching increases the magnitude of the dipole moment and increases the voltage signal.

In a like manner, an applied voltage with the same polarity as the piezo-material stretches the material, while an applied voltage of opposite polarity compresses the material. In one configuration of the device, a layer of a polymeric piezoelectric material like polyvinylidene difluoride, or PVDF is incorporated in or deposited onto the substrate. One use of the device is to measure the potential and use it as a measure of the deformation of the sampling device. The second independent and non-conflicting use involves the control and communications devices 14, 16. The potential generates current that the controller 14 may rectify and use to charge either a capacitance or the on-board rechargeable flexible polymer lithium batteries.

Delivery

Figure 4B:
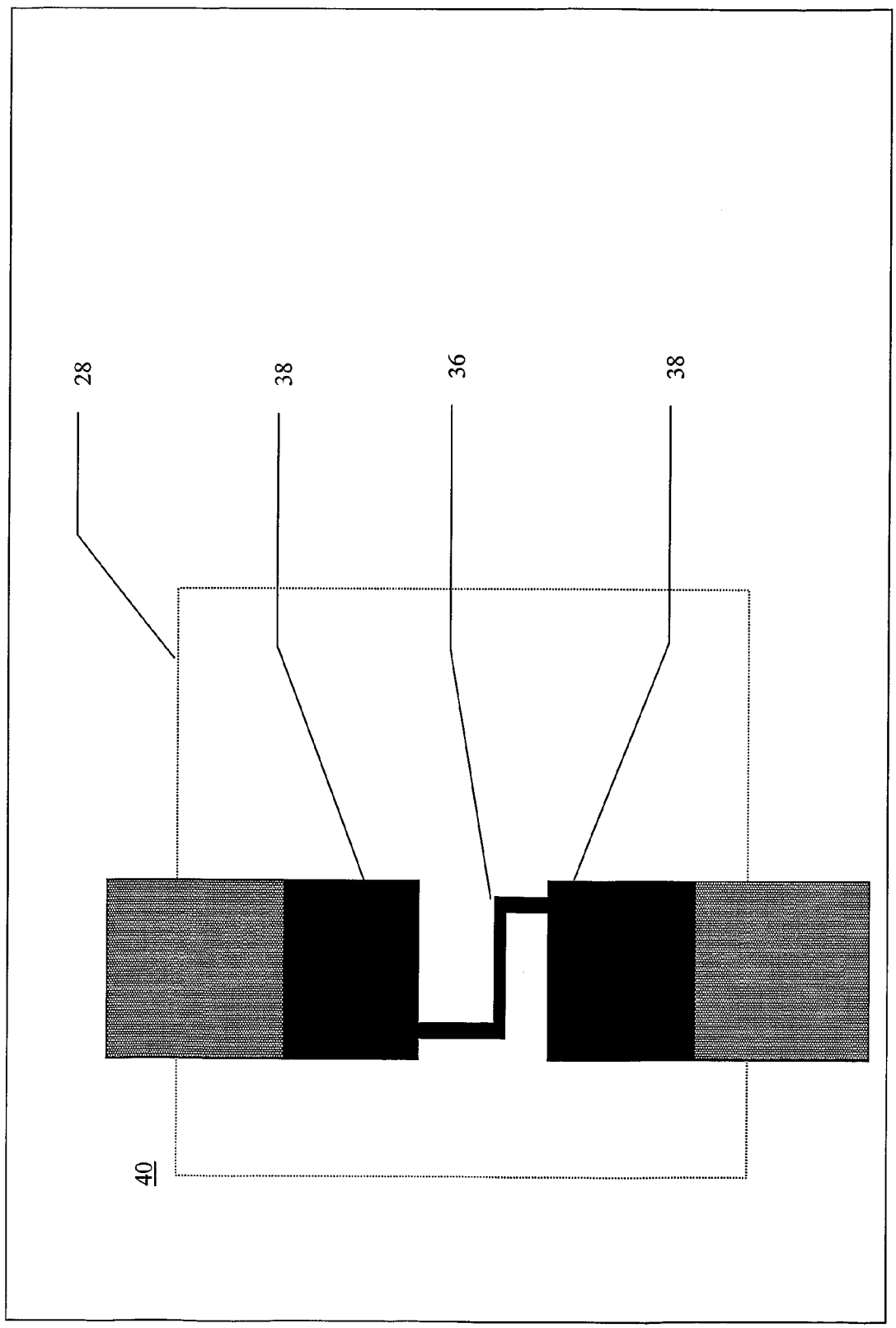
FIG. 4B is a schematic top view a geometry of a delivery cell according to an embodiment of the invention.

FIG. 4B is a schematic top view an embodiment of a cell 18 that is configured to delivery a material to the substance. In this layout, the buried encapsulation or cavity 28 that contains material for delivery is located behind a pair of exposed sections 38 of electrically conducting paths joined by an exposed resistive element portion of the conduction path. In this way, disruption of the stratum corneum may be used to also provide delivery of the material in the buried encapsulation 28 to the interstitial fluid. The material may be in the form of a gas, liquid or solid, and may include drugs, chemicals, cells, biochemicals, biomolecules, proteins, peptides, genetic material, etc.

Figure 4C:
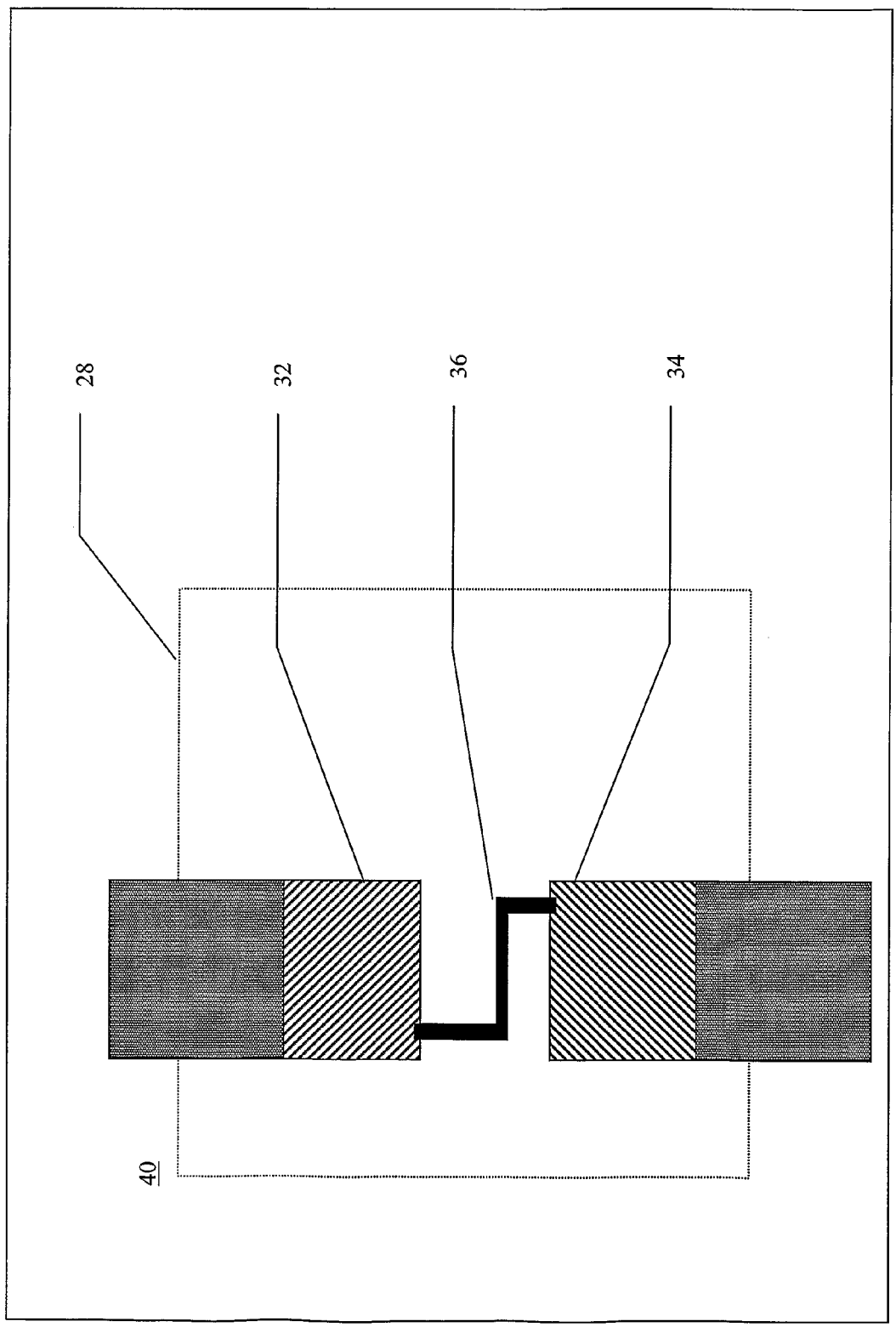
FIG. 4C is a schematic top view of an embodiment geometry a sampling, analysis, and delivery cell.

FIG. 4C shows a top view schematic of one part of another embodiment of a cell 18 that may be one of many on the device 12. In this embodiment, both sampling and analysis devices are exposed on the surface of the compliant substrate 40 and the electrodes 32, 34 are located at the exposed portions of the electrically conductive paths, thereby resulting in fewer conductive paths, which may result in the need for increased control functionality.

In separate multiple encapsulations at the point of measurement, biochemicals in gas phase, dry powder or aqueous solution may be stored and released by controlled diffusion through encapsulating wall materials or through sequential controlled rupture of portions of the encapsulating wall so as to allow desired concentrations of the chemical to dissolve into the interstitial fluid and gain access to the body through the locally disrupted stratum corneum. As an analytical chemistry tool, the chemical can be chosen to react and modify the composition of the local interstitial fluid, and reaction products may be measured by the multiple electrodes. Alternatively, the encapsulated chemical sample may be a calibration standard. Separately, the selected or newly selected measuring electrodes can be used to follow continuously the subject's response to the administered chemical, thus efficacy can be quantified and adapted to the individual and adverse reactions safely detected and prevented at the lowest of doses.

Figure 8:
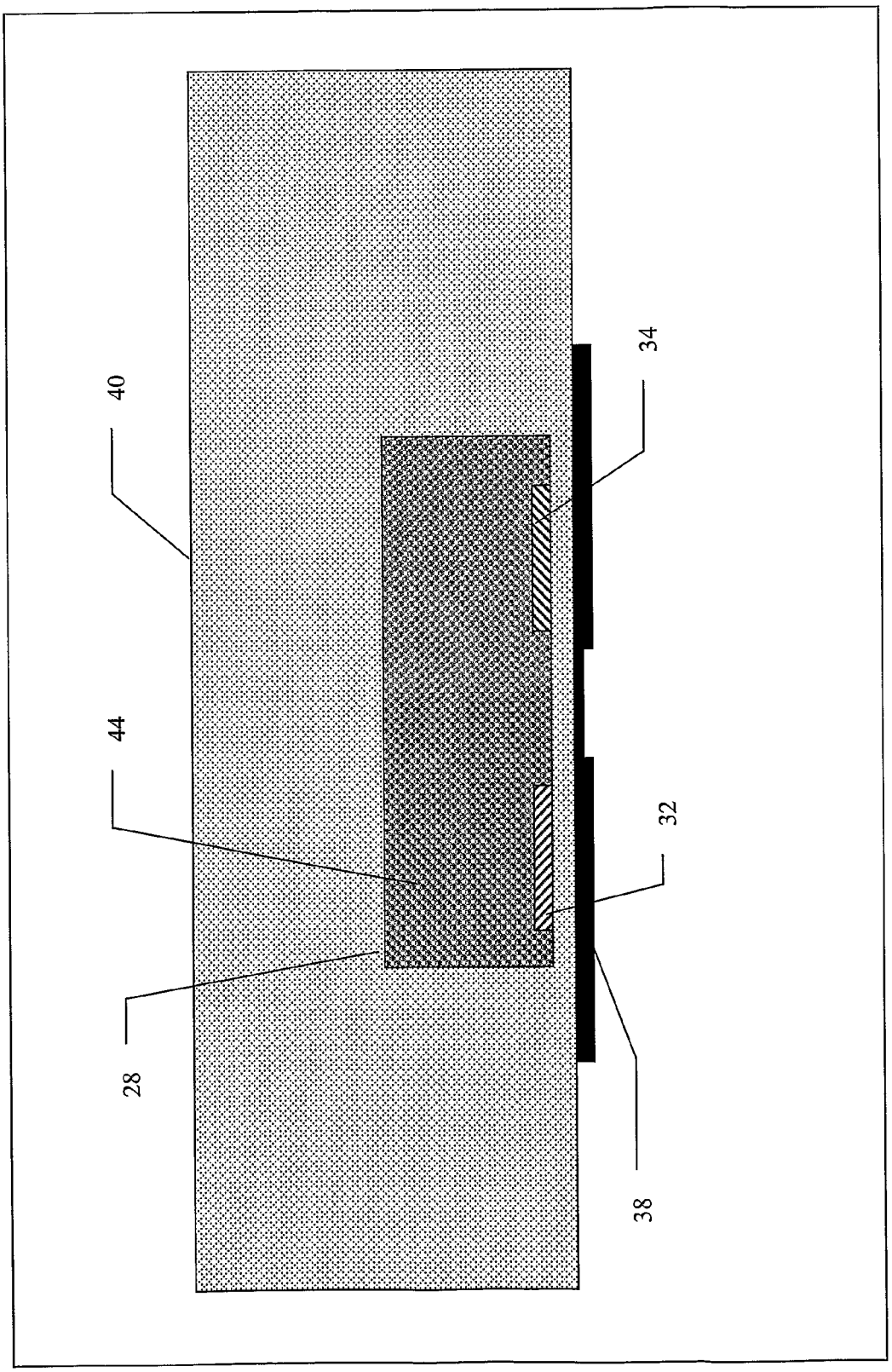
FIG. 8 shows the cross section of FIG. 6 with a cavity filled with material for delivery at the sample site.

FIG. 8 shows the cross section of FIG. 6 with the cavity 28 filled with a material 44 for delivery at the sample site. Embodiments of how the cavity may be filled are discussed in greater detail below. The working electrodes 32 and 34 may be configured to set the concentration of the delivery material 44 and, hence, gauge how much of the material is left the cavity and how much has been delivered to the sampling site.

Figure 13:
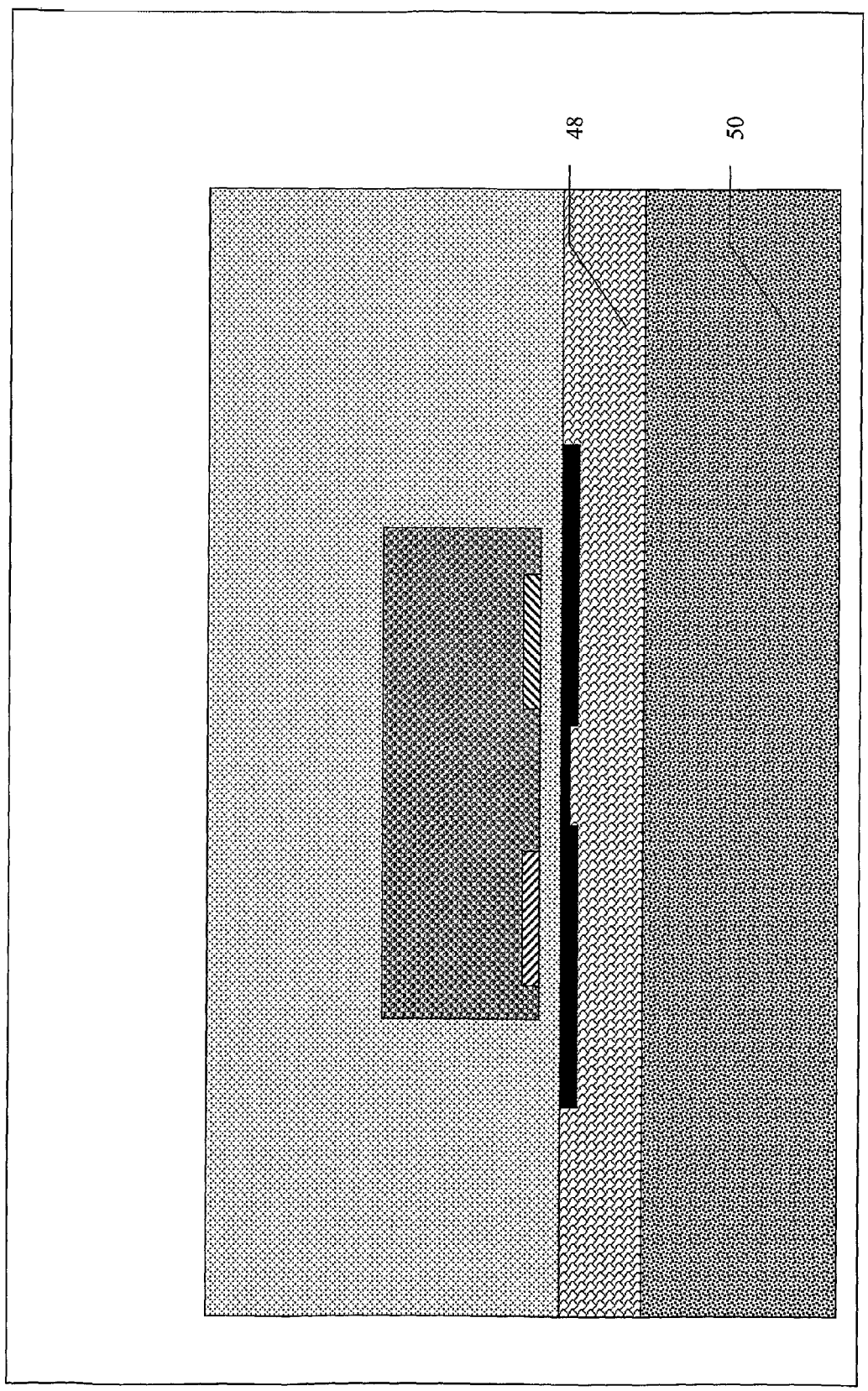
FIG. 13 shows the cell of FIG. 8 in contact with tissue.

FIG. 13 shows the cell of FIG. 8 in contact with tissue, such as skin, which is simplified to show schematically the scaly stratum corneum 48 and the viable epidermal tissue 50 below in which is located interstitial fluid.

Figure 14:
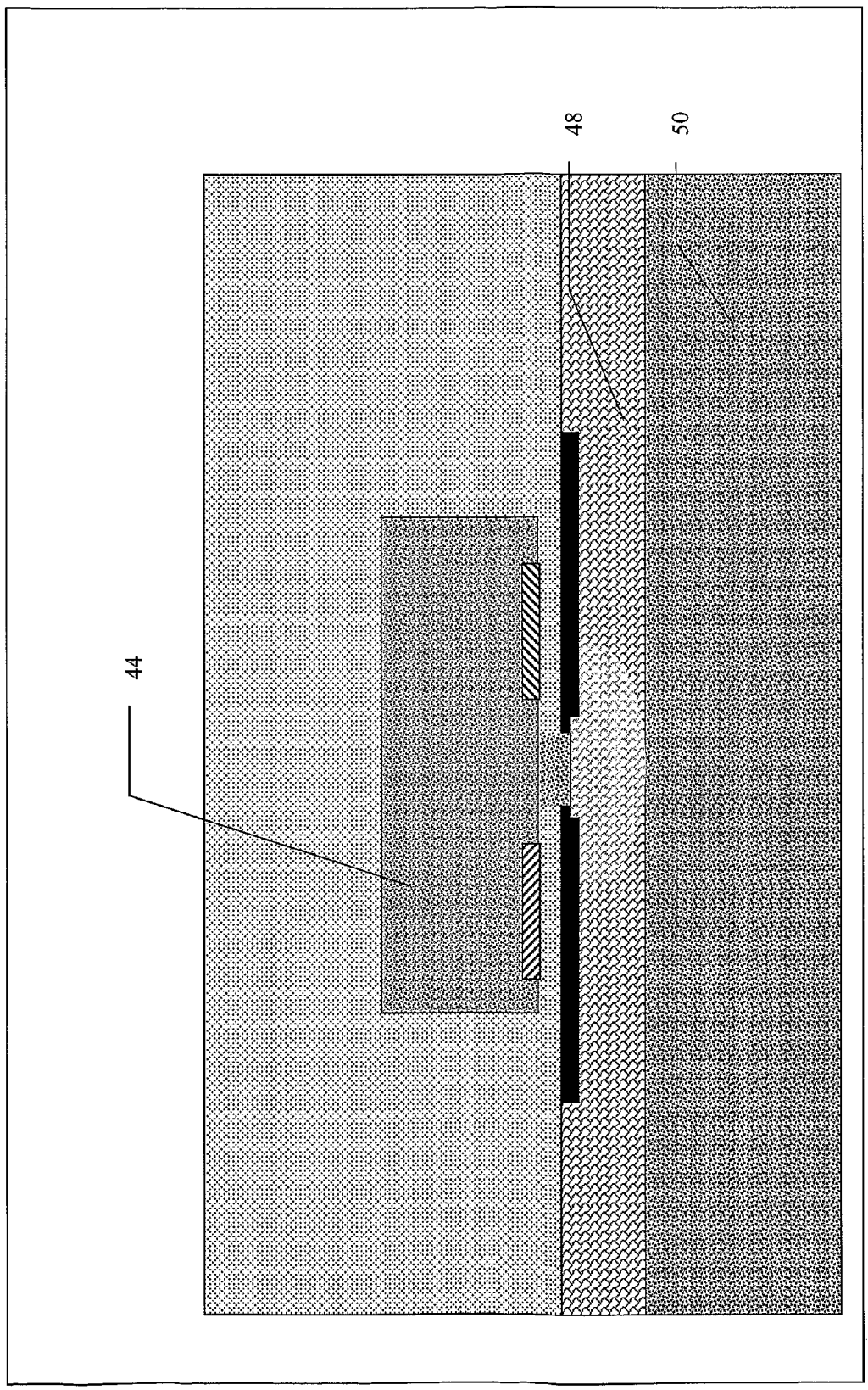
FIG. 14 shows a schematic view of the cell of FIG. 11 after disruption of the barrier tissue.

FIG. 14 shows a schematic view of the cell of FIG. 13 after disruption of the barrier tissue and the thin membrane that seals the cavity 28. A percolating fluid path is established, thereby allowing the interstitial fluid 54 to flow by capillary force to and wet the sampling site. The delivery material 44 mixes or dissolves in the interstitial fluid and due to the resulting high concentration gradient diffuses backward through the disrupted stratum corneum 48 to the viable tissues 50 and thence to the rest of the body.

By scaling the individual sampling site on the device 12 to a dimension of 10 micrometers or less, the intracellular fluid of individual cells can be analyzed by disrupting the cell membrane locally, and a therapeutic material can be injected into the cell before releasing it from the sampler surface.

As described above, in an embodiment, the disruption of the thin membrane that seals the cavity may be provided by the heat created by the electrodes and/or resistive element that provides disruption of the stratum corneum. In such an embodiment, the rupturing of thin membrane is essentially provided by melting the thin membrane to a point where a breach in the membrane occurs, so as to create a thermal fusion rupture. In another embodiment, the thin membrane of the cavity may be ruptured by mechanical forces that are applied to the thin membrane so as to burst, tear, and/or shear, the membrane. Such mechanical forces may be created by, for example, creating bubbles within the cavity via electrolysis with the electrodes that are located within the cavity. The pressure within the cavity due to the bubble formation may become high enough to burst the thin membrane and allow the material 44 that is encapsulated in the cavity 28 to flow out of the cavity 28 at the location of the rupture. Such examples of rupturing the thin membrane to create a flow path for the material to exit the cavity or for the substance to enter the cavity should not be considered to be limiting in any way.

Fabrication

During fabrication, the electro-conducting layer on the electrode 32 may be electrochemically activated with an anchored enzyme that modifies a target biomolecule. For instance, if glucose is the target biomolecule, the enzyme may be, but is not limited to, glucose oxidase, if lactate is the target biomolecule, the enzyme may be lactate oxidase, and if bilirubin is the target biomolecule, the enzyme may be, bilirubin oxidase. In some embodiments, the electro-conducting layer may be electrochemically activated with an antibody. By selectively electrochemically activating the electrodes with specific enzymes and antibodies, different cells 18 located on the same device 12 may be configured for sensing different bio-molecules.

In an embodiment, the device 12 may be a flexible patch-like chip with a multilayer polymeric metal laminate structure and may be fabricated using SU-8 as a structural layer, a Teflon-AF release layer, polymethylmethacrylate (PMMA), polypyrrole (PPy) and glucose oxidase (GOD). For brevity we shall describe a particular embodiment of the device in which, for clarity, the encapsulation and protective membrane rupture features are absent, and in which we have chosen to combine the electrodes used for disruption of the stratum corneum with the sensing and reference electrochemical electrodes.

In an embodiment, the sampling, analysis and chemical delivery device fabrication process uses SU8 as a principal structural material and generally consists of five steps. This process is a subset of an earlier technology developed for the polymer material polydimethylsiloxane (PDMS). The first step was the deposition of a Teflon release layer on a glass substrate, which allowed the multi-layered multi polymeric devices to be removed easily from the glass after fabrication. A thin layer of SU8 was formed by spin coating and acted as a base layer (10µ) for the rest of the device and provided adhesion to the Teflon. The third step in the fabrication process consisted of spin coating a thick (150µ) SU8 layer. This thick layer provided the structural support for the device. Chromium/gold electrode/heater metallization (0.5µ) was sputtered deposited and patterned on top of the thick SU8 (150µ) layer. 10µ PMMA was then spin coated as a protective layer for the selective deposition of PPy and enzyme. In order to prevent electrode pads from getting covered by PMMA, tape was applied on the electrode pads prior to the PMMA spin coating and was removed before the PMMA baking process. The PMMA layer was further selectively plasma etched in such a way that only one of the electrodes was exposed and the other electrode was covered. The metals were patterned using positive photo-resist and wet-chemical etching. Before the sputter deposition, a plasma surface treatment was employed to improve the adhesion between the SU8 and the metal layers. The device was then released from the glass substrate using a razor blade. The release layer was formed by spin coating a solution of amorphous fluoropolymers diluted with perfluorinated solvent.

Glucose oxidase (GOD), an enzyme prototype, was adsorbed electrochemically onto a polypyrrole (PPy) layer using a potentiostat together with an electrolyte solution consisting of 0.1 M, each of PPy and KCl at 0.8 V for 2 minutes. 0.1 M Ferricyanide and 8001 units/ml of GOD (18 µl GOD and 48 µl potassium ferricyanide (K3FeCN6) in 10 ml phosphate buffer solution) were further added in the electrolyte solution for the deposition of GOD. A redox electron mediator, such as potassium ferricyanide, may increase the sensitivity of the resulting measurement of the electrical property by maximizing current conversion. Selective deposition of Ppy+GOD was then done on one of the exposed electrodes of the sampling, analysis and chemical delivery device cell (FIG. 3). Chronoamperometric dose responses were recorded and the results revealed that the sensor had a good linearity from 0 to 10 mM glucose with the sensitivity of 2.9 mA/mM. For our lactate sensor chips we use the same process except we substitute lactate oxidase for the GOD.

The aforementioned embodiment is not intended to be limiting in any way and is provided as an example. It is contemplated that other materials and processes may be used to create the device 12. In addition, the cavity 28, as well as micro capillaries may be created in the thick support layer as the thick support layer is grown.

The micro capillaries may be used to manipulate the substance being sampled, such as interstitial fluid and/or the material in the cavity, depending on where the micro capillaries are located. The surfaces of the device 12 that may interface with a fluid, whether it is the substance being sampled and/or analyzed or the material being delivered from the cavity 28, may be selectively treated by plasma and/or chemical surface treatments so as to create hydrophobic or hydrophilic surfaces at precise, controlled points in the device 12. For example, to create a hydrophilic surface on SU-8, PDMS, silicon, or aluminum surfaces, silane derivatives may be used to treat the surface, and to create a hydrophilic surface with low contact angles on gold, silver or copper, alkane thiols may be used to treat the surface. Such examples of ways to alter the wetting behavior and transport ability of certain materials are not intended to be limiting in any way.

In an embodiment, a cell of the device includes three layers of PDMS and that are molded, metallized, and bonded together. Only a single cell of the device will be discussed herein, although it is understood that other cells of the device may be fabricated in substantially the same way. The middle support layer of PDMS includes a cavity and a pair of micro capillaries. The upper layer of PDMS seals the cavity, but includes a pair of micro capillaries that substantially align with the micro capillaries in the middle layer. The bottom layer of PDMS seals the bottom of the cavity and may include the electrodes and resistive element that are used to disrupt the cells of the stratum corneum, or a heater element in embodiments that are configured to ablate the stratum corneum for interstitial fluid applications. The bottom layer may also include a pair of micro capillaries that substantially align with the micro capillaries of the other layers.

For each of the layers of PDMS, a mold made from SU-8 may be used to create the cavity and the micro capillaries. The mold of SU-8 may generally be made by spin coating SU-8 on a substrate such as glass, and exposing and developing the negative photoresist SU-8 with the features (corresponding to the cavity and micro capillaries) being defined therein. Once the mold is created, the mold may be used in a press, and the PDMS may be applied to the mold within the press, and then cured in an oven. Once cured, the PDMS may be removed from the press and the mold. Other features of the cell, such as electrodes, may then be created by metallization processes in the appropriate layer of PDMS. After each layer of PDMS has the proper features, the layers may be bonded together such that the micro capillaries are substantially aligned with one another.

In addition, for zero-deformation release of the various layers of polymer materials, such as SU-8 and PDMS, from a glass or similar substrate during the creation of such layers, a variety of sacrificial layers of materials may be used. For example, for SU-8, polystyrene, a positive photo resist along with PDMS, and aluminum may be used as release layers. Polystyrene may be dissolved in toluene to thereby release the layer of SU-8 from glass or similar substrate. The positive photo resist may be dissolved in acetone and the PDMS may be used to help the resist absorb the acetone in order to release the layer of SU-8. Aluminum may be etched to release the layer of SU-8. For PDMS, potential sacrificial release layers that may be used to release the PDMS from the SU-8 mold described above may include photoresist (etched with acetone for release), aluminum (etched with phosphoric acid), silver (K12 etchant for release), and copper (K12 etchant for release). In addition, a fluoropolymer, such as CYTOP®, may also be used to condition the surface that receives the structural layer of polymer, to thereby enhance the releasing characteristics of the polymer and minimize deformation. By using a sacrificial layer of material and/or conditioning the surface, the deformation of the structural layer of interest may be minimized.

Of course, other variations of manufacturing a cell for the device may be used and the above-described embodiments are not intended to be limiting in any way. For example, it is contemplated that other polymer materials may be used for any of the layers of the device, including but not limited to polymer materials having a relatively low modulus for flexibility, such as polyolefins, polyesters, methacrylates, and polyimides, as well as stiffer polymer materials, such as polycarbonate and polystyrene.

In addition, the working electrodes may be created using techniques in addition to the one described above. For example, once the support layer has been created for the device, the support layer may be wired (via metallization) with electrical connections that extend from zero insertion force (ZIF) connectors located on a front, edge, or back side of the support layer to the specific desired location of the electrode. The metal components of the electrodes may also be electrodeposited before, during, or after the electrical connections are created. The ZIF connectors located at the front, edge, or back side of the support layer may then be connected to a controller that has been programmed with the specific layout and configuration of the cells of the device. When it is time to expose the working electrodes to a specific polymer matrix that my include the enzyme or antibody, the controller provides a signal to the selected cells that are to receive that particular polymer matrix at the particular locations at the ends of the electrical connections. For example, the controller may provide selected electrodes with a certain electrochemical potential with respect to ground, so as to create an anode or positively charged site. The selected electrodes may then electrochemically grow the coating or membrane out of the polymer matrix to thereby encapsulate the working electrode. The process may be repeated with different polymer matrices until all of the working electrodes are coated. This allows each cell to have an electrode coated with the particular sensing coating according to the design of the overall device. The sensing coatings may be designed to sense electrical properties including but not limited to electrochemical currents, capacitance, resistance, voltage-like potential, or electromotive force. In some embodiments, all of the working electrodes on a single device may have the same coating. In some embodiments, the half of the working electrodes may have one type of coating, while the other half may have a second type of coating, and so on.

Once the entire device has been fabricated, the same electrical connections that were used to grow the electrodes may also be used to apply a voltage potential across the sensing and reference electrodes when the substance is present and an electrical property of the substance may be measured. The electrical property may include current, capacitance, resistance, voltage-like potential, or electromotive force, depending on the polymer matrix that was used to coat the electrode. The electrical property may be correlated to a particular property of the substance, such as the level of a biomolecule in the substance, or a physic-chemical property, such as pH.

Figure 26:
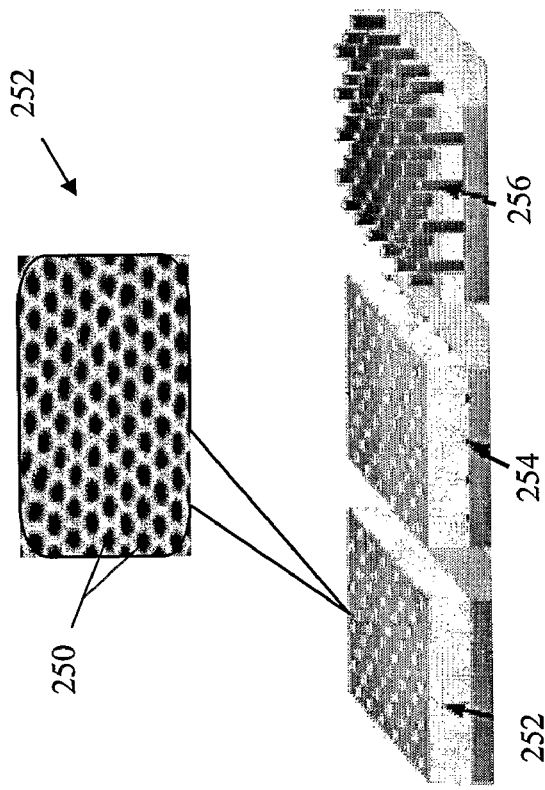
FIG. 26 is a schematic drawing of an embodiment of a method of growing an electrode for the device.

In an embodiment, the sensing electrode may be grown to include nanostructures on a surface thereof to increase the conductivity of the electrode. The conducting polymer polypyrrole (PPy) is a material currently being used for nanowire and nanotube based electrochemical biosensors and nanostructures because of its high environmental stability, electronic conductivity, ion exchange capacity, and biocompatibility. By capitalizing on the already high surface to volume ratio afforded by single nanotube or nanowire structures, a nanostructured film that resembles nano-grass has been created. The Ppy may be electrodeposited within pores 250 of a template 252 made from a sacrificial template-mediated material, such as aluminum oxide (alumina), as shown in FIG. 26. Once a nanowire array 254 has been grown from the PPy, the sacrificial template 252 may be removed via etching or any other suitable process, thereby leaving an array of PPy nanotubes 256 on the base layer of the electrode. It has been shown that with this nano-texturing method, polypyrrole can yield higher better conductivity performance than in bulk PPy films since the alignment of polymer chains is consistently along the wire axis.

The nanostructured film may be fabricated by a method the is similar to that described above, and may provide a simple and efficient biocompatible environment for the incorporation of proteins into the controlled matrix of the grown PPy nanowires. The conductive electro-active polymer that contains bioactive molecules (e.g. enzymes, antibodies, cells, and DNA) may be used extensively in biosensor applications and the mechanism of signal generation. For conducting polymers, pulsed amperometric detection and impedance spectroscopy were found to be most suitable for generating and analyzing antibody-antigen (Ab-Ag) signals. PPy electrodes have been prepared by galvanostatically electro-polymerizing the monomer pyrrole from an aqueous solution containing anti-human serum albumin (anti-HSA) on a polished Pt or Au electrode. With cyclic voltammetry (CV), it was shown that HSA does interact with these anti-HAS sensing layers, while no response is obtained with the control polypyrrole without incorporated antibodies. Use of nanostructures allows a greater amount of enzyme or receptor to be immobilized, thereby increasing sensitivity.

A variation on the stand-alone PPy nanotube array illustrated in FIG. 26 has been designed as a means to avoid three possible concerns with the pure Ppy nanowire arrays. First, there could be large series resistances observed in the nanowires due to their lengths (up to 50,000 nm) and due to field effects induced by anchored antibodies binding to antigens, yet a gold nanowire core is not effected by this. Second, the PPy's elastic modulus (about 80 MPa) is at least an order of magnitude less than gold (1.6 GPa), so gold core structures are stiffer and less likely to collapse or stick together in processing or while sampling. Third, the series resistance can also lead to both a lessening of collected current and therefore of detection sensitivity, and during processing, can translate to PPy nanostructures receiving less antibody at extremities rather than close to the conductive base electrode during electrochemical deposition.

Figure 28:
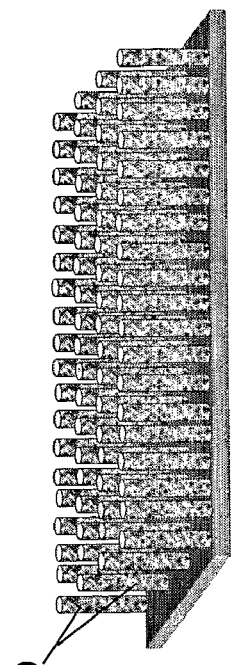
FIG. 28 is a schematic drawing of the array of nanotubes after the nanotubes have been coated.
Figure 27:
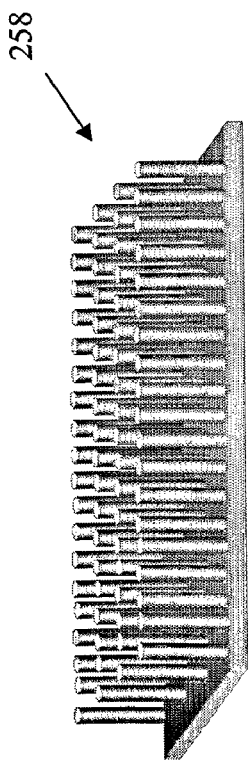
FIG. 27 is a schematic drawing of an embodiment of an array of nanotubes that have been grown on an electrode of the device.

An alternative fabrication scheme makes use of a metallic (Au) core, and can be described in four steps: 1) forming anodic alumina templates on a gold film, similar to the template shown in FIG. 26, 2) electrodepositing gold in the pores of the alumina pores from the underlying gold planar film electrode, 3) selectively etching the alumina template to expose gold nanowires, thereby leaving an all-metal nanostructure 258, as shown in FIG. 27, and 4) electrodepositing a few monolayers of Ppy film 260 on all exposed gold surfaces, as shown in FIG. 28. This method may reduce the resistance path provided for the electron flow within the nanotube since, in effect, a gold nanowire has been incorporated to run electrically in parallel with the conducting PPy nanotube. The effect would be a reduced resistance path for the nanowire when compared with the nanotube, and a greater signal should be present for the former for the same applied voltages. Again, a greater signal improves upon the sensitivity and overall performance of the biosensor in the device 12. Another variation to this process is that the Au can be replaced by carbon-based nanotubes that have been deposited vertically on a substrate, using standard growth processes. This may be followed with a coating of Ppy. One possible advantage of this process is that the carbon nanotubes are already conductive, and do not require any templates for their ordered vertical growth.

Other fabrication techniques that may be used to produce nanopatterned electrodes are based on related but distinct technologies compatible with the sensing chip device manufacture including, but not limited to dielectrophoresis (between two electrodes either on the device or between one electrode on the device and an external counter electrode), electrostatic deposition and vapor deposition. The materials so deposited are typically polarizable nanotubes or nanowires. In one embodiment, carbon nanotubes may be deposited on the sensing electrodes, and aligned to lie parallel between sensing electrodes or normal to the sensing electrode surface. These nanopatterned materials deposited on the sensing electrodes may exhibit large conductivity changes between the two probing electrodes when they absorb/adsorb a particular analyte using specific receptors.

In a related fabrication technique as described above for molding PPY nanorods, very thin metal filaments, including but not limited to aluminum, can be patterned one tip to form molded for PPY nanorods, or to deposit Carbon nanotubes. The resulting tip of the metal is covered by a dense collection of nanostructured material that is oriented in line with the wire itself. The other end of the conductive wire is connected to the device control and communication part. Mechanically, this material is pliable and easily deformable. Electrically the material is very conductive. For the neurological applications discussed below, the nanopatterned electrode material mimics the cilia structures occurring naturally at the tips of axons. Indeed, the nanopatterned material may be coated with thin layers of PPY in which is anchored nerve growth factor. Neural tissue may grow towards and attach to the nanopatterned material in such a way that the cells live and function properly indefinitely and excellent electrical contact is maintained.

Cavity Filling

Figure 21:
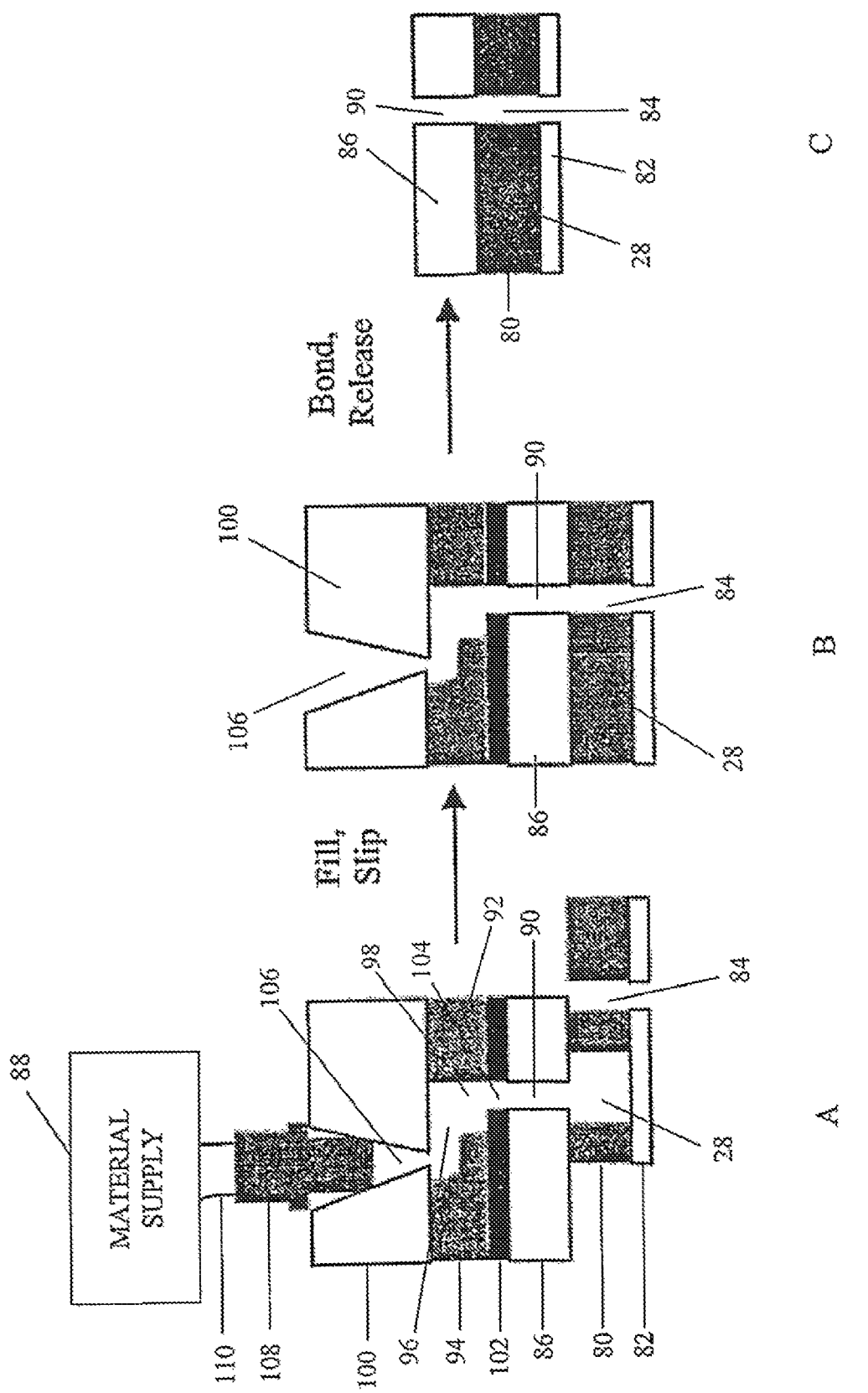
FIG. 21 is a schematic side view of part of a cell of the device illustrating an embodiment of filling and sealing the cavity of FIG. 8.

FIG. 21 illustrates an embodiment of an apparatus and method for filling the cavity 28 for cells that include a cavity 28. The cavity 28 may be formed by the molding process discussed above, or while a thick support layer (e.g., SU8) 80 is spin coated onto a layer of another material, such as PDMS, that constitutes a thin membrane 82, and at least one capillary hole 84, preferably two capillary holes, may also be created such that they extend parallel to the cavity 28 and through the support layer 80. The thin membrane 82 may also include capillary holes that are substantially aligned with the capillary holes 84 in the support substrate 80, as shown in FIG. 21. Another layer of polymer material, such as PDMS may be used as a seal layer 86 to seal the cavity 28 at its top after the cavity 28 has been filled with material from a material supply 88. The seal layer 86 is preferably thicker than the thin membrane 82 so that if the bubbling technique, described above, is used to burst the thin membrane 82 to provide access to the cavity 28 during use, the seal layer 86 will not also burst.

In an embodiment, the seal layer 86 also includes at least one capillary hole 90 that is initially aligned with the cavity 28 so that the material being supplied to the cavity 28 may pass therethrough and into the cavity 28. In an embodiment, the sealing layer 86 includes two capillary holes, shown in FIG. 22, that are spaced apart the same distance as the two capillary holes 84 of the support layer 80. The availability of two capillary holes in the seal layer 86 provides the option of using a push-pull mechanism during the filling of the cavity 28. One of the two capillary holes can be used as an entrance for the material, and the other capillary hole may be used to remove any remaining air from the cavity 28. To fill the cavity 28 with the material that is to be delivered to the substance, an interface between a material supply and the capillary holes may be created.

As shown in FIG. 21, an interface 92 may be provided to facilitate the filing of the cavity 28 with the material from the material supply 88. The interface 92 may include a glass carrier 94 with a reservoir 96 and a capillary hole 98 created therein, a layer of polymer material 100, such as PMDS, located on one side of the glass carrier 94 that is configured to interface with the material supply 88, and a release layer 102 on an opposite side of the glass carrier 94 that is configured to interface with the seal layer 86 of the sampling, analysis and delivery device. As illustrated, the release layer 102 also includes at least one capillary hole 104 therethrough that is configured to substantially align with the hole 90 in the seal layer 86.

The glass carrier 94 may be a photoetchable glass and the reservoir 96 and hole 98 therein may be etched. In an embodiment, the reservoir 96 and hole 98 in the glass carrier are created by powder blasting. The layer of polymer material 100 that is located on the top of the glass carrier 94 includes a hole 106 therethrough that may be shaped to receive a plug 108 at an end of a hose 110 that is connected to the material supply 88, as shown in part A of FIG. 21. This may help to positively locate and hold the plug 108 in place as the cavity 28 is being filled.

The layer of polymer material 100 may be bonded to the side of the glass carrier 94 that includes the reservoir 96 so as to align the hole 106 that is in the layer of polymer material 100 with the reservoir 96 in the glass carrier 94. This allows the material that is being supplied by the material supply 88 to fill the reservoir 96, and the reservoir 96 may be drained into the cavity 28 through the holes 98, 104, 90 that are in the various layers 94, 102, 86, respectively.

Once the material has been supplied to the cavity 96, the seal layer 86 of the device may be moved (e.g. slid) relative to the support layer 80 so as to seal the cavity 28, as shown in part B of FIG. 21. To ensure that the seal layer 86 has been moved to a position that ensures that the cavity 28 has indeed been sealed, the capillary hole 90 in the seal layer 86 may be aligned with the capillary hole 84 in the support layer 80, as shown in part B of FIG. 21. Once it has been determined that the seal layer 86 is in the correct position (e.g. the cavity 28 has been sealed), the seal layer 86 may be bonded to the support layer 80 and may then be released from the interface 92, as shown in part C of FIG. 21.

Figure 24:
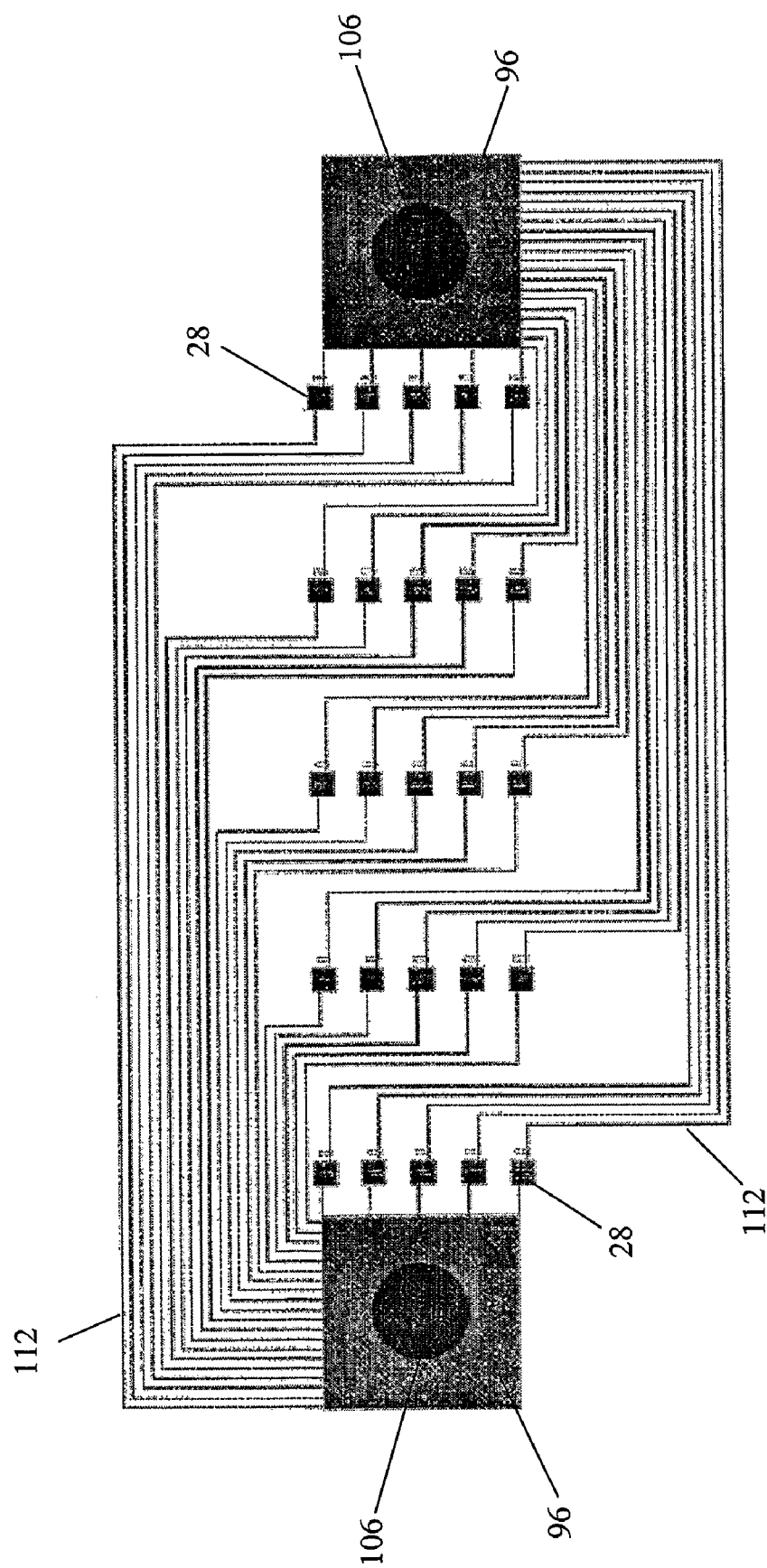
FIG. 24 is a schematic top view of an embodiment of an interface for simultaneously filling twenty five cavities of the device.

As described above, the cavity 28 for one cell 18 may be filled and sealed. In an embodiment, the glass carrier may be configured to provide channels to all of the cells 18 that include cavities 28 that are located on the same device 12. This way, the cavities 28 may be filled and sealed simultaneously. FIGS. 22-24 illustrate top views of such configurations. Specifically, FIG. 22 shows a single cavity 28 with the reservoir 96 shown as a square and the hole 106 in the layer of polymer material shown as a circle, thereby representing where the plug 108 would be positioned relative to the cavity 28 upon filling of the cavity 28. Similarly, FIG. 23 shows five cavities 28 being simultaneously filled, and FIG. 24 shows twenty-five cavities 28 being simultaneously filled. In each of these Figures, channels 112 in the glass carrier (not shown in FIGS. 22-24) that communicate the material between the reservoir 96 and the through holes 98 end exactly over the cavities 28. Also shown in FIGS. 22 and 23 are two capillary holes 84 that are in the support layer and are parallel to each cavity 28. Although two reservoirs 96 are shown in each figure, one of the reservoirs may be used to receive air that is displaced when the material enters the cavity 28, as described above. The illustrated embodiments should not be considered to be limiting in any way and are provided as examples as to how the cavities may be filled with material and sealed.

For example, it is contemplated that the support layer 80 may directly interface with the release layer 102, without that seal layer 86 being deposited on the support layer 80. In such an embodiment, the cavity 28 may be filled, and the seal layer 86 may be applied to the support layer 80 after the support layer 80 has been released from the interface 92 so that the cavity 28 may be sealed.

Connectors

For simplicity, a prototype realization of the control functions in a simplified system will now be discussed. The design of sampling, analysis and chemical delivery devices 12 were modified to make them compatible with zero-insertion force (ZIF) connectors. Chip thicknesses were adjusted to be 150 μm+/−10 μm for insertion reproducibility and the connector pad pin-outs were drawn to meet with the 300-pitch staggered connector positions. It is desirable to make "bottom" chip contacts that allow a flat connector and chip surface that can be pressed to the body of the subject. That is, there is no step in level at the connector body that prevents a good flat contact with the skin. In other embodiments, the chip contacts may be made on a front or side surface of the device. The body of the connector is 1.8 mm high in a surface mountable dual in-line package and is equipped with a ZIF slider mechanism that locks the chip into place once correctly inserted. We have seen that this allows us to change sampling, analysis and chemical delivery device sensor chips reproducibly in a minute, yet be sturdy enough to accept multiple insertions and to resist forces that would withdraw the chip from the socket due to the normal movement of the animal under experimental study. The part may be made in different widths that correspond to a range of 17 to 91 pin contacts. We have used the ones for 31 and 61 pins in our development work. For example, a 61 pin connector may be soldered to a wire cable, or the connector may be used with flexible multi-conductor Kapton tapes. In the integrated system, the connector may be rigidly connected to the body of the controller. The connector is available in both tape and reel-to-reel packages for economic automated assembly and manufacture.

Figure 31:
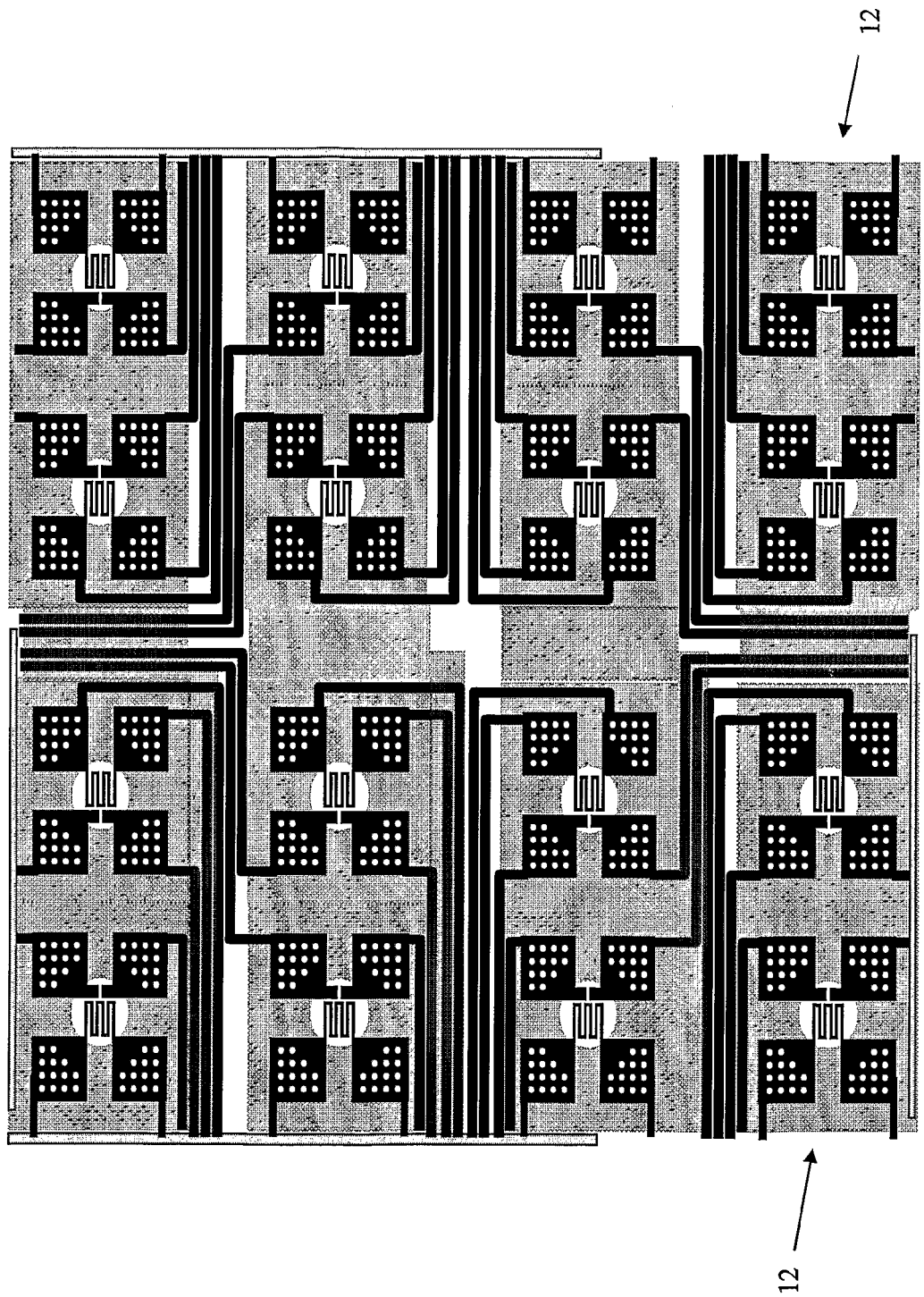
FIG. 31 is a schematic drawing of a top view of a plurality of devices of FIG. 29 during manufacture.

In an embodiment, the connectors may be created in the following manner. The process may start with a core substrate, made out of a flexible material such as polyimide or Kapton, which is typically 0.001" (1 mil=25 microns) in thickness, having thin conductive copper films (9 microns) laminated on both top and bottom sides. As shown in FIGS. 29 and 30, the device 12 may incorporate a micro-heater 270 on the bottom, or skin side, which has 1 mil trace widths. The electrochemical detection electrodes, represented in FIGS. 29 and 30 as 272, may be separate from the heater 270, but residing in close proximity. Disruption of the stratum corneum by applying a current pulse to the micro-heater 270 may generate a temperature of about 130° C., which when lasting for about 30 msec, is sufficient to cause individual stratum corneum cells to separate, thereby allowing for interstitial fluids to emerge onto the skin surface. The close proximity of the two electrochemical electrodes 272, one being gold while the other having electrodeposited poly-pyrrole embedded with a biomolecular enzyme and a redox mediator in some embodiments, or with an antibody in other embodiments, will allow for the specific detection of the biomolecule of interest. A bottom dielectric layer 274 supports a support substrate 278 which may have a plurality of capillaries 276 extending therethrough. A layer of copper 280 may be deposited on a top side of the support substrate 278, while another layer of copper 282 may be deposited on a bottom side of the support substrate 278 prior to the deposition of the dielectric layer 274. The top layer of the flexible circuit 280 may have bonding pads 284 that may be electroplated with copper to provide elevated bumps, or mesas. The bumps 284 may serve to provide more reliable electrical connectivity to the detection circuitry, which may be integrated onto a second flexible circuit (not shown) that may be mated with the topside bumps 284 on the device 12. Sampling sites may be arranged in an array (e.g., 4×4 as shown in FIG. 29) with connective traces to apply proper voltages during sampling, and during electrochemical detection and deposition (post-process). In the illustrated embodiment, the double-sided flexible substrate has the functional sensor and interconnect traces on the bottom side, while the top layer contains interconnects as well as contact pads to mate with another flexible substrate. FIG. 31 illustrates how the devices 12 may be laid out over a large substrate area, which may measure about 10"×12". The thick lines between devices 12 will be connected together to form common points for potentials to be applied prior to device separation. Also shown are interconnects for specialized post-processing that may involve conductive polymer immobilized with the enzyme, and for applying appropriate potentials during electrochemical detection.

Controlling and Communications Devices

The controller 14 generally consists of two parts. The first is a computer-interfaced wireless data collection system that is capable of addressing up to 64 remote sensor nodes, managing the identification of each one, as well as interrogating each one for the contents of its memory buffers. The second part is the sensor node. It may be made up of five functional parts, such as RF communication (with unique identification), a microprocessor controller, a multiplexer, analog circuit sources and A/D converters, and multiple sensor inputs. The microprocessor may be programmed for specific applications. The analog circuits, multiplexer and input lines may be specially configured to the particular device being used in the system. The range of communication may be upwards of about 300 m or even greater. In real time, the controller 14 calculates the necessary sequence of electrical signals required to perform the sampling, electrochemical analysis as well as continuous logging of the results, and chemical release.

The communications device 16 allows an external device to interrogate the controlling device 14 so as to perform a variety of operations including identifying the system, establishing the identity of the interrogator, transmitting stored information, allowing reconfiguration of the controlling program. Reconfigurations might include opening several sampling cells 18 on the device 12 surface to test for the same or multiple different analytes simultaneously, or choosing to increase, decrease or stop chemical release, or changing the frequency of sampling due to a detected stability or rapid change in measured concentrations, or adjusting the details of the pulses used to disrupt the stratum corneum. After potentially weeks of monitoring, the electrochemical sensing cells 18 may all be used-up, or encapsulations may all be opened such that the disposable sampling, analysis and delivery device 12 should be discarded and another one of an identical or different configuration may be inserted into the system 10.

Figure 20:
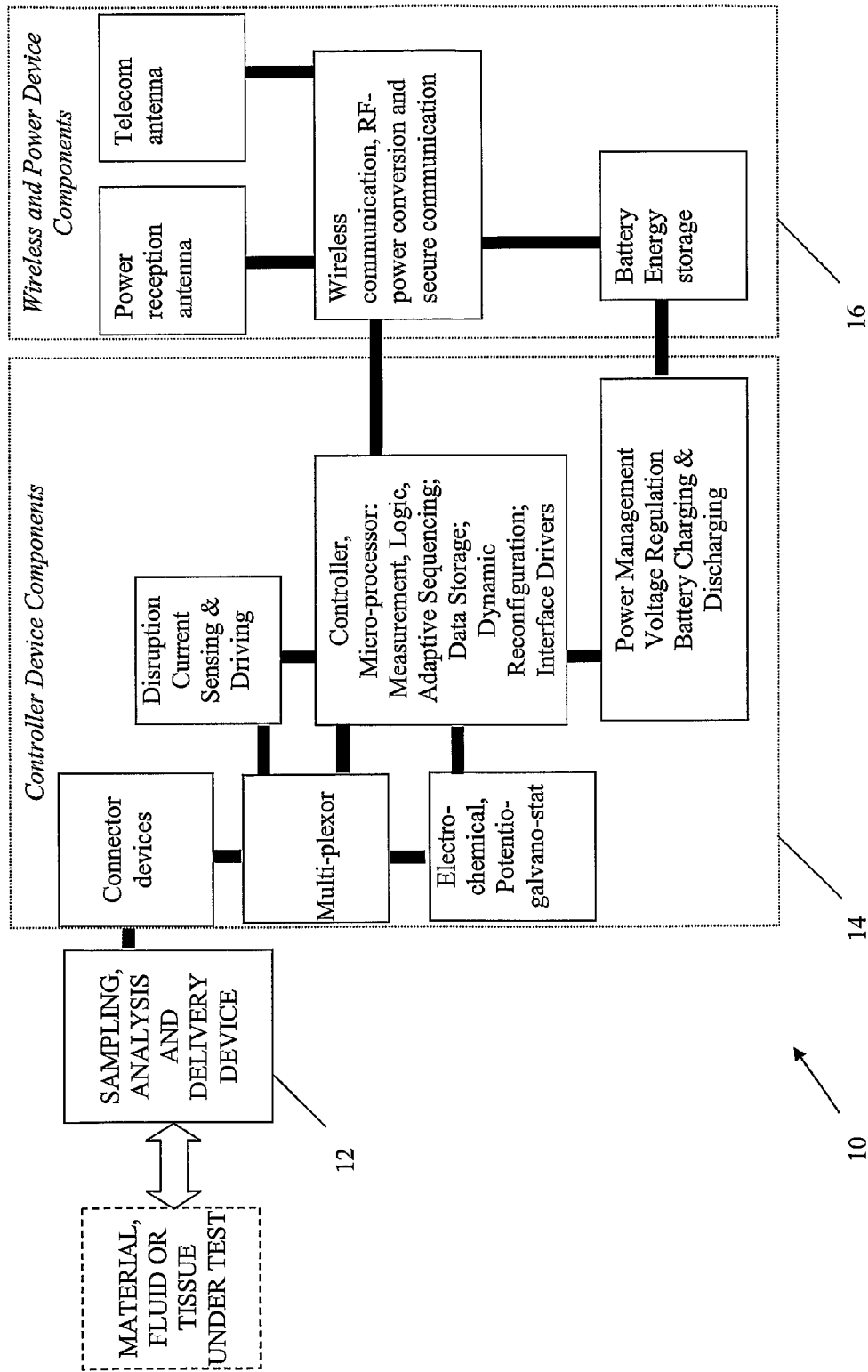
FIG. 20 is a block diagram indicating some components of the controller and wireless communication.

FIG. 20 is a block diagram indicating some components of the controller 14 and the communications device 16. In the system 10, the material, fluid or tissue under test interacts with the sampling, analysis and delivery device 12 that may be disposable, detachable and manufacture configurable. The components of the controller device 14 may comprise connector devices, a multi-plexor, an electrochemical potentio-galvano-stat, a disruption current sensing & driving circuit, a controller, a micro-processor for measurement, logic, adaptive sequencing, data storage, dynamic reconfiguration and to provide interface drivers, and a power management for voltage regulation and battery charging and discharging. The communications device 16 components may comprise a reception antenna, wireless communications modules, RF power management, and battery power storage.

It is contemplated that the controller 14 and communications device 16 may be one integrated system that is located within the same device, or the controller and communications device may be separate devices that interact via hard wiring or wirelessly. The above-described embodiments are not intended to be limiting in any way.

Figure 19:
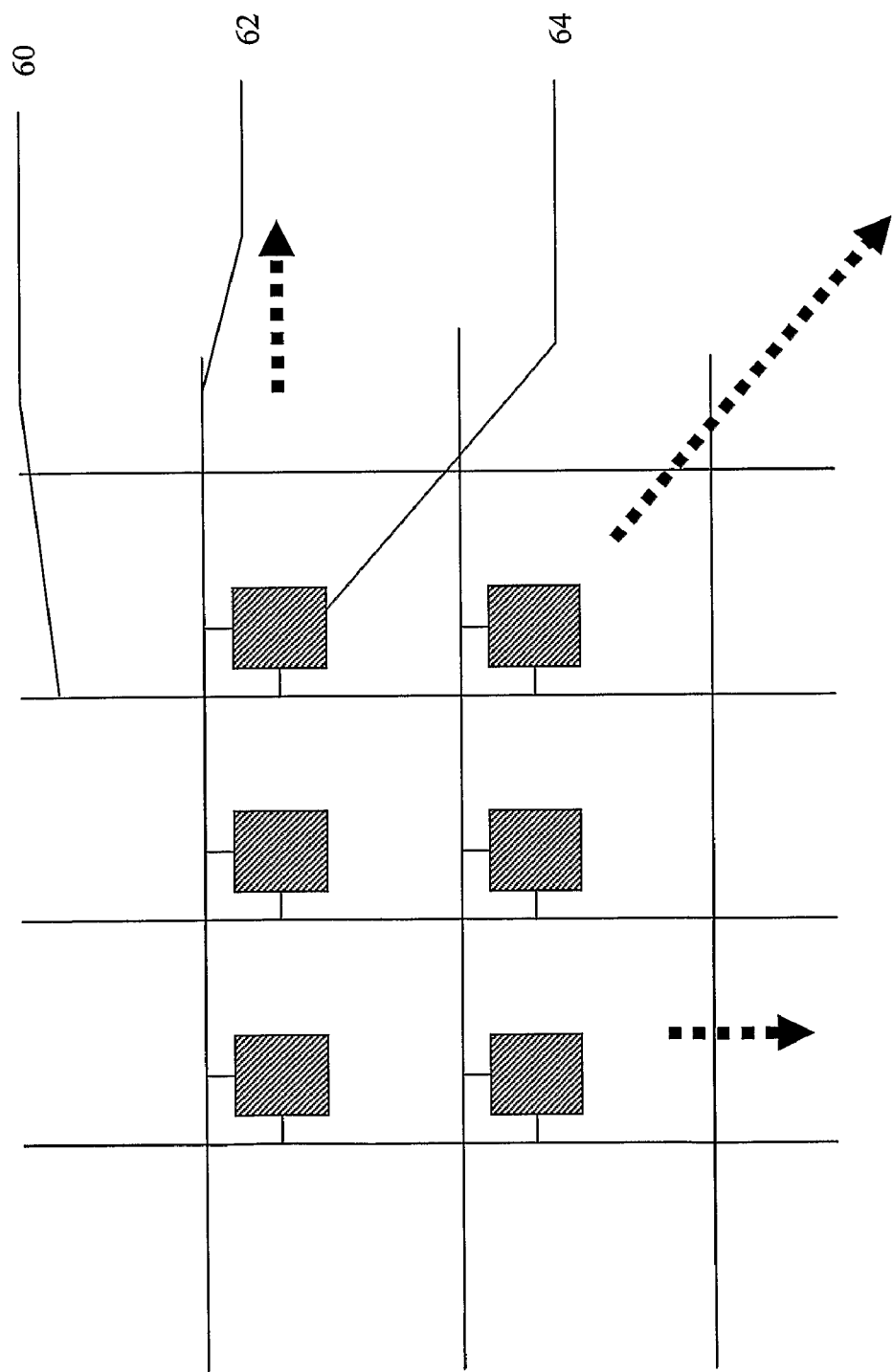
FIG. 19 illustrates an embodiment matrix of cell elements together with the row and column address lines.

FIG. 19 shows a random addressing of cell elements using row and column addressing. The address method comprises column address conductive paths 60, Row address conductive paths 62 and individually addressed sample, analysis and delivery cells 64. This method is used instead of a parallel addressing in which each cell has its own conductive paths connecting to the controller as shown in FIG. 2. For example 1024 cells organized in a matrix of 32 rows and 32 columns can be addressed sequentially by a 64-bit connector to the controller of which 32 connections are for the row address and 32 are for the column address. To perform simultaneous sampling and analyses, the controller must continually switch between sample analysis and delivery cells.

Examples of Applications Using Embodiments of the System

In an embodiment, the system 10 described above may be configured to monitor and treat diabetes. Type 1 diabetes mellitus (T1DM) is an autoimmune disorder that results from the destruction of the insulin producing pancreatic beta cells. To control blood sugars, subjects with T1DM must take multiple daily injections of insulin or use an insulin pump and check their glucose levels several times a day. Despite new and improved treatments, and studies showing that strict blood glucose control decreases the incidence of secondary complications of diabetes, euglycemia is difficult to achieve. One of the limitations to consistent euglycemia is the technology currently available to patients for measuring glucose levels. There are a number of competing technologies for collecting body fluids (e.g. blood, sweat, tears) and analyzing them for glucose monitoring based on optical, electrochemical, and spectroscopic methods. However, all have varying degrees and types of invasiveness. In sharp contrast to the available methods that have been developed thus far, the approach we describe in this application entails only superficial and highly controlled invasiveness (gentle heat and electric field assisted disruption of a microscopic section of skin), coupled with dynamic sampling of interstitial fluid.

The principal measurement target is glucose, with secondary targets being glucosylated hemoglobin and proteins, insulin, and cholesterol. The disruption of the skin allows approximately 10 nano-liters of interstitial fluid to diffuse, assisted by capillary forces to the surface of the stratum corneum. Glucose concentrations in blood and in interstitial fluid vary about an average of 90 mg/dl to as dangerously low as 40 mg/dl and as high as 600 mg/dl: over one decade for a diabetic and far less for a healthy person. Minimally invasive sampling of interstitial fluid is performed on any one of several sites of the body: most conveniently the inner arm or leg, and parts of the trunk. The adhesive may hold the flexible device 12 in contact with the area intended for sampling. A small volume of interstitial fluid can be encapsulated into one of the cavities 18 and preserved there for subsequent analysis. No modification of the sample needs to be performed. Each electrochemical analysis is completed in about 10 seconds. Three or more analyses may performed in parallel to improve accuracy and establish the statistical measurement uncertainty. The stratum corneum disruption may be maintained for hours with periodic heat and voltage pulses, and measurements may be performed accurately at will in this time period. The time to equilibrate concentrations inside and outside the stratum corneum is of the order of several seconds due to the very short diffusion path (<50 microns).

In another embodiment, the monitoring device 12 may be configured to store in the device cavities 18 calibrated samples of the analytes in question that can be released and measured on command of the control and communication system to further improve the accuracy of measurement.

In another embodiment, the monitoring device 12 may be configured to store in the multiple device cavities 18 either in dry powder form, or in water-dissolved form, a drug such as human insulin (in doses of about 1 unit) that can be released one at a time on command of the control and communication system. The decision to administer or deliver the drug may be made by a health professional, by the individual patient, or it may be made automatically. This later configuration is called closed-loop control. When the command and control system 14 is configured so as to keep glucose within certain bounds, and the glucose monitoring device detects hyperglycemia, insulin may be administered in a sequence. First, a partial dose is administered by opening one particular cavity, releasing 1 unit of insulin. After a few minutes, if hyperglycemia persists, a second partial dose is administered and so on until the complete dose is given. This pulsatile mechanism mimics that of a healthy pancreas releasing insulin into the blood stream with rising glucose concentration. It is possible for the amount of the complete dose to be modified based on the observed response to the pulsatile drug delivery, much as self-medicating diabetics are obliged to do when their individual response to insulin varies from day to day.

In an embodiment, the system may be configured for monitoring bilirubin levels in neonates. Bilirubin is a naturally-occurring toxic waste product of the body formed during the regular decomposition of hemoglobin, which is the iron-containing oxygen-transport respiratory protein that is in red blood cells. For neonates, there is typically an elevated rate of red blood cell breakdown, especially during the first few days of life. This elevated rate may overwhelm the metabolizing capacity of the neonate's organs, which have not been fully developed. An elevated rate of red blood cell breakdown typically generates elevated levels of bilirubin, which may make the neonate susceptible to jaundice. Abnormally high levels of bilirubin in neonates may lead to cerebral palsy, hearing loss, and other physical abnormalities. In extreme cases, untreated high levels of bilirubin may even cause death. Therefore, it is desirable to detect and treat an abnormal level of bilirubin as early as possible. Currently, bilirubin is measured by taking blood samples either from veins or via heel lacing. Such intrusive sampling methodologies on neonates are not desirable, as they may create significant discomfort. By configuring the above-described system to measure the concentration of bilirubin in neonates, a non-intrusive method, which may even be administered by the parents of the neonate after the neonate has been released from the hospital, may be provided.

In such a system, the target biochemical to be measured in the substance is bilirubin, and the working, conductive electrode of the device is configured to include immobilized biorecognition molecules, such as the bilirubin oxidase enzyme, within the polymer matrix of, for example, conducting polypyrrole (Ppy). Because bilirubin oxidase is an oxidative agent that results in the generation of positive ions when exposed to bilirubin, a shift in localized potential will be created. The shift will be proportional to the level of bilirubin present in the substance coming into contact with the working electrode. The electrochemical cell, described above, may detect this shift in potential, and may provide a signal to the controller. Once the sensor has been calibrated, the controller will be able to determine how much bilirubin is in the substance based on the signal from the cell.

In an embodiment, the system 10 is configured to monitor the ability of the human body to efficiently utilize its fuel resources. The actual source of energy used by muscles in any kind of activity is ATP (adenosine tri-phosphate), which can be generated either aerobically or anaerobically, that is, with or without oxygen, respectively. Anaerobic energy sources are typically used at the start of exercise and when the intensity of exercise is greater than that which can be supported by the available oxygen supply using aerobic sources. The point where this occurs is called the "anaerobic threshold", which is defined by the intensity of exercise/performance beyond which blood lactate concentration increases dramatically due to the body's inability to supply all its oxygen needs. The phosphate system and the lactate system are two sources of energy in the anaerobic system—phosphate for short bursts of energy, and lactate for intense, long duration performance. The lactate system uses sugar stored in the muscles and in the blood, however, the former is often utilized prior to the latter. The anaerobic breakdown of glucose results in the formation of lactic acid in the muscles however, in the presence of oxygen, it can be easily converted to ATP to become a fuel. Therefore, lactic acid may not accumulate if the intensity of exercise is low enough for it to be completely oxidized to make more ATP. When the rate of production exceeds the rate of removal, the lactic acid begins to accumulate and the bloodstream pH level (acidity) rises and the muscles do not function properly and begin to exhibit the familiar "burn". For highly trained athletes or for more leisure enthusiasts, it may be desirable to monitor stamina without reducing peak performance.

By using an embodiment of the device 12 that incorporates both glucose and lactate sensing sites, the system 10 may be used to monitor a user's maximum output without encroaching the anaerobic threshold. The controlling and communications devices 14, 16 that are in communication with the device (see FIG. 1) may be configured to relay information on an individual's glucose and lactate concentrations to their IPOD®, personal digital assistant (PDA), or cell phone, and give a graphic view that tracks the user's energy output in relation to the anaerobic threshold. The device 12 may provide continuous, non-invasive, and non-intrusive monitoring for use in the exercise and diet industry, for use by professional and Olympic-caliber athletes, for use in occupations that require intense energy outputs (such as firefighters, construction workers, etc), and may even find use with animals, both athletic animals (race horses and dogs) and worker animals. By using the devices 12 described above that include sensor cells that are configured to detect dissolved gas in interstitial fluid, pO2 concentration may also be monitored directly. The output signal from such sensor cells may also be combined with an independent oximeter that communicates its output in real time to the controller 14 and communications device 16. In addition, monitoring of coronary indications (through monitoring of, for example, C-reactive proteins, and/or homocysteine) in athletes would allow team trainers and physicians to be on the lookout for unsafe conditions. Team medical personnel could be alerted to pull a competitor before death or severe injury occurs. Additionally, testing for drugs such as steroids would have health benefits for athletes.

It has been found the a direct correlation exists between an individual's state of alertness and fatigue based on a measure of the person's glucose concentration. Indeed, this argument has been made with regard to chronic fatigue syndrome (CFS), which is characterized by an onset of debilitating, persistent fatigue and loss of energy lasting for more than six months, and that has not be attributed to any other medical or psychiatric disorder. It has been shown that glucose inhibits a particular class of glucose-sensing neurons that produce tiny proteins called orexins, which are central regulators of states of consciousness. If the firing mechanism of the orexin neuron has been affected, primarily due to even subtle changes in glucose, this may lead to varying states of alertness, narcolepsy, and even obesity. This raises the possibility that the modulation of orexin cells by glucose has a much wider behavioral role, contributing to the continuous daily readjustments in the level of arousal and alertness. It is contemplated that embodiments of the device 12 discussed above may provide clinical insight into CFS by monitoring glucose concentrations non-intrusively, and may also find use in the civilian population as an early-warning indicator of imminent fatigue. This would find use in occupations where being alert is of paramount importance, e.g. armed forces personnel, commercial pilots, school bus drivers, truck drivers, air-traffic controllers, among others. In an embodiment, the system 10 described above may also include an audible alarm that may be triggered to keep the individual in a state of readiness if the device 12 that is being used to monitor an individual senses that the individual's glucose concentration has reached level that indicates that the individual is becoming tired.

The potential to be successfully resuscitated from severe traumatic hemorrhagic shock is time-critical for both combat casualties and civilian trauma victims with traumatic exsanguinations. There are a number of research areas in which non-intrusive quasi-continuous field deployable monitors would increase the chances of a successful resuscitation. Firstly, for both triage and effective treatment, there is benefit in pin-pointing the precise moment of the shock time when the casualty is found by medics. The typical hematocrit, plasma glucose and lactate values observed during the hemorrhagic shock is known and four progressive phases have been identified, including: 1) early compensatory (homeostatic mechanisms), 2) maximal compensatory, 3) early decompensatory (during blood re-infusion, close to irreversibility) and 4) late decompensatory (leading to death). If resuscitative fluids can be administered before the late compensatory phase, when organs such as kidneys and the liver are ischemic, and there is severe acidosis, then chances for survival are greatly improved. Secondly, by incorporating very low concentrations of ethanol in the resuscitation fluid, plasma ethanol and its metabolites can be time-monitored as a marker of the degree of hepatic revived functioning. From a research point of view, a quasi-continuous (e.g. a reading every 2 minutes) would also shed light on the efficacies of both the volume and composition of the resuscitation fluid employed. There is evidence that small volumes of glucose infusions (not blood) can both moderate systemic acidosis as well as delay the onset of the fatal decompensation phases. Thirdly, to know even more precisely where one individual is situated on the compensatory/decompensatory time course, one must have a "baseline" prior to injury of that individual's plasma glucose and lactate (even alcohol) concentrations, which can be significantly altered from normal rest values by extreme stress and exertion as encountered in combat.

In this context, non-intrusive monitoring of lactate, glucose, bilirubin, pyruvate and ethanol (used as a marker) of each individual with the device 12 and system 10 described above throughout combat: from rest to exertion and possible injury is highly desirable. Knowing both the bilirubin concentration together with the rate at which ethanol is cleared by the liver gives extra data on the hepatic ischemia. Only the frequency of sampling changes from infrequent, to frequent, to quasi-continuous in the case of casualty when the monitoring device then serves as both a triage and a critical care instrument. When combined with other physiological instruments, a complete picture may be available for a commander, a medic or a field surgeon. The body's response to traumatic injury and to large area burns are very similar to that of hemorrhagic shock, and for this reason the sensors described above serve as well for the assessment of the severity of injury, to resuscitation and to response to treatment, especially to the proper functioning of the liver.

In an embodiment, the system 10 described above may be configured for use in monitoring a plurality of subjects being subjected to the same conditions. For example, soldiers of a platoon may each have a device 12 described above attached to his/her skin, and the devices 12 may communicate with a central command center. This way, each soldier may be monitored individually for a plurality of abnormal conditions. For example, glucose and lactate concentrations may be monitored. If the soldier is healthy, an individual rested baseline can be measured and stored. As the soldier exerts himself, the blood glucose and lactate levels can be monitored. Extreme exertion can be seen in hypoglycemia and elevated lactate levels. This physiological state may affect the soldier's ability to perform in battle or subsequent situations of high exertion. Thus, the command center may decide to call in the soldier for a rest period until it is detected that the glucose and lactate levels have returned to normal levels. In addition, if the soldier suffers a casualty, the sensors can be activated to measure quasi-continuously, and the system 10 may be used as a critical care and triage instrument in the manner described above.

In an embodiment, the subjects may be animals that are in a herd or in a common environment. For example, the device 12 described above may be attached to the ears of some or all of the animals in a herd. The devices may be configured to measure the glucose levels of the animals over time. A central command node may be located on a gate at a distance, e.g. a quarter of a mile, away from the herd. The command node may be configured to send a signal to interrogate all of the devices within its range so as to locate those animals that may be in distress due in infection. By monitoring the glucose levels of the animals, when an elevated level is detected, thereby indicating that the animal may be in distress, the distressed animal may be separated from the herd, examined, and tested to more precisely determine the type of an origin of its illness. The devices may be configured to use either antibody or enzymatic coatings that target specific abnormalities in the subjects that are reflected by specific disease markers that may be present in blood, milk, urine, etc. In this way, the system may perform as a wire-less point-of-sampling monitor that can relay its assay results in real time to a command node and immediately signal the presence of infection. In an embodiment, the system may be used to analyze milk samples before the milk is loaded onto refrigerated tankers at each collection point to ensure the milk is safe for consumption.

In an embodiment, the system may be configured to monitor for viability and functionality of organs and tissues that have been prepared and stored for surgical implantation. For example, specific biomolecules that may be present in the organs and tissues may be monitored to ensure the organ or tissue is still suitable for implantation. These biomolecules may be desirable or may be undesirable.

The simplest test of the viability of most tissues is the assessment of the levels of glucose, lactate, blood gases of oxygen, carbon dioxide, and pH. As long as these concentrations fall within bounds, the cells of the tissue are capable of maintaining a normal metabolism. Other tests are appropriate to assess the functionality of more complex tissues such as the liver, heart, lung, kidney, and neural tissues. For example, as described above, hepatic functioning can be monitored by analyzing bilirubin concentrations as well as the liver's ability to eliminate molecules such as ethanol. The device 12 configured for these applications is similar to the geometries previously described with the possible exception that if the organ or tissue is exposed, for example in surgery, the device 12 may be applied directly to the tissue to access interstitial fluid without the complication of barriers like the stratum corneum. Certain organs have envelope tissues which act as barriers as well. In this case the disruption of the barriers may be accomplished adjusting the temperature and voltage levels for the properties of the envelope. For organs in stasis, for which artificial circulation is used to maintain function, devices 12 may be used to monitor both the input and output circulation fluids to assess the ability to eliminate certain molecules, such as ethanol in the liver. Neural tissues may require special configurations of the device 12, as described below, in order to measure accurate electrical signals over long periods without damage to the neurons themselves.

Similarly, small masses of tissues may be excised from a body by surgery or a minimally invasive probe. The small masses may be conveniently placed on top of a device 12 for analysis of the contents for the interstitial fluids. The device 12 may measure the sample rapidly (e.g., in seconds) before the tissue begins to deteriorate, and may measure trace concentrations of biomolecules. The precise panel of assays performed on the biopsy sample will depend on what the disease is that is under investigation. In most if not all cases, the very tiny volumes (nl) of interstitial fluid analyzed should not perturb the biological state of the biopsy tissue.

In embodiments, the system 10 described above may be configured to be used for early detection of diseases, including but not limited to cancer and infectious diseases, such as influenza, malaria, and Dengue fever. In such embodiments, the device 12 (e.g., the sensing electrodes of the device) may be prepared with antibodies that bind to certain antigens whose abnormal concentration is associated with an elevated risk for disease or infection, or simply the presence of a growing tumor mass or infection. For many diseases, there are growing numbers of biochemical markers linked to disease. In the case of prostate and breast cancers, specific antigens that are routinely tested are prostate specific antigen (PSA) and prostate membrane specific antigen (PMSA), estrogen, epidermal growth factor (EGF), and insulin growth factor (IGF). Antibodies are available for all of these antigens and can be selectively anchored to the electrodes of the device 12. All the antigens are smaller than 60 kDa and are found in interstitial fluid. The tests available for these cancer markers are therefore transdermal, but also urine and breast aspirate fluid. For the highest sensitivity to the lowest concentrations, the method of described above of nano-patterning the electrodes may be used. For viral, or spore born infectious disease, two different configurations of the device 12 may be needed. The first measures exposure to the virus or spore and uses electrodes with antibodies raised to the virus of interest such as H5N1 virus. Spores are detected by looking for specific metabolites externally. The electrodes may be nano-patterned, as described above, so as to pick up the lowest concentration and give the earliest warning of an individual's exposure to the infectious agent. One does not become ill immediately on exposure. Only when external concentrations of influenza virus is high does the virus begin to circulate in blood. The virus and spore are too large to be found in interstitial fluid, but viral fragments (Hemagglutinin and Neuradminidase) are found in interstitial fluid. Antibody detection is possible within minutes with such configurations of the device 12 at the 1-million fragment per ml interstitial fluid concentration level, which is sufficiently low to respond to antiviral medication treatment.

In an embodiment, the device 12 may be configured to monitor and treat the infectious parasitic disease malaria. In an embodiment, the device 12 may be configured to monitor both the presence of the parasite as well as markers related to functioning of organs like the liver, kidney, brain and lungs. In particular, the device is made to be sensitive using both antibodies and enzymes to characteristic metabolites released by the parasitic protozoa (genus plasmodium), such as, among others, Histidine-rich protein 2 of P. falciparum (PfHRP2), parasite lactatedehydrogenase (pLDH). The malaria affects and ultimately damages these organs leading to further deterioration of health, referred to as disease burden. Markers for each organ are measured to determine how far concentrations are from normal to deduce organ stress or damage. In another embodiment, the delivery cavities 18 of the device 12 may be configured to deliver sequentially or in combination, as determined by a healthcare professional, the individual or automatically by the control and communication portions of the device, Artemisinin together with primaquine and older drugs to which the parasite is now more resistant. In an embodiment, the device may be similarly configured to monitor and treat other diseases, such as HIV and tuberculosis, such that the device may monitor the disease and its burden, and administer drugs or combinations of drugs.

In embodiments, the system may also be configured for therapy of cancer and infectious diseases. Although there are several types of conventional and genetic therapies being developed, tested, and used for treating cancer, there are very few non-invasive and highly sensitive measurement techniques or systems that quantitatively monitor trace biomarkers during an individual's response to a treatment protocol. Of these, only a handful are based on biomolecular pathways common to nearly all radio- and/or chemo-therapeutic agents, and none offer the possibility of continuous monitoring both at critical times and throughout the duration of therapy. Using the methods described above to produce nano-patterned polymers on the device's sensing electrodes, proteins present in the programmed cell death biological sequence of apoptosis may be specifically targeted. This includes, but is not limited to the 17 kDa subunit of cleaved caspase-3 at biologically relevant concentrations, namely between 1 ng/ml and 0.1 mg/ml. Several of the proteins in cell apoptosis like p54 and the 17 kDa protein have been shown to be useful as a surrogate marker for the efficacy of the majority of cancer treatments that induce cell apoptosis.

In embodiments, the system may be configured for sampling of fluids within a subject's mouth. For example, the system may be configured to detect bacteria, viruses, microbial film, inflammation and caries, as well as normal hormones, proteins and metabolites to assess overall wellness of the subject. The constituents of human saliva and other oral fluids contain many analytes of interest for screening, diagnostic, and monitoring applications, and samples can be easily acquired using a variety of non-invasive, low-risk methodologies. Saliva is generated from plasma and glands and as such, plasma proteins and drugs enter tissue interstitial spaces based upon Starling forces and vascular permeability. Similar forces regulate the flux of interstitial proteins, low-molecular weight materials, drugs, ions and water across the buccal and gingival mucosa. The buccal mucosa provides a readily accessible site to approach the tissue interstitium and to sample interstitial fluids. The relative transfer rate across the oral membrane from plasma to saliva can be determined by measuring concentrations of drugs, plasma protein, and other analytes in the two fluids simultaneously. In general, the system described above may have potential applications in drug pharmacokinetics, detection of illicit substances, and monitoring plasma/interstitial drug or mediator levels. Furthermore, it is well known that various synergistic interactions of microbes in the gingival crevice activate inflammatory mechanisms that can lead to caries, gingivitis, and other oral pathology. Specific patterns of microbe-specific proteins, metabolic products, host proteins, and degraded products of interstitial connective, dental, and bone tissue may be identified. By sampling crevicular fluid, followed by standard proteomic analyses (liquid chromatograph/mass spectrometry/mass spectrometry, or LC-MS-MS), patterns of unique or altered products may define disease-specific bio-signatures. In view of this, we employ three microfabrication technologies for the non-invasive sampling of such fluids and bio-films for obtaining information on pre-disease states.

In one specific configuration, the sampling device may be augmented by electrodes and microfluidic channels adjacent to the sampling cavity, in which isoelectric focusing and capillary electrophoresis (2-D separations) are performed. The results of the separations may be detected electrically, as described above, or the separated sample may be preserved in cavities for subsequent analysis outside the device using mass spectrometry.

Salivary diagnostics may be accomplished by sampling from a region between the gums and cheek using micro-capillary "toothpicks" for the detection of oral cancers, cariogenic bacteria in the development of dental caries (cavities), the efficacy of therapeutic drugs, illicit drug abuse, and HIV or herpes viruses. Oral bio-films (dental plaque scrapings), along with crevicular fluid collection using micro-capillaries attached to a dental probe device, can assist in the detection of periodontal diseases, *Helicobacter pylori*, and oral malodor. Interstitial fluid may be sampled from the relatively permeable mucosal membrane lining the mouth using an embodiment of the above-described non-invasive sample collection device 12, thereby allowing for the determination of systemic diseases and drug testing. Rapid clinical diagnostic tests that may be configured to be used as a screening mechanism to determine certain pre-disease states, such as gingivitis or other diseases, may be performed with an embodiment of the system that is in the form of a salivary-based in-home or in-office diagnostic "popsicle-stick."

The dental system may be used for, but not limited to two specific diagnostic areas: the first is to sample interstitial fluid, saliva, and other oral fluids in order to determine a molecular bio-signature, or salivary "fingerprint", correlated to many clinical conditions such as risk factors, susceptibility to disease, and general health status. The second diagnostic area is directed towards oral disease, focusing on the effects of saliva and salivary constituents on cariogenic bacteria and the subsequent development of dental caries, including the role of immunoglobulin A (IgA) in the prevention of acidogenic bacterial colonization.

Three types of micro-sampling devices may be used, with each device being specific to the type of oral fluid being analyzed. First, a micro-capillary bundle may sample saliva from between the cheek and gum region, while multiple micro-capillaries attached to a dental probe may be used for sampling gingival crevicular fluids. The third micro-sampling device is a modification of the system used for glucose sampling, described above, to sample interstitial fluid through the mucosal membrane. This sampler, unlike the first two, includes a small battery, and is mounted on a depressor-like device. The sampling process may be initiated by pressing a button while the device is pressed against the cheek. The sample may be stored upon releasing the button. This structure may be used to collect salivary and trans-mucosal fluids for the detection of systemic markers. Numerous studies have shown a high degree of correlation between the constituents of serum (systemic indicators) and oral fluids from the buccal mucosa.

The micro-capillary bundle sampler device, comprised of an assembly of micro-capillaries, may be used to collect saliva samples from between the cheek and gum region. The micro-capillary collection unit allows for sampling of significant volumes of saliva over a specific distribution area using a hand-held device resembling an eye-dropper. The individual micro-capillaries are commercially available and are made of micron-scale glass tubing covered with an outer sheath layer of polyimide to provide rigidity and durability. Dimensions for both inner and outer diameters vary for each of these micro-capillaries, with inner diameters as small as 30 microns and outer diameters of up to 350 microns.

For an easy-to-use hand-held sampler 300, in an embodiment illustrated in FIG. 32, bundles of individual micro-capillaries 304 may be inserted into a bulb pipette 302 having a flexible bulb 303 at one end thereof, and held in place by "potting" them in a silicone elastomer called polydimethylsiloxane, or PDMS 306. In the illustrated embodiment, the sampling bundle 304 has been loaded into a molding pipette (not shown), similar to the pipette 302 illustrated in FIG. 32, followed by pouring and curing of the silicone PDMS potting material 306. The PDMS 306 does not cover the ends of the micro-capillaries 304 on either side so that sampling can occur through the capillaries, while suction and dispensation onto a lab-on-a-chip device is possible with the use of the bulb. Once cured, the composite silicone and micro-capillary structure 308, or PDMS plug, two of which are shown in FIG. 33, may be removed from the molding pipette, so that other similar bundles encased in PDMS can be made. For sampling purposes, the user may employ the bulb pipette 302, and after removing the bulb 303, may insert a PDMS plug 308 into the pipette 302 as far as it will go. The tapered nature of the bulb pipette 302 will ensure that the micro-capillaries 304 will be at the proper location during sampling and will seal the open end of the pipette 302. The bulb 303 may be re-attached and the sampling of saliva may occur between the cheek and teeth. The PDMS plug 308 may be removed and stored for analysis at a later time, or the sampled fluid may be dispensed directly into the separation apparatus. The purpose of the PDMS plug 308 is to provide new holders or vials to be used for each sampling procedure. The illustrated embodiment is not intended to be limiting in any way.

In an embodiment, a micro-capillary based dental probe device 400, illustrated in FIG. 34, is provided. Periodontal probing is the most commonly used method in determining periodontal pathology and the degree of clinical attachment of the gum with the tooth. Generally, a depth of space of about 1-3 mm is considered acceptable. The aim of this micro-capillary-based device 400 is to sample crevicular fluids during a standard periodontal examination to determine the extent of connective tissue pocket depth. In an embodiment of the system, a platform may be configured to receive as the device substrate a commercially-available, disposable, and easy-to-use periodontal probe 402 made of flexible polymer plastic. The periodontal probe 402 may be modified by using micro-capillaries 408 that have very small outer diameters (approx. 100 microns) and may be attached on transverse sides of the tapered probe 402, and held in place by a 25 micron thin layer of cured PDMS silicone rubber 410. Since a distal end 406 of the probe 402 is nominally 0.5 mm in diameter (or 500 microns), the attached micro-capillaries 408 and PDMS layers 410 will increase only the device lateral dimension by 0.25 mm. By using PDMS, the overall flexibility of the probe may be retained, and an adverse reaction should not be created when introduced in vivo for short times. The crevicular fluids may be passively transported into the two micro-capillary tubes 408 through capillary action. In another configuration, the micro-capillaries 408 may be connected to a suction device (as commonly found in dental offices) for gently drawing the crevicular fluids up the micro-capillary tubing 408. In another embodiment, a single micro-capillary may be disposed inside the shank of the probe by using a molding procedure to form the probe around the micro-capillary. The illustrated embodiment is not intended to be limiting in any way.

In embodiments, the device 12 and system 10 may be configured to be used to assist in the continuous long-term management of the balance between the caloric intake and caloric expenditure, which is due to base metabolism and physical exertion. The device 12 may be configured in this case to measure physiological and biochemical history throughout a day for weeks at a time. In one example, base metabolism may be established by monitoring movement, flexion of muscles under the skin, heart rate, skin temperature, skin conductivity, interstitial fluid oxygen and carbon dioxide gas concentrations, and interstitial fluid glucose, lactate, insulin, ghrelin and leptin concentrations. Movement is best measured by the incorporation of one or multiple-axis accelerometers in the circuitry of the command and control part of the device 12. Movement as well as muscle flexion, and the small detectible pulse of blood through arteries and veins (hence measuring heart rate) beneath the flexible sensing part of the device using the voltage produced by a piezoelectric layer (polymer of ceramic) embedded in the substrate of the device 12 as the device 12, which is adhered to the skin, deforms with the skin. The temperature may be assessed by means of measuring the variations in the resistance of a material having a known temperature coefficient of resistance deposited between measuring electrodes, or by using the material of the heater shown in FIG. 29, for example.

Skin resistance may also be measured conveniently by either two or four electrode techniques. In the two-electrode technique, resistance may be calculated from either the DC or AC current of a particular frequency passing between two open electrodes in contact with the skin and from the known applied voltage. For this measurement, electrodes in one cell of the device 12 may be used as well as electrodes in different cells of the same device 12 to achieve a separation of several millimeters so as to remove the effects of local skin texture, features, or compositional variability. In the four electrode technique, ideally using single electrodes at each of the four corners of the device 12, a known DC or AC current is passed between two adjacent corner electrodes through the skin and the electrical current is measured between the two opposing electrodes. This technique may remove the usually small uncertainty of the contact resistance between the electrode and the skin and results in a value unique to the skin. In the case that exertion results in heavy sweating, the conductive sweat may shunt the resistance measurement. AC measurements taken at different oscillation frequencies may be used to separate the sweat contribution to conductivity from that of the skin and of the fatty tissues below the stratum corneum in the dermal layers. The biochemical assays may give a continuous measure or the metabolism experienced within the body, and this is responsible for as much as 60% of total caloric expenditure. The measurements are not only all collected and stored individually by the controller 14, but may also be interpreted so as to give a best estimate of total caloric intake. This total value may be displayed either in an analog or digital fashion to inform the individual of the accumulated caloric expenditure.

Caloric intake, appetite control, satiety, fat production and consumption may also be quantifiable with the measurements. Glucose and insulin concentrations measured at the time of ingestion and digestion may provide a quantifiable assessment of how many calories are absorbed at a meal. The actual number of calories absorbed are quite different than one estimated from calorie counting of the foods to be eaten. Following ghrelin concentrations after eating indicates satiety. By measuring the increase in the concentration of ghrelin, the onset of satiety may be detected before the physical satiety feeling is experienced, thereby avoiding over eating. By following glucose and insulin levels before eating, the physiological signal of appetite may be measured. By comparing caloric expenditures to intake when one feels hungry, an intelligent decision of whether or not to eat and how much to eat may be made.

As is known, weight loss occurs when the body expends more calories than it absorbs over a period of weeks. By monitoring caloric balance closely, one can day-to-day maintain a healthy deficit for fatty-weight loss. Leptin is one of many peptides in the biological system that produces, maintains and eliminates fat by sending signals to the hypothalamus. Measuring leptin provides a direct gauge of how the body is managing its fat volume. The four point electrical resistivity (impedance) when conducted at a variety of AC frequencies may also be correlated to the amount of fatty tissues in the current path. This electrical analysis together with the leptin concentration allow the system's control and communication devices 14, 16 to post not only the state of accumulated fatty tissues at the point of analysis but also the rate at which that mass is increasing or decreasing. These are all valuable tools currently unavailable to an individual to closely and un-intrusively control body weight and body composition through conscious intervention to assist the autonomous mechanisms of energy storage and use.

Although diets include ample supplies of protein, fat and carbohydrates, often food intake lacks certain essential minerals, vitamins and acids. In one non-limiting configuration, cells 18 of the device 12 may be prepared to measure available concentrations of these in the interstitial fluid. These molecules are small and are easily found in the interstitial fluid. In an embodiment, the cells 18 of the device 12 may be prepared to measure through electrochemical, enzymatic and antibody mechanisms concentrations of mineral ions such as calcium and potassium, vitamins such as Vitamin-A, and acids like folic acid. Deficiencies of these nutrients are not necessarily reflected in obesity or weight loss but are thought to have consequences for osteoporosis, and neurological disorders.

In embodiments, the system 10 generally described above may be used to cardio, vascular, and stroke monitoring. Technically termed myocardial infarction or MI, heart attacks have been diagnosed in the past based on the presence or history of chest pain and characteristic changes in the wave patterns on an electrocardiograph (ECG). More recently, the results of the creatine kinase (CK and CK-MB) blood tests have been used in diagnosis, while cardiac troponin is beginning to be used. Troponin's main advantage is that it is very sensitive to even minor damage to the heart. Troponin, a protein that has three isotypes (I, T, and C), is released from dead and injured cells in heart muscle, so elevated levels can indicate that there has been injury, such as would occur during a heart attack, even a mild one. Other advantages of troponin, particularly TnI and TnT, over the CK-MB test are that it remains in the blood stream for days following a cardiac event, allowing more time for diagnosis, and, while CK and CK-MB are only released from muscle cells that have died (the definition of infarction), troponin is released and severely injured muscle cells. Studies have shown that people who have elevated troponin but normal CK and CK-MB suffer similar consequences to those who meet the more traditional diagnostic criteria for diagnosing a heart attack.

The presence of plaque in the carotid arteries, which bring blood to the brain, is associated with strokes, either by transmitting blood clots to the brain or by stopping blood flow and causing stroke. People with atherosclerotic carotid arteries also are more likely to have atherosclerosis in the coronary arteries and throughout the circulatory system, thereby making them more susceptible to heart attack, as well. Tumor necrosis factor and its receptors are markers for inflammation that become elevated in the blood in a variety of infectious, inflammatory, and autoimmune diseases. Experimental evidence suggests that immune processes and inflammation play a role in the development of artery thickening. Elevated levels of tumor necrosis factor receptors may be a reflection of the inflammatory processes operating in the formation of plaques.

For use in such monitoring, the system 10 may be configured to monitor a panel of analytes that are indicative of healthy heart and circulatory functions and may provide early indications of abnormalities that can lead to heart attack, circulatory problems and stroke. In an embodiment, the cells 18 of the device 12 may be prepared to measure simultaneously the concentration of the analytes in interstitial fluid, including but not limited to C-reactive protein, tumor necrosis factor receptors 1 and 2, creatine phosphokinase (CK and CK-MB), creatinine, troponin, interleukins 1, 2 and 6, interleukin-2 receptor, and tumor necrosis factor-alpha.

In an embodiment, the system 10 may be configured for substance and drug abuse monitoring, such as monitoring of smoking, alcohol use, narcotics, etc. Nicotine, and its metabolite cotinine, may be monitored transdermally using the system 10 described above. The oxidation of nicotine to cotinine is catalyzed by the cytochrome P-450 2A6 enzyme, located in cell mitochondria. Cotinine is often used to differentiate between smokers and non-smokers, that is, those that are subject to second-hand smoke, also known as environmental tobacco smoke (ETS). Passive smoke, in contrast to mainstream smoke, contains greater amounts of ammonia, benzene, carbon monoxide, nicotine, and carcinogens, such as n-nitrosamines. Monitoring of smoking may be used by parents to ensure their children are not engaging in or abusing tobacco. More importantly, doctors may monitor expectant mothers during pregnancy and after birth as these two activities are the major and independent risk factors for sudden infant death syndrome (SIDS). More recent studies also indicate that an as identified constituent of second-hand smoke may affect the neuroregulation of breathing, which could result in episodes of sleep apnea and SIDS. Studies have shown that the lungs of infants who die from SIDS have significantly higher levels of nicotine than control subjects. Tobacco use may be monitored on a continuous basis using our non-invasive patch technology. The system 10 may be incorporated with tamper-proof controls that would indicate that the device 12 had been taken off the user for periods of time, presumably during smoking. The device 12 may also be used as a stand-alone in vitro tool for a urine sample, which typically is where cotinine is excreted from the body, to be introduced on a sampling site on the device 12.

In embodiments of the invention, the device 12, using either enzymatic detection using an electrochemical reaction, or specific immobilized receptor sites making use of antibody-antigen detection using resonant frequency shifts of a vibrating suspended membrane, may be used to monitor illicit substances including performance enhancing drugs, drugs of abuse (opiates, cocaine, narcotics), and the abuse of alcohol. The device 12 may incorporate several panels of detection cells to monitor an individual for a variety of illicit substances, or can be specific for a particular substance.

In an embodiment, the system 10 is configured to make use of the vertically oriented micro-capillaries, discussed above, that are perpendicular to the skin's surface. By capillary action, the sampled interstitial fluid may be drawn upwards through the capillary. The same capillary may be filled with a gel, such as polyacrylamide or agarose, which provides a semi-porous medium for the sampled interstitial fluid to flow through. However, capillary action may not be effective so a voltage may be applied using electrodes situated at the top and bottom of the capillary. By applying a low-level potential, the interstitial fluid may be electrophoretically driven since the dimension of the gel-filled capillary is only several hundreds of microns. Thus, a low voltage would still produce a high electric field, since $E=V/d$, thereby allowing for the separation of biological constituents within the gel based on charge/mass ratio. The effective 1-D separation may then be further analyzed once the device is removed from the user.

In an embodiment, the system may be configured for neural interfacing, for short or long-term interfacing (e.g. prosthetic control, therapeutic response. In addition, the system may be configured to monitor and possibly treat neurological disorders, such as depression, anxiety, and multiple sclerosis. By using the compliant deformable nanopatterned material on thin wire electrodes, described above, that has been coated with nerve growth factor anchored in electrochemically deposited PPY, the device may obtain excellent biocompatible connection to living neurons. It is possible that the connection is due to both the intimate and long-term adhesion between the neuron and the filamentary nanoscale conductors through which current passes assisted by a tunneling mechanism.

In an embodiment, the system may be configured for environmental biosecurity, by monitoring animals, crops, water, and food supplies. The introduction of foot and mouth disease to the United States represents the single greatest biological threat to our country's trillion dollar agricultural industry over the next twenty years. The system described may be configured to provide a scalable platform to determine the disease distribution across the country or within a specific location. If individual surveillance is needed a real-time, high throughput non-invasive assessment may be coupled to an onboard test for a presumptive determination of infection. Subsequent effort on the individual level may be taken if a specific individual is positive.

In a related biosecurity area, the device may be configured for a particular chemical such as a particular pesticide. Environmentally induced diseases affect everyone to one degree or another however individual susceptibilities can predispose the degree of toxic reaction of one group over another. In particular, individuals in their developmental stages, ranging from the embryonic phase to adolescence, are particularly susceptible to such environmental stresses since key body functions have not matured to a level where they can tolerate, process and handle such exposures. The use of biomarkers incorporated within the device may provide a continuous monitoring of a child's environmental health, and for the early detection of toxins, prevention of impairment in their physical condition, and determine a course of treatment for children who have been exposed to toxic environments containing, for example, pesticides. Many different pesticides exist but most affect the nervous system by disrupting the enzyme that regulates acetylcholine, a neurotransmitter. Pesticide monitoring can also be used in crops for a variety of reasons including but not limited to optimization of chemical treatment with regard to yield; to ensure crops do not get over-treated; and to monitor farm products from vendors who claim to be free from pesticide use. The device may be used as a stand-alone device, where soil samples can be placed on the sensor site. The water contained in the sample may reach the sensor containing the proper receptor panel set for a variety of pesticides, and an indicator may give information regarding the concentration of pesticide in the environment.

It is also contemplated that the system described above may be configured to be used for detection and treatment in a wide variety of applications that have not been described herein.

As should be appreciated by one of skill in the art, the contemplated applications for the above-described system are far reaching and limitless. The examples of applications that have been described above should not be considered to be limiting in any way. Instead, they have been given as examples as to the wide utility that the embodiments of the invention may provide.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

What is claimed is:

1. A sensor for sensing a property of a substance comprising a biomolecule, the sensor comprising:
    a flexible substrate;
    a micro-heater formed on the surface of the flexible substrate, wherein the micro-heater is configured to repeatedly generate a temperature sufficient to disrupt the stratum corneum without ablating the cells to obtain the biomolecule;
    a first pair of electrically conductive paths coupled to the micro-heater;
    a pair of electrodes supported by the flexible substrate and positioned proximate to the micro-heater, the pair of electrodes comprising:
        a reference electrode; and
        a working electrode being electrochemically activated and configured to react with the biomolecule; and
    a second pair of electrically conductive paths coupled to the reference electrode and the working electrode.

2. The sensor of claim 1, further comprising a plurality of nanostructures supported on a surface of the working electrode.

3. The sensor of claim 2, wherein the nanostructures are selected from a group consisting of nanowires and nanotubes.

4. The sensor of claim 2, wherein the nanostructures comprise a polymer matrix, the polymer matrix comprising an electrically conductive polymer and one or more bioactive molecules.

5. The sensor of claim 4, wherein the bioactive molecules are selected from a group consisting of enzymes, antibodies, cells, and DNA.

6. The sensor of claim 5, further comprising:
    a cavity formed within the flexible substrate;
    a protective membrane sealing the cavity; and
    a resistive element disposed between the reference and working electrodes, the resistive element being configured to disrupt the protective membrane to provide access to the cavity.

7. The sensor of claim 6, wherein the working and reference electrodes are at least partially disposed within the cavity.

8. The sensor of claim 6, further comprising one or more piezoelectric detection devices disposed within the cavity.

9. The sensor of claim 6, further comprising a delivery material contained within the cavity.

10. The sensor of claim 9, wherein the delivery material is selected from a group consisting of a chemical, a drug, a biomolecule a protein, a peptide, and a genetic material.

11. The sensor of claim 1, wherein the flexible substrate comprises one or more micro-capillary holes.

12. The sensor of claim 1, wherein the flexible substrate comprises a multilayer polymeric metal laminate structure.

13. The sensor of claim 1, wherein the flexible substrate includes a piezoelectric material configured for measuring a deformation of the sensor.

14. The sensor of claim 1, wherein at least the working electrode is encapsulated in a protective membrane, wherein the membrane is selected from a group consisting of selectively permeable membranes and non-permeable reactive membranes.

15. The sensor of claim 3, wherein the nanostructures comprise carbon-based nanotubes.

16. The sensor of claim 8, wherein the one or more piezoelectric detection devices are configured to measure a change in resonate frequency due to binding of the biomolecule.

17. A sensor for sensing a property of a substance comprising a biomolecule, the sensor comprising;
    a flexible substrate;
    a micro-heater formed on the surface of the flexible substrate, wherein the micro-heater is configured to repeatedly generate a temperature sufficient to disrupt the stratum corneum without ablating the cells to obtain the biomolecule;
    a pair of electrodes supported by the flexible substrate, the pair of electrodes comprising:
        a reference electrode, and
        a working electrode being electrochemically activated and configured to react with the biomolecule; and
    an external counter electrode.

18. A sensor for sensing a property of a substance comprising a biomolecule, the sensor comprising:
    a flexible substrate, comprising:
        a cantilevered beam formed using a piezoelectric material, wherein the cantilevered beam is configured to measure a deformation of the sensor; and
        a pair of electrodes supported by the flexible substrate, the pair of electrodes comprising:
            a reference electrode; and
            a working electrode being electrochemically activated and configured to react with the biomolecule.

19. The sensor of claim 18, further comprising a plurality of nanostructures supported on a surface of the working electrode.

20. The sensor of claim 19, wherein the nanostructures are selected from a group consisting of a nanowires and nanotubes.

21. The sensor of claim 19, wherein the nanostructures comprise a polymer matrix, the polymer matrix comprising an electrically conductive polymer and one or more bioactive molecules.

22. The sensor of claim 21, wherein the bioactive molecules are selected from a group consisting of enzymes, antibodies, cells, and DNA.

23. The sensor of claim 22, further comprising:
    a cavity formed within the flexible substrate;
    a protective membrane sealing the cavity; and a resistive element disposed between the reference and working electrodes, the resistive element being configured to disrupt the protective membrane to provide access to the cavity.

24. The sensor of claim 23, wherein the working and reference electrodes are at least partially disposed within the cavity.

25. The sensor of claim 23, further wherein the cantilevered beam is disposed within the cavity.

26. The sensor of claim 23, further comprising a delivery material contained within the cavity.

27. The sensor of claim 26, wherein the delivery material is selected from a group consisting of a chemical, a drug, a biomolecule a protein, a peptide, and a genetic material.

28. The sensor of claim 18, wherein the flexible substrate comprises one or more micro-capillary holes.

29. The sensor of claim 18, wherein the flexible substrate comprises a multilayer polymeric metal laminate structure.

30. The sensor of claim 18, wherein at least the working electrode is encapsulated in a protective membrane, wherein the membrane is selected from a group consisting of selectively permeable membranes and non-permeable reactive membranes.

31. The sensor of claim 20, wherein the nanostructures comprise carbon-based nanotubes.

32. A sensor for sensing a property of a substance comprising a biomolecule, the sensor comprising;
    a flexible substrate, comprising:
        a piezoelectric material configured to measure a deformation of the sensor; and
        a pair of electrodes supported by the flexible substrate, the pair of electrodes comprising:
            a reference electrode;
            a working electrode being electrochemically activated and configured to react with a biomolecule; and
    an external counter electrode.

33. The sensor of claim 18, wherein the cantilevered beam comprises an analyte receptor agent, wherein the cantilevered beam is further configured to measure a change in resonate frequency due to a change in the mass of the cantilevered beam that occurs when an analyte contained in the biomolecule binds to the analyte receptor agent.

34. The sensor of claim 18, wherein the cantilevered beam comprises an analyte receptor agent, wherein the cantilevered beam is configured to measure the deformation of the sensor by measuring surface stress resulting on the cantilevered beam when an analyte contained in the biomolecule binds to the analyte receptor agent.

* * * * *